United States Patent
Kim et al.

(10) Patent No.: US 6,552,080 B1
(45) Date of Patent: Apr. 22, 2003

(54) FUNGICIDAL COMPOUNDS HAVING A FLUOROVINYL-OR FLUOROPROPENYL-OXYPHENYLOXIME MOIETY AND PROCESS FOR THE PREPARATION THEREOF

(75) Inventors: Bum Tae Kim, Daejeon (KR); No Kyun Park, Daejeon (KR); Gyung Ja Choi, Daejeon (KR); Jin Cheol Kim, Daejeon (KR); Chwang Siek Pak, Daejeon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 10/049,412

(22) PCT Filed: Aug. 16, 2000

(86) PCT No.: PCT/KR00/00906

§ 371 (c)(1),
(2), (4) Date: Feb. 7, 2002

(87) PCT Pub. No.: WO01/12585

PCT Pub. Date: Feb. 22, 2001

(30) Foreign Application Priority Data

Aug. 16, 1999 (KR) .............................. 99-33722
Aug. 16, 1999 (KR) .............................. 99-33724

(51) Int. Cl.[7] ................. A01N 37/12; A01N 37/44; A01N 37/18; A61K 31/165; C07C 229/00
(52) U.S. Cl. ................. 514/539; 514/619; 514/620; 560/35; 564/163; 564/165; 564/256
(58) Field of Search ................. 560/19, 35; 564/163, 564/256, 165; 514/539, 619, 620

(56) References Cited

U.S. PATENT DOCUMENTS 5,221,691 A * 6/1993 Clough et al. .............. 514/619

* cited by examiner

*Primary Examiner*—Richard L. Raymond
*Assistant Examiner*—Zachary C. Tucker
(74) *Attorney, Agent, or Firm*—Anderson Kill & Olick, PC

(57) ABSTRACT

A fungicidal compound of formula (I) having a fluorovinye- or fluoropropenyl-oxyphenyloxime moiety and stereoisomers thereof are useful for protecting crops from fungal diseases: wherein, X is CH or N; Y is O or NH; $R^1$ is hydrogen, $C_{1-4}$ alkyl, or halogen-substituted $C_{1-4}$ alkyl, $R^2$ is a phenyl group optionally carrying one or more substituents selected from the group consisting of $C_{1-4}$ alkyl, $C_{1-4}$ alkoxy, methylenedioxy and halogen; or a naphthyl group; and $R^3$ is hydrogen or $CF_3$.

(I)

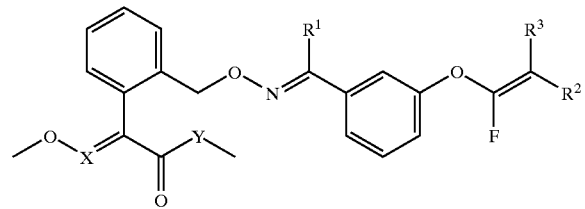

7 Claims, No Drawings

FUNGICIDAL COMPOUNDS HAVING A FLUOROVINYL- OR FLUOROPROPENYL-OXYPHENYLOXIME MOIETY AND PROCESS FOR THE PREPARATION THEREOF

This application was filed under 35 U.S.C. 371, and is the U.S. national stage of PCT/KR00/00906, filed Aug. 16, 2000.

FIELD OF THE INVENTION

The present invention relates to novel fungicidal compounds having a fluorovinyl- or fluoropropenyl-oxyphenyloxime moiety, a process for preparing same and a fungicidal composition containing same as an active ingredient.

DESCRIPTION OF THE PRIOR ART

A number of fungicidal compounds have been in practical use to protect crops from various pathogenic fungi; and they may be classified into several groups according to their similar structural features. However, the repetitive use of a fungicide over a long period induces the appearance of new fungal strains resistant not only to the particular fungicide but also to related fungicides having common structural features. For this reason, continuous efforts have been undertaken to develop novel fungicides.

Such efforts have led to the development of new fungicides, e.g., propenoic esters derived from strobilurin (U.S. Pat. No. 4,994,495; WO 94/19331; U.S. Pat. No. 5,003,101) and other propenoic ester fungicides disclosed in EP A 0 278 595 (Zeneca), EP A 0 782 982 (Novatis), WO 96/33164 (Ciba-Geigy), WO 96/33164 (Rhone-Poulenc Agro), WO 98/56774 (BASF), WO 99/06379 (BASF), WO 99/23066 (Agrevo UK), German Patent Nos. 724,200 and 732,846 (both BASF), and British Patent No. 22,893 (Agrevo UK). However, these propenoic ester derivatives still have the problem of limited fungicidal activity.

SUMMARY OF THE INVENTION

Accordingly, it is a primary object of the present invention to provide a novel compound having a high fungicidal activity against a wide spectrum of plant pathogenic fungi.

It is another object of the present invention to provide a process for the preparation of said compound.

It is a further object of the present invention to provide a fungicidal composition containing said compound.

In accordance with one aspect of the present invention, there are provided a novel compound of formula (I) and stereoisomers thereof:

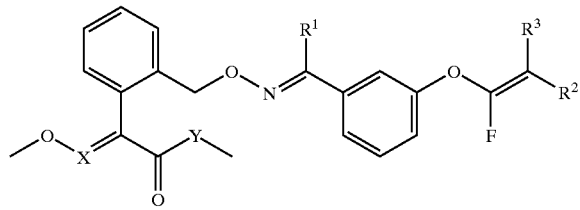

(I)

wherein,
X is CH or N;
Y is O or NH;
$R^1$ is hydrogen, $C_{1-4}$ alkyl, or halogen-substituted $C_{1-4}$ alkyl;
$R^2$ is a phenyl group optionally carrying one or more substituents selected from the group consisting of $C_{1-4}$ alkyl, $C_{1-4}$ alkoxy, methylenedioxy and halogen; or a naphthyl group; and
$R^3$ is hydrogen or $CF_3$.

DETAILED DESCRIPTION OF THE INVENTION

The structure of the compound of formula (I) of the present invention is characterized by the fluorovinyl- or fluoropropenyl-oxyphenyloxime moiety, and depending on whether X is CH or N, it may also be classified as a propenoic acid derivative (X=CH) or as an iminophenylacetic acid derivative (X=N).

Among the compounds of the present invention, preferred are those wherein $R^1$ is hydrogen or methyl, and $R^2$ is phenyl group, or Cl- or F-substituted phenyl group.

The compound of formula (I) of the present invention may be prepared, as shown in Reaction Scheme A:

Reaction Scheme A

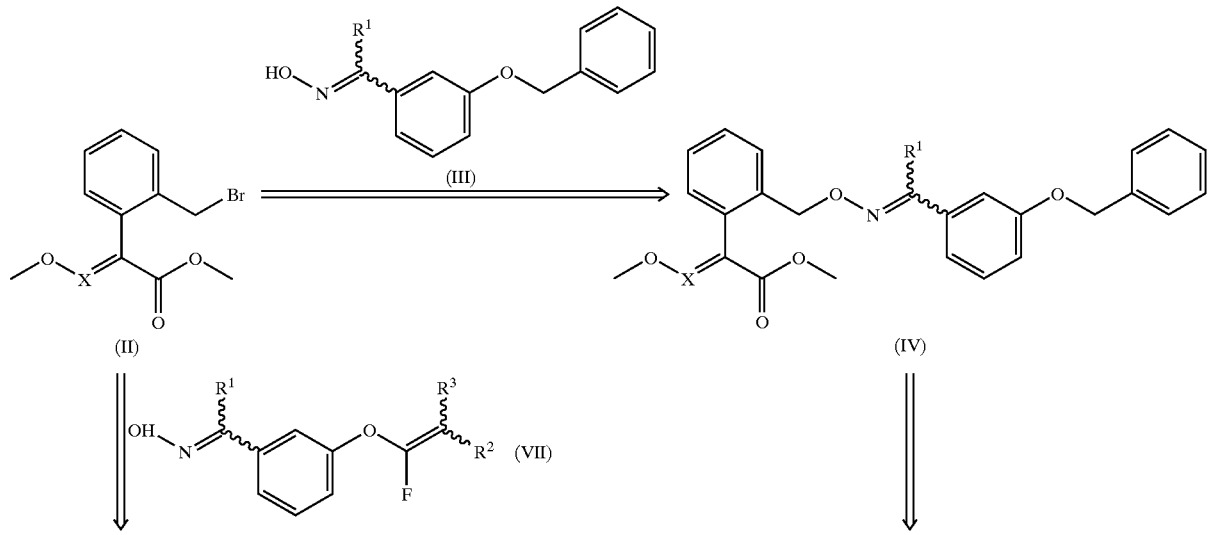

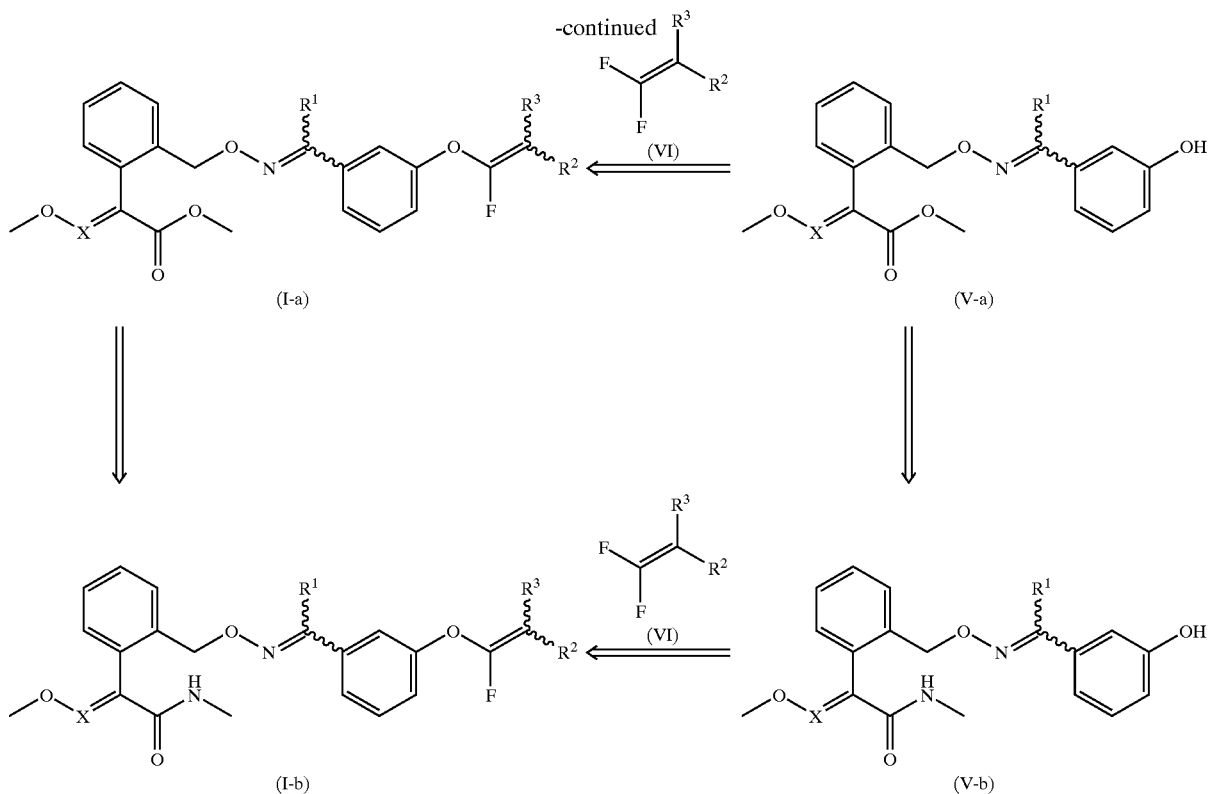

wherein, X, $R^1$, $R^2$ and $R^3$ have the same meanings as defined in formula (I) above.

In Reaction Scheme A, the compound of formula (I-a), i.e., a compound of formula (I) wherein Y is O, may be prepared by the steps of (a) reacting a compound of formula (II) with an oxime derivative of formula (III) in the presence of a base to obtain a compound of formula (IV); (b) debenzylating the compound of formula (IV) by hydrogenolysis in the presence of a Pd(C) catalyst to obtain a compound of formula (V-a); and (c) reacting the compound of formula (V-a) with a compound of formula (VI) in the presence of a base:

The compound of formula (II) is inclusive of the compounds of formula (II-a) (X=CH) and formula (II-b) (X=N):

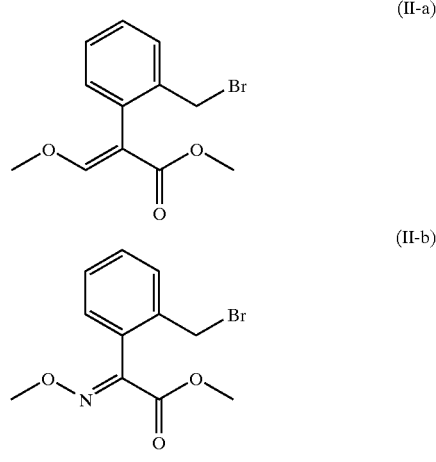

The compound of formula (II-a) may be prepared by esterification, formylation, methylation and bromination of o-tolylacetic acid according to a conventional method (Yamada, K. et al., *Tetrahedron Lett.*, 2745(1973); Vyas, G. N. et al., *Org. Syn. Coll.*, 4, 836(1963); Kalir, A., *Org. Syn. Coll.*, 5, 825(1973); Korean Unexamined Patent Publication Nos. 98-83587 and 99-15785; and World Patent Publication No. WO 99/07665), as shown in Reaction Scheme B:

Reaction Scheme B

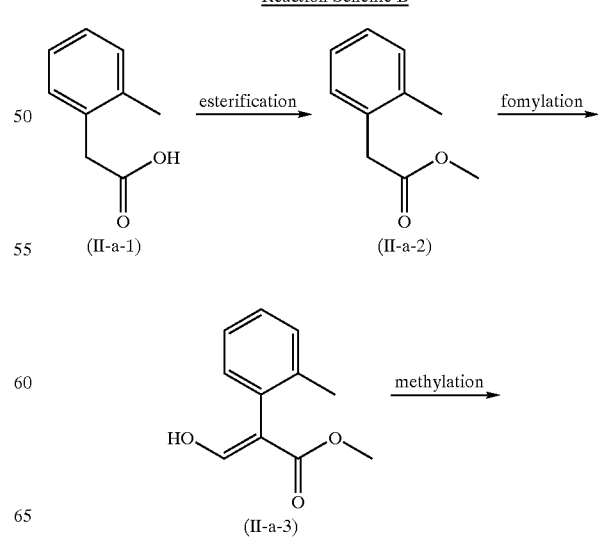

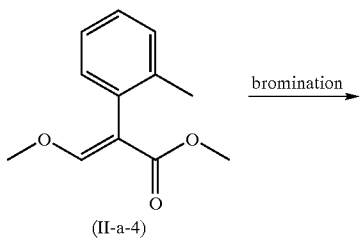

(II-a-4)

bromination→ 5

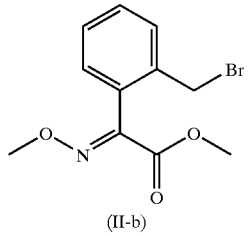

(II-b)

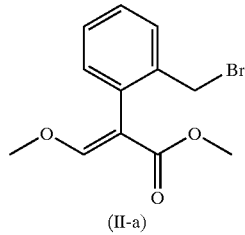

(II-a)

The compound of formula (II-b) may be prepared by Grignard reaction, oxalylation, condensation, methylation and bromination of o-bromotoluene according to a conventional method (Rambaud, M. et al., *Synthesis*, 564(1988); Korean Unexamined Patent Publication Nos. 98-83587 and 99-15785; and World Patent Publication No. WO 99/07665), as shown in Reaction Scheme C:

Reaction Scheme C

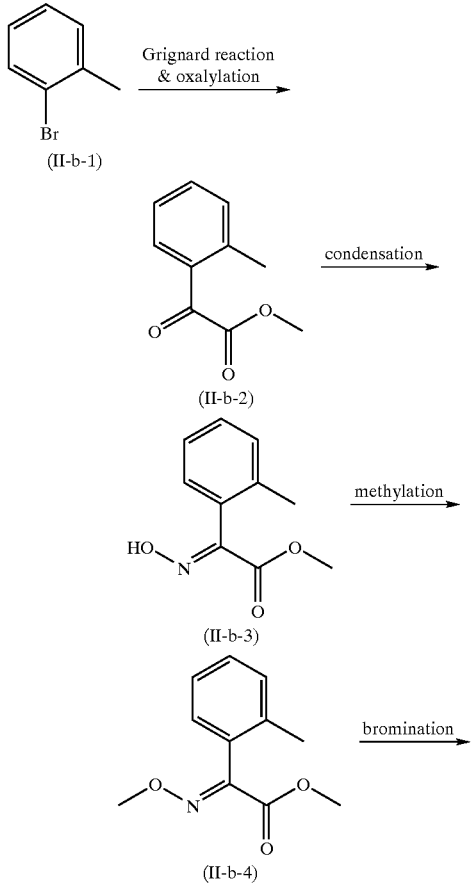

The compound of formula (III), on the other hand, represents, among others, the compounds of formula (III-a) ($R^1$=H), formula (III-b) ($R^1$=$CH_3$) and formula (III-c) ($R^1$=$CF_3$):

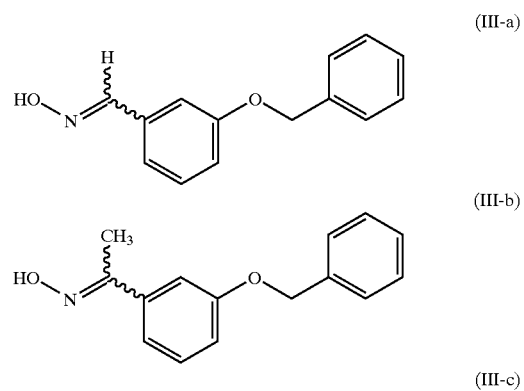

The compounds of formulas (III-a), (III-b) and (III-c) may be prepared by the steps of benzylation and condensation of 3-hydroxybenzaldehyde, 3-hydroxyacetophenone and 3-hydroxy-2'2'2'-trifluoroacetophenone, respectively, in accordance with a conventional method (Kuhn, R. et al., *Chem. Ber.* 90, 203(1957); Fletcher, H. G. et al., *Methods Carbohydr. Chem., II*, 166(1963); Freedman, H. H., et al., *Tetrahedron Lett.*, 3251(1975); Lichtenhaler, F. W., et al., *Tetrahedron Lett.*, 1425(1980); and Sugg, E. E., et al., *J. Org. Chem.*, 50, 5032(1985)), as shown in Reaction Scheme D:

Reaction Scheme D

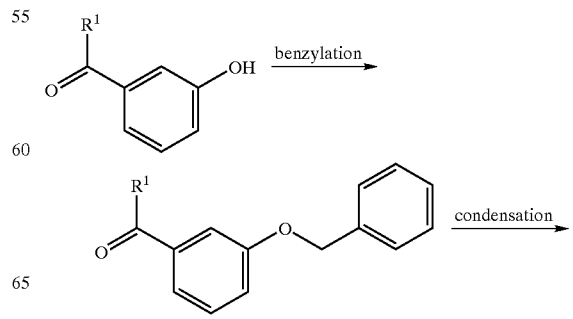

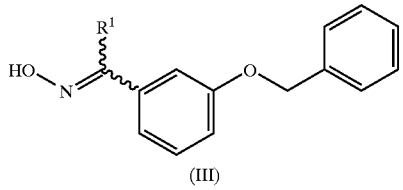

(III)

wherein, $R^1$ has the same meanings as defined in formula (I) above.

In the reaction to prepare the compound of formula (IV), the compound of formula (II) and the compound of formula (III) may be used in equimolar amounts and the base may be used in one or two equivalent amounts. The base may be an inorganic base, e.g., sodium hydride, potassium t-butoxide, sodium carbonate or potassium carbonate; or an organic base, e.g., triethyl amine or pyridine. The solvent which may be used in the reaction includes acetone, methyl ethyl ketone, benzene, toluene, tetrahydrofuran, acetonitrile, dichloromethane or dimethyl formamide, and the reaction may be conducted at a temperature ranging from room temperature to 100° C. The progress of the reaction is conveniently followed by measuring the disappearance of the compound of formula (II) with thin layer chromatography (TLC).

Examples of the compound of formula (IV) include the compounds of formulas (IV-a) (X=CH, $R^1$=H), (IV-b) (X=CH, $R^1$=CH$_3$), (IV-c) (X=CH, $R^1$=CF$_3$), (IV-d) (X=N, $R^1$=H), (IV-e) (X=N, $R^1$=CH$_3$) and (IV-f) (X=N, $R^1$=CF$_3$), depending on the starting materials used, i.e., depending on any one of the reactions of the compound of formula (II-a) or (II-b) with the compound of formula (III-a), (III-b) or (III-c):

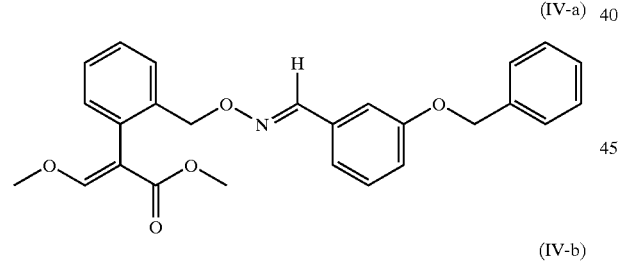

(IV-a)

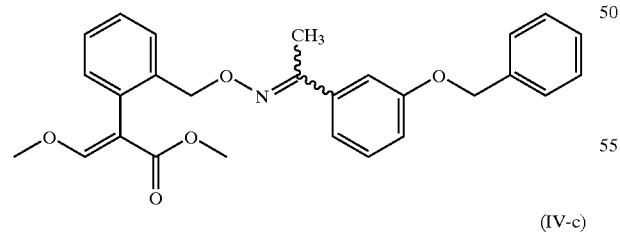

(IV-b)

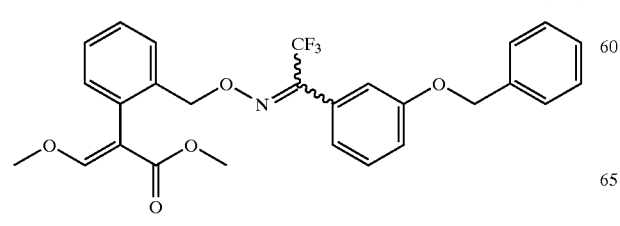

(IV-c)

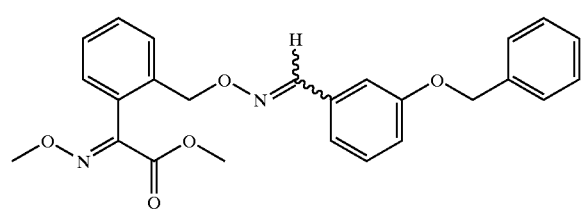

(IV-d)

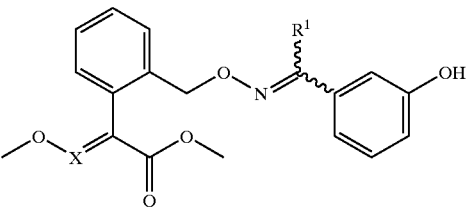

(IV-e)

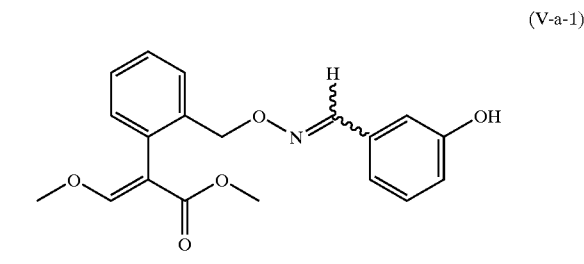

(IV-f)

Subsequently, the compound of formula (IV) is debenzylated by hydrogenolysis to obtain a phenolic ester compound of formula (V-a):

(V-a)

wherein, X and $R^1$ has the same meanings as defined previously.

Examples of the compound of formula (V-a) include the compounds of formulas (V-a-1) (X=CH, $R^1$=H), (V-a-2) (X=CH, $R^1$=CH$_3$), (V-a-3) (X=CH, $R^1$=CF$_3$), (V-a-4) (X=N, $R^1$=H), (V-a-5) (X=N, $R^1$=CH$_3$) and (V-a-6) (X=N, $R^1$=CF$_3$), which correspond 10 to the compounds of formulas (IV-a) to (IV-f), respectively:

(V-a-1)

(V-a-2)

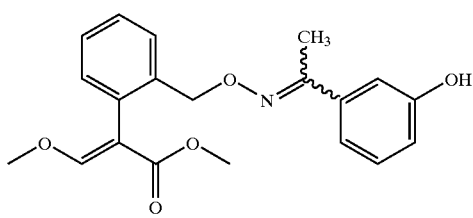

(V-a-3)

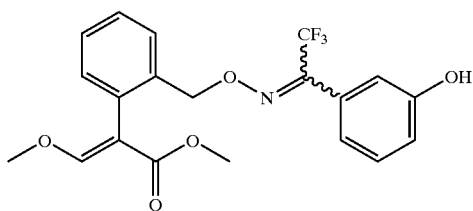

(V-a-4)

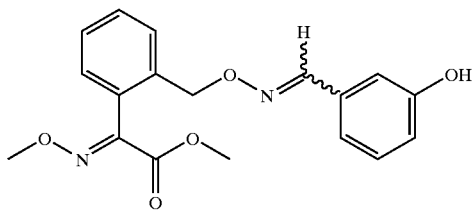

(V-a-5)

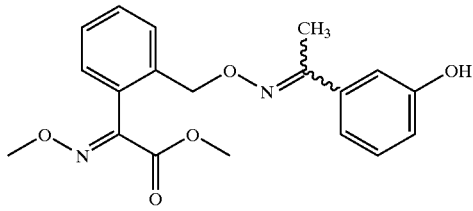

(V-a-6)

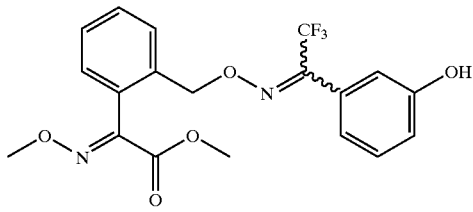

On the other hand, the compound of formula (VI) is inclusive of a compound of formula (VI-a), i.e., the compound of formula (VI) wherein $R^3$ is H, and a compound of formula (VI-b), i.e., the compound of formula (I) wherein $R^3$ is $CF_3$.

(VI-a)

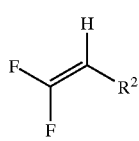

(VI-b)

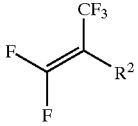

The compound of formula (VI-a) may be prepared by a Grignard reaction, reduction, halogenation and dehalogenation of a halide of $R^2$ according to a conventional method (Herkes, F. E. et al., J. Org. Chem., 32, 1311(1967); and Nemeth, G. et al., J. fluorine Chem., 76, 91(1996)), as shown in Reaction Scheme E:

Reaction Scheme E

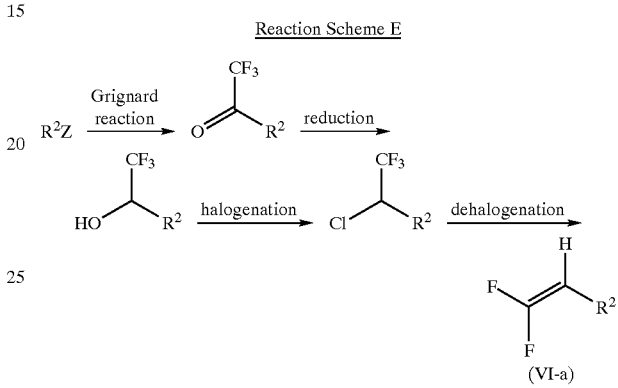

wherein, $R^2$ has the same meaning as defined in formula (I) above; and Z represents Cl or F.

Further, a compound of formula (VI-b) may be prepared by a Grignard reaction and Wittig reaction of a halide of $R^2$ according to a conventional method (Herkes, F. E. et al., *J. Org. Chem.*, 32, 1311(1967); and Wheatman. G. A. et al., *J. Org Chem.*, 48, 917(1983)), as shown in Reaction Scheme F:

Reaction Scheme F

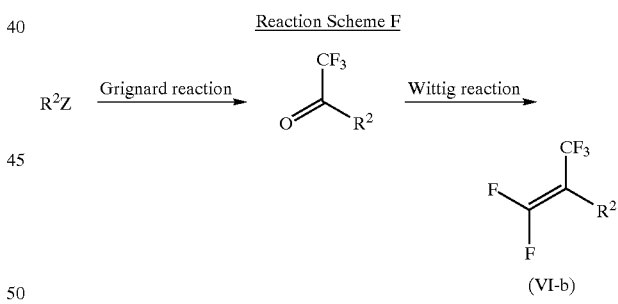

wherein, $R^2$ and Z have the same meanings as above.

In the step to prepare the compound of formula (I-a) of the present invention by reacting the compound of formula (V-a) with a compound of formula (VI) in the presence of a base, the compounds of formulas (V-a) and (VI) may be used in equimolar amounts and the base may be used in one to two equivalent amounts. The base may be an inorganic base, e.g., sodium hydride, potassium t-butoxide, sodium carbonate or potassium carbonate; or an organic base, e.g., triethyl amine or pyridine. The solvent, which may be used in the reaction, is benzene, toluene, tetrahydrofuran, acetonitrile, dichloromethane or dimethyl formamide, and the reaction temperature in the range of room temperature to 100° C.

In the preparation of the compound of formula (I-b) by reacting the phenolic ester compound of formula (V-a) with methylamine to obtain a phenolic amide compound of formula (V-b), in a conventional manner, and then reacting the compound of formula (V-b) with a compound of formula (VI) in the presence of a base, methylamine may be preferably employed in an excess amount than the phenolic ester compound used. The above reaction may be conducted in the presence of an alcohol (e.g., methanol), acetonitrile, dichloromethane and dimethyl formamide, at a temperature ranging from room temperature to the boiling point of the solvent used.

Examples of the compound of formula (V-b) are the compounds of formulas (V-b-1) (X=CH, $R^1$=H), (V-b-2) (X=CH, $R^1$=CH$_3$), (V-b-3) (X=CH, $R^1$=CF$_3$), (V-b-4) (X=N, $R^1$=H), (V-b-5) (X=N, $R^1$=CH$_3$) and (V-b-6) (X=N, $R^1$=CF$_3$), which correspond to the compounds of formulas (IV-a) to (IV-f), respectively:

(V-b-1)
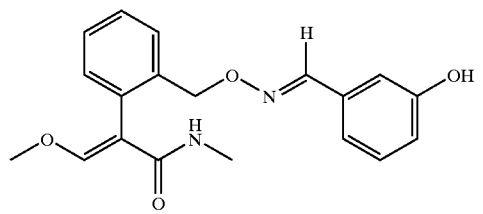

(V-b-2)
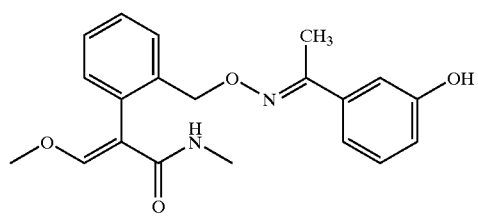

(V-b-3)
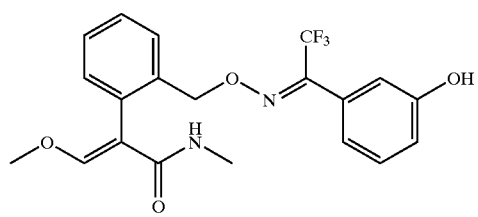

(V-b-4)
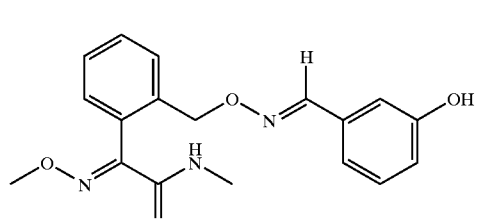

(V-b-5)
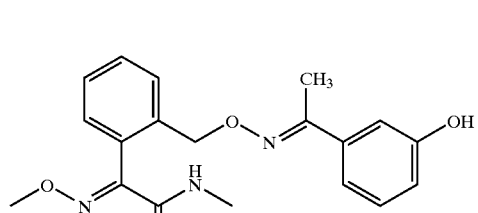

(V-b-6)
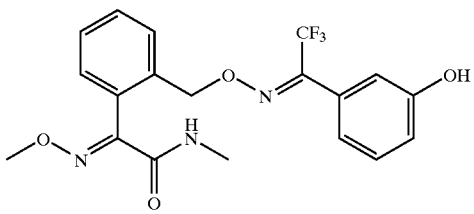

On the other hand, the compound of formula (I-a) may be prepared, as shown in the above Reaction Scheme A, by reacting a compound of formula (II) with a compound of formula (VII) in the presence of a base. At this time, the compound of formula (II) and the compound of formula (VII) may be used in equimolar amounts and the base may be used in one or two equivalent amounts. The base may be an inorganic base, e.g., sodium hydride, potassium t-butoxide, sodium carbonate or potassium carbonate; or an organic base, e.g., triethylamine or pyridine. The solvent which may be used in the reaction includes acetone, methyl ethyl ketone, benzene, toluene, tetrahydrofuran, acetonitrile, dichloromethane or dimethyl formamide, and the reaction may be conducted at a temperature ranging from room temperature to 100° C. The progress of the reaction is conveniently followed by measuring the disappearance of the compound of formula (II) with thin layer chromatography (TLC).

Further, the compound of formula (I-b) may be obtained by reacting the compound of formula (I-a) with methylamine in a conventional manner.

The compound of formula (VII) may be prepared by reaction of 3-hydroxybenzaldehyde, 3-hydroxyacetophenone or 3-hydroxy-2'2'2'-trifluoroacetophenone with a compound of formula (VI) to obtain a compound of formula (VIII) and condensation of the compound of formula (VIII) with hydroxylamine according to a conventional method (Lichtenhaler, F. W., et al., *Tetrahedron Lett.*, 1425(1980); and Sugg, E. E., et al., *J. Org. Chem.*, 50, 5032(1985)), as shown in Reaction Scheme G:

Reaction Scheme G

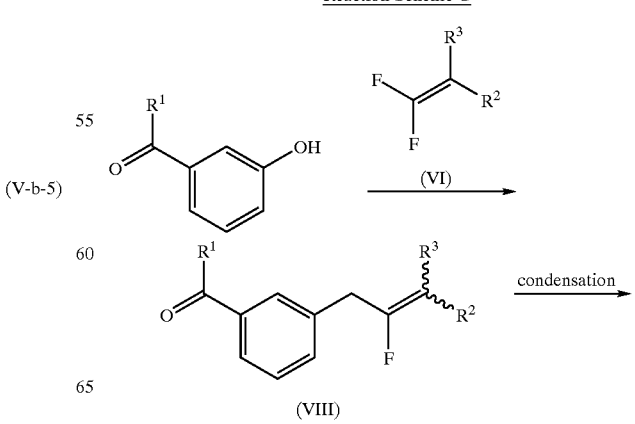

-continued

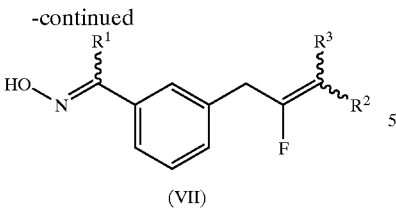

(VII)

wherein, $R^1$, $R^2$ and $R^3$ have the same meanings as defined in formula (I).

The compound of formula (VII) is inclusive of a compound of formula (VII-a), i.e., the compound of formula (VII) wherein $R^3$ is H, and a compound of formula (VII-b), i.e., the compound of formula (VII) wherein $R^3$ is $CF_3$, which correspond to the compounds of formulas (VI-a) and (VI-b) used as a starting material, respectively:

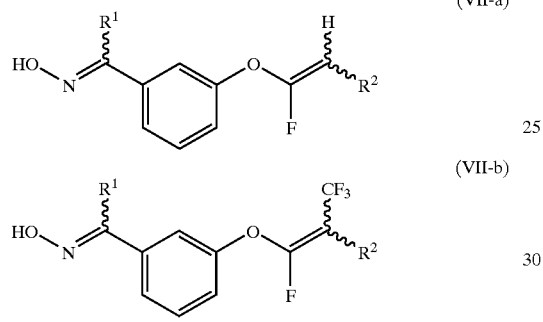

(VII-a)

(VII-b)

The compound of formula (I) of the present invention has three double bonds, and when one ignores the double bond of the bridging oxime group, there exist four stereoisomers thereof, which, according to the terminology defined in the Cahn-Ingold-Prelog system (J. March, Advanced Organic Chemistry, 3rd Ed., Wiley-Interscience), may be expressed as (E,E), (E,Z), (Z,E) and (Z,Z) isomers. which are included within the scope of the present invention.

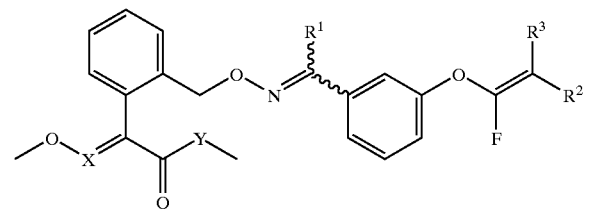

(when $R^3$ is H, (E,Z) isomer; and when $R^3$ is $CF_3$, (E,E) isomer)

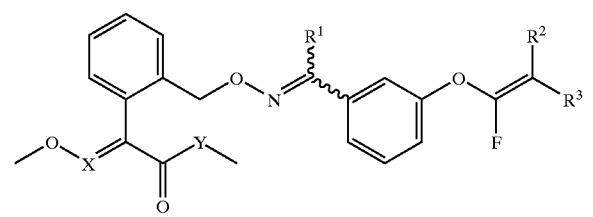

(when $R^3$ is H, (E,E) isomer; and when $R^3$ is $CF_3$, (E,Z) isomer)

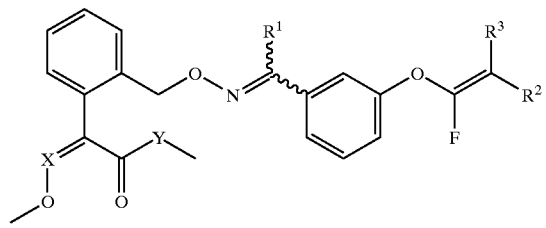

(when $R^3$ is H, (Z,Z) isomer; and when $R^3$ is $CF_3$, (Z,E) isomer)

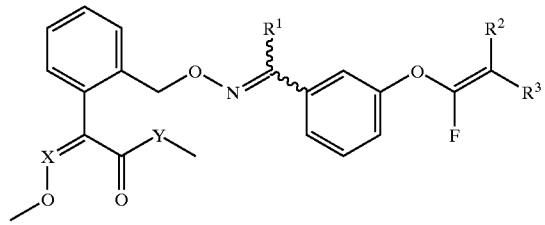

(when $R^3$ is H, (Z,E) isomer; and when $R^3$ is $CF_3$, (Z,Z) isomer)

wherein, X, Y, $R^1$, $R^2$ and $R^3$ have the same meanings as defined above.

In case a mixture of the E and Z isomers of the compound of formula (II) is used in the reaction shown in Reaction Scheme A, the compound of the present invention is obtained as a mixture of the above four isomers wherein the (E,E) and (E,Z) isomers predominate with minor amounts of the (Z,E) and (Z,Z) isomers.

However, in case only the E isomer of the compound of formula (II-a-4) or (II-b-4) is used, the compound of formula (I) of the present invention is obtained as a mixture of the (E,E ) and (E,Z) isomers, as is confirmed by $^1$H-NMR or $^{19}$F-NMR analysis.

According to the $^1$H-NMR analysis (reference compound, TMS) of the compound of formula (I) of the present invention wherein $R^3$ is hydrogen, a hydrogen of vinyl group of (E,E) isomer is shown as a doublet having a coupling constant of 5 to 6 Hz at 5.5 to 5.8 ppm, while that of (E,Z) isomer is represented as a doublet having a coupling constant of 30 Hz at 5.0 to 5.4 ppm. The ratio of the (E,E) isomer to (E,Z) isomer is about 2:1 which may be calculated from integration on the $^1$H-NMR spectroscopy. This result can be confirmed by the $^{19}$F-NMR analysis. The $^{19}$F-NMR analysis of the compound of the present invention wherein $R^3$ is hydrogen, the fluorine substituent on the vinyl group of the (E,E) isomer is shown as a doublet having a coupling constant of 5.5 Hz at −83.3 ppm, while that of the (E,Z) isomer is represented by a doublet having a coupling constant of 28.6 Hz at −83.1 ppm; and, the (E,E) to (E,Z) isomer ratio is also confirmed to be about 2:1 from integration on the $^{19}$F-NMR spectroscopy.

According to the $^{19}$F-NMR analysis data of the compound of formula (I) of the present invention wherein $R^3$ is $CF_3$, the vinyl fluorine and the fluorine of $CF_3$ of the (E,E) isomer are, respectively, a quartet having a coupling constant of 12.2 Hz at −75.9 ppm and a doublet having a coupling constant of 12.3 Hz at −58.7 ppm, while those of the (E,Z) isomer are, respectively, a quartet having a coupling constant of 23.9 Hz at −76.3 ppm and a doublet having a coupling constant of 24.7 Hz at −58.5 ppm. The (E,E) to (E,Z) isomer ratio is about 1:2 based on the integration of fluorine peaks.

The compound of the present invention has a broad spectrum of fungicidal activity against various plant pathogenic fungus, e.g. *Pyricularia oryzae* Carvara KA301 which causes Rice Blast, *Rhizoctonia solani* AG-1 which causes Rice Sheath Blight, *Botrytis cinerae* which causes Cucumber Gray Mold Rot, *Phytophthora infestans* which causes Tomato Late Blight, *Puccinia recondita* which causes Wheat Leaf Rust and *Erysiphe graminis* which causes Barley Powdery Mildew.

Accordingly, the present invention also includes within its scope fungicidal compositions comprising one or more of the compounds of formula (I) or stereoisomer thereof as an active ingredient, in association with fungicidally acceptable carriers.

The fungicidal compositions of the invention may be formulated in various forms such as an emulsion, aqueous dispersion, powder and granules which may contain conventional additives. The compound of the formula (I) may be used in an amount of 10 to 90% on the basis of the weight of an emulsion or aqueous dispersion, and 0.1 to 10% on the basis of the weight of granules.

Fungicidally acceptable carrier that may be used in the present invention is a liquid carrier, e.g., water, an alcohol (ethanol, ethylene glycol, glycerine), ketone(acetone, methylethylketone), ether(dioxane, tetrahydrofuran, cellosolve), aliphatic hydrocarbon(gasoline, Kerosene), halogenated hydrocarbon(chloroform, carbon tetrachloride), amide(dimethylformamide), ester(ethyl acetate, butyl acetate, fatty glycerine ester) and acetonitrile; and a solid carrier, e.g., mineral particle(Kaoline, clay, bentonite, dolomite, talc, silica, sand) and vegetable powder(shrubs).

The additive that may be used in the fungicidal composition of the present invention includes an emulsifier, adhesive, dispersion agent or permeating agent. e.g., nonionic, anionic or cationic interface active agent(fatty acid sodium salt, polyoxy alkyl ester, alkyl sulfonate ester). Further, an agrochemically active ingredient, e.g., an insecticide, herbicide, plant growth regulator, germicide, and fertilizer, may be added in the composition of the present invention.

The following Preparation and Examples are given for the purpose of illustration only and are not intended to limit the scope of the invention.

PREPARATION 1

Preparation of Methyl(2E)-3-ethoxy-2-(2'-bromomethyl)phenyl-2-propenoate (Compound of Formula (II-a))

Step 1: Preparation of Methyl o-Tolylacetate 30.0 g (0.2 mol) of o-tolyl acetic acid was dissolved in 100 ml of methanol, 5 ml of concentrated sulfuric acid was added thereto and the resulting solution was stirred with heating for 6 to 12 hours. The resulting solution was cooled and the solvent was removed under a reduced pressure to obtain a residue. The residue was washed twice with water and extracted with ethyl acetate. The organic layer was dried over magnesium sulfate and the solvent was removed under a reduced pressure. The residue thus obtained was subjected to column chromatography using a mixture of n-hexane and ethyl acetate (4:1) as an eluent to obtain 32.15 g (yield 98%) of the title compound as a colorless liquid.

$^1$H-NMR (CDCl$_3$, TMS) δ (ppm) 7.21–7.01 (m, 4H), 3.61 (s, 3H), 3.60 (s, 2H), 2.35 (s, 3H); MS (m/e): 164 (M+, 42), 133 (100), 31 (82).

Step 2: Preparation of Methyl 3-Hydroxy-2-(2'-methyl)phenyl-2-propenoate 24.6 g (0.15 mol) of the compound obtained in Step 1 and 24.3 g (0.45 mol) of sodium methoxide were added to 300 ml of toluene, and 27 g (0.45 mol) of methylformate was added dropwise thereto over a period of 1 hour while cooling and stirring. The resulting solution was stirred at room temperature for 12 hours and extracted twice or three times with water. The combined aqueous layer was acidified with concentrated hydrochloric acid and then extracted with ethyl acetate. The organic layer was dried over magnesium sulfate and then the solvent was removed under a reduced pressure to obtain a residue. The residue was subjected to column chromatography using a mixture of n-hexane and ethyl acetate (9:1) as an eluent to obtain 27.36 g (yield 95%) of the title compound as a colorless liquid.

$^1$H-NMR (CDCl$_3$, TMS) δ (ppm) 11.92 (d, 1H), 7.32–7.01 (m, 4H), 3.71 (s, 3H), 2.21 (s, 3H); MS (m/e): 192 (M+, 26), 160 (52), 132 (48), 84 (100).

Step 3: Preparation of Methyl 3-Methoxy-2-(2'-methyl)phenyl-2-propenoate 19.2 g (0.1 mol) of the compound obtained in Step 2, 15.12 g (0.12 mol) of dimethyl sulfate and 13.82 g (0.1 mol) of potassium carbonate were added to 200 ml of acetone, and the resulting solution was stirred for 12 hours with heating. The solvent was removed under a reduced pressure and the residue was extracted with ethyl acetate. The organic layer was dried over magnesium sulfate and the solvent was removed under a reduced pressure to obtain a residue. The residue was subjected to column chromatography using a mixture of n-hexane and ethyl acetate (4:1) as an eluent to obtain 17.1 g (yield 83%) of the title compound having two isomers as a colorless liquid.

The title compound thus obtained was composed of 82% E isomer and 18% Z isomer.

<E isomer (upper spot)>

$^1$H-NMR (CDCl$_3$, TMS) δ (ppm) 7.51 (s, 1H), 7.35–6.98 (m, 4H), 3.79 (s, 3H), 3.68 (s, 3H), 2.21 (s, 3H); MS (m/e): 206 (M$^+$, 10), 176 (73), 117 (100), 77 (57).

<Z isomer (down spot)>

$^1$H-NMR (CDCl$_3$, TMS) δ (ppm) 7.34–6.98 (m, 4H), 6.50 (s, 1H), 3.85 (s. 3H), 3.68 (s, 3H), 2.21 (s, 3H) MS (m/e): 206 (M$^+$, 8), 176 (100), 117 (92), 77 (30)

These isomers were separated and the E isomer was used in the following step.

Step 4: Preparation of Methyl (2E)-3-Methoxy-2-(2'-bromomethyl)phenyl-2-propenoate 18.54 g (0.09 mol) of methyl (2E)-3-methoxy-2-(2'-methyl)phenyl-2-propenoate obtained in Step 3 and 16.0 g (0.09 mol) of N-bromosuccinimide were added to 100 ml of carbon tetrachloride. Then, 0.16 g (1 mmol) of 2,2'-azo-bis-isobutyronitrile was added thereto, and the resulting solution was stirred for 12 hours with heating. The resultant solution was cooled and filtered to remove succinimide. The solvent was removed under a reduced pressure and an oily residue thus obtained was subjected to column chromatography using a mixture of n-hexane and ethyl acetate (4:1) as an eluent to obtain 21.73 g (yield 85%) of the title compound as a colorless solid.

Melting Point: 64–65° C.; $^1$H-NMR (CDCl$_3$, TMS) δ (ppm) 7.63 (s, 1H), 7.51–7.09 (m, 4H), 4.40 (s, 2H), 3.82 (s, 3H), 3.69 (s, 3H); MS (m/e): 284 (M$^+$, 10), 253 (12), 205 (21), 173 (38), 145 (100).

PREPARATION 2

Preparation of Methyl (2E)-2-Methoxyimino-2-(2'-bromomethyl)phenylacetate (Compound of Formula (II-b))

Step 1: Preparation of Methyl 2-Methylbenzoylformate 5.1 g (0.21 mol) of magnesium was placed in 300 ml of dry ether and 34.18 g (0.2 mol) of 2-bromotoluene was added dropwise thereto under a nitrogen atmosphere to prepare a Grignard reagent. The Grignard reagent solution was cooled to −78° C. and 23.6 g (0.2 mol) of dimethyl oxalate was added dropwise thereto. The resulting solution was stirred for 30 minutes, mixed with crushed ice, acidified with 20% hydrochloric acid and then extracted with ether. The organic layer was washed three times with water, dried over magnesium sulfate, and the solvent was removed under a reduced pressure to obtain a residue. The residue was subjected to column chromatography using a mixture of n-hexane and ethyl acetate (9:1) as an eluent to obtain 24.2 g (yield 68%) of the title compound as a colorless liquid.

$^1$H-NMR (CDCl$_3$, TMS) δ (ppm) 7.88–7.01 (m, 4H), 3.98 (s, 3H), 2.65 (s, 3H); MS (m/e): 178 (M$^+$, 21), 119 (100), 91 (71), 65 (37).

Step 2: Preparation of Methyl 2-Methoxyimino-2-(2'-methyl)phenylacetate 8.35 g (0.1 mol) of O-methylhydroxylamine hydrochloride and 8.1 ml (0.1 mol) of pyridine were added to 100 ml of methanol, and then, 17.8 g (0.1 mol) of the compound obtained in Step 1 was added thereto. The resulting solution was stirred for 12 hours with heating and concentrated under a reduced pressure. The resultant solution was mixed with water and extracted with ethyl acetate. The organic layer was dried over magnesium sulfate and the solvent was removed under a reduced pressure to obtain a residue. The residue was subjected to column chromatography using a mixture of n-hexane and ethyl acetate (4:1) as an eluent to obtain 19.04 g (yield 92%) of the title compound as a colorless liquid.

The title compound thus obtained was composed of 50% Z isomer and 50% E isomer. The Z isomer was a liquid and the E isomer was a solid obtained by recrystallization in n-hexane. The structure of E isomer was identified by X-ray crystallography.

<Z isomer(upper spot)>
$^1$H-NMR (CDCl$_3$, TMS) δ (ppm) 7.41–7.15 (m, 4H), 4.01 (s, 3H), 3.85 (s, 3H), 2.45 (s, 3H); MS (m/e): 207 (M$^+$, 8), 176 (41), 116 (100), 89 (62).

<E isomer(down spot)>
m.p.: 63–64° C.; $^1$H-NMR (CDCl$_3$, TMS) δ (ppm) 7.38–7.05 (m, 4H), 4.04 (s, 3H), 3.85 (s, 3H), 2.19 (s, 3H); MS (m/e): 207 (M$^+$, 11), 176 (82), 116 (100), 89 (70).

The E isomer was employed in following step.

Step 3: Preparation of Methyl (2E)-2-Methoxyimino-2-(2'-bromomethyl)phenylacetate 9.0 g (0.0435 mol) of methyl (2E)-2-methoxyimino-2-(2'-methyl)-phenylacetate obtained in Step 2 and 7.74 g (0.0435 mol) of N-bromosuccinimide were added to 50 ml of carbon tetrachloride, and then, 0.16 g (1 mmol) of 2,2'-azo-bis-isobutyronitrile was added thereto. The resulting solution was stirred for 12 hours with heating, solvent was removed under a reduced pressure and obtained an oily residue which was subjected to silica gel column chromatography using a mixture of n-hexane and ethyl acetate (4:1) as an eluent to obtain 11.08 g (yield 90%) of the title compound as a colorless liquid.

$^1$H-NMR (CDCl$_{13}$, TMS) δ (ppm) 7.62–7.01 (m, 4H), 4.39 (s, 2H), 4.04 (s, 3H), 3.85 (s, 3H); MS (m/e): 285 (M$^+$, 46), 252 (35), 175 (100), 146 (94), 116 (78).

PREPARATION 3

Preparation of 3-Benzyloxybenzaldoxime (Compound of Formula (III-a))

Step 1: Preparation of 3-Benzyloxybenzaldehyde 24.2 g (0.2 mol) of 3-hydroxybenzaldehyde and 25.32 g (0.2 mol) of benzyl chloride were placed in 500 ml of acetone and 21.2 g (0.2 mol) of sodium carbonate was added thereto. The resulting solution was stirred for 12 to 24 hours with heating, cooled to room temperature. The solvent was removed under a reduced pressure and the residue thus obtained was washed with water and the extracted with ethyl acetate twice. The organic layer was dried and the solvent was removed under a reduced pressure to obtain a residue. The residue was subjected to column chromatography using a mixture of n-hexane and ethyl acetate (9:1) as an eluent to obtain 35.6 g (yield 84%) of the title compound as a colorless liquid.

$^1$H-NMR (CDCl$_3$, TMS) δ (ppm) 10.01 (s, 1H), 7.67–7.18 (m, 9H), 5.14 (s, 2H); MS (m/e): 212 (MW, 32), 121 (73), 91 (100).

Step 2: Preparation of 3-Benzyloxybenzaldoxime 31.8 g (0.15 mol) of the compound obtained in Step 1 and 11.47 g (0.165 mol) of hydroxylamine hydrochloride were placed in 200 ml of methyl alcohol, and 13.35 ml (0.165 mol) of pyridine was added thereto. The resulting solution was refluxed for 1 hour, and then was mixed with water and extracted with ethyl acetate. The organic layer was dried over magnesium sulfate and the solvent was removed under a reduced pressure to obtain a white-colored residue. The residue was washed with 100 ml of n-hexane to obtain 30.3 g (yield 89%) of the title compound.

m.p.: 58–59° C.; $^1$H-NMR (CDCl$_3$, TMS) δ (ppm) 8.62 (b, 1H), 8.18 (s, 1H), 7.54–7.02 (m, 9H), 5.13 (s, 2H); MS (m/e): 227 (M$^+$, 32), 91 (100), 65 (45).

PREPARATIONS 4 AND 5

Preparation of 3-Benzyloxyphenylmethyloxime (Compound of Formula (III-b)) and 3-Benzyloxyphenyltrifluoromethyloxime (Compound of Formula (III-c))

The procedure of Preparation 3 was repeated except that 3-hydroxyphenyl methyl ketone and 3-hydroxyphenyl trifluoromethyl ketone were used in place of 3-hydroxybenzaldehyde, to obtain the title compounds.

The analysis data of the compounds prepared in Preparations 3 to 5 are listed in Table 1.

TABLE 1

| Prep. No. | R$^1$ | $^1$H-NMR(CDCl$_3$, TMS) δ (ppm) | Mass (m/e) (M, int.) | M.P. (° C.) | Yield (%) | Product |
| --- | --- | --- | --- | --- | --- | --- |
| 3 | H | 10,01(s, 1H), 7.67–7.18(m, 9H), 5.14(s, 2H) | 212(32), 121(73), 91(100) | — | 84 | Intermediate |
| 4 | CH$_3$ | 7.82–7.02(m, 9H), 5.14(s, 2H), 2.28(s, 3H) | 226(37), 135(63), 91(100) | — | 86 | |

TABLE 1-continued

| Prep. No. | R¹ | ¹H-NMR(CDCl₃, TMS) δ (ppm) | Mass (m/e) (M, int.) | M.P. (° C.) | Yield (%) | Product |
|---|---|---|---|---|---|---|
| 5 | $CF_3$ | 8.10–7.01(m, 9H), 5.15(s, 2H) | 280(42), 211(23), 91(100), 65(47) | — | 74 | |
| 3 | H | 8.62(b, 1H), 8.18(s, 1H), 7.54–7.02(m, 9H), 5.13(s, 2H) | 227(32), 91(100), 65(45) | 58–59 | 89 | Compound of formula (III) |
| 4 | $CH_3$ | 8.62(b, 1H), 7.51–6.96(m, 9H), 5.10(s, 2H), 2.29(s, 3H) | 241(35), 91(100), 65(45) | 61–62 | 84 | |
| 5 | $CF_3$ | 9.02(b, 1H), 7.61–6.94(m, 9H), 5.12(s, 2H) | 295(48), 91(100), 65(18) | 72–73 | 82 | |

PREPARATION 6

Preparation of Methyl (2E)-3-Methoxy-2-[2-(((3-benzyloxyphenyl)imino)oxy)methylphenyl]-propenoate (Compound of Formula (IV-a))

5.7 g (0.02 mol) of methyl (2E)-3-methoxy-2-(2'-bromomethyl)phenyl-2-propenoate and 4.54 g (0.02 mol) of 3-benyloxybenzaldoxime prepared in preparation 3 were placed in 50 ml of acetone and 2.76 g (0.02 mol) of potassium carbonate was added thereto. The resulting solution was refluxed for 24 hours and cooled to room temperature, and the solvent was removed under a reduced pressure. The residue thus obtained was mixed with water and extracted with ethyl acetate with three times. The organic layer was dried over magnesium sulfate and filtered. The filtrate was subjected to column chromatography using a mixture of n-hexane and ethyl acetate (4:1) as an eluent to obtain 5.86 g (yield 68%) of the title compound as a brown liquid.

¹H-NMR (CDCl₃, TMS) δ (ppm) 8.01 (s, 1H), 7.52 (s, 1H), 7.51–6.82 (m, 13H), 5.18 (s, 2H), 5.04 (s, 2H), 3.73 (s, 3H), 3.61 (s, 3H); MS (m/e): 431 (M⁺, 21), 205 (39), 189 (50), 145 (100), 91 (67).

PREPARATIONS 7 TO 11

Preparation of the Compounds of Formulas (IV-b) to (IV-f) as Intermediates

The procedure of Preparation 6 was repeated except that methyl (2E)-3-methoxy-2-(2'-bromomethyl)phenyl-2-propenoate obtained in Preparation 1 and methyl (2E)-2-methoxyimino-2-(2'-bromomethyl)phenylacetate obtained in Preparation 2, and the oxime compounds obtained in Preparations 3 to 5 to obtain the compounds of formulas (IV-b) to (IV-f) as intermediates.

The analysis data of the compounds prepared in Preparations 6 to 11 are listed in Table 2.

TABLE 2

| Prep. No. | X | R¹ | ¹H-NMR(CDCl₃, TMS)δ (ppm) | Mass(m/e)(M, int.) | Yield (%) |
|---|---|---|---|---|---|
| 6 | CH | H | 8.01(s, 1H), 7.52(s, 1H), 7.51–6.82(m, 13H), 5.18(s, 2H), 5.04(s, 2H), 3.73(s, 3H), 3.61(s, 3H) | 431(21), 205(39), 189(50), 145(100), 91(67) | 68 |
| 7 | CH | $CH_3$ | 7.59(s, 1H), 7.57–7.12(m, 13H), 5.17(s, 2H), 5.03(s, 2H), 3.79(s, 3H), 3.67(s, 3H), 2.20(s, 3H) | 445(37), 205(47), 189(37), 145(100), 91(87) | 64 |
| 8 | CH | $CF_3$ | 7.57(s, 1H), 7.48–7.01(m, 13H), 5.19(s, 2H), 5.01(s, 2H), 3.74(s, 3H), 3.62(s, 3H) | 499(33), 278(57), 205(76), 189(66), 145(100), 91(89) | 77 |
| 9 | N | H | 8.06(s, 1H), 7.55–6.99(m, 13H), 5.17(s, 2H), 5.09(s, 2H), 3.91(s, 3H), 3.71(s, 3H) | 432(27), 401(38), 227(51), 206(47), 84(100), 47(79) | 67 |
| 10 | N | $CH_3$ | 7.64–6.87(m, 13H), 5.16(s, 2H), 5.05(s, 2H), 3.92(s, 3H), 3.73(s, 3H), 2.14(s, 3H) | 446(31), 227(57), 206(53), 84(100) | 61 |
| 11 | N | $CF_3$ | 7.71–6.90(m, 13H), 5.18(s, 2H), 5.04(s, 2H), 3.91(s, 3H), 3.72(s, 3H) | 500(43), 278(51), 222(64), 107(100) | 72 |

PREPARATION 12

Preparation of Methyl (2E)-3-Methoxy-2-[2-(((3-hydroxyphenyl)imino)oxy)methylphenyl]-propenoate (Compound of Formula (V-a-1))

5.17 g (0.012 mol) of methyl (2E)-3-methoxy-2-[2-(((3-benzyloxyphenyl)imino)oxy)methylphenyl]-propenoate was dissolved in 50 ml of methyl alcohol, and a catalytic amount (25 mg, 0.01 mmol) of 5% palladium on activated carbon was added thereto. The resulting mixture was reacted with stirring for 6 hours under a hydrogen pressure in a hydrogenation reactor. The reaction mixture solution was filtered to remove the activated carbon components, and the solvent was removed under a reduced pressure. The residue thus obtained was subjected to column chromatography using a mixture of n-hexane and ethyl acetate (2:1) as an eluent to obtain 3.64 g (yield 89%) of the title compound as a brown liquid.

$^1$H-NMR (CDCl$_3$, TMS) δ (ppm) 8.02 (s, 1H), 7.54 (s, 1H), 7.53–6.84 (m, 8H), 5.18 (s, 2H), 6.48 (b, 1H), 5.14 (s, 2H), 3.78 (s, 3H), 3.67 (s, 3H); MS (m/e): 341 (M$^+$, 41), 250 (37), 189 (57), 145 (100), 103 (20).

PREPARATIONS 13 to 17

Preparation of the Compounds of Formulas (V-a-2) to (V-a-6) as Intermediates

The procedure of Preparation 12 was repeated using the intermediates obtained in Preparations 7 to 11 to obtain the phenolic ester compounds of formulas (V-a-2 to (V-a-6) as intermediates.

The analysis data of the compounds prepared in Preparations 12 to 17 are listed in Table 3.

dissolved in 50 ml of methyl alcohol, and 40 ml of 40% methylamine aqueous solution was added thereto. The resulting solution was stirred for 12 hours, and the solvent was removed under a reduced pressure. The residue thus obtained was extracted with ethyl acetate. The organic layer was dried and the solvent was removed under a reduced pressure. The residue thus obtained was subjected to column chromatography using a mixture of n-hexane and ethyl acetate (2:1) as an eluent to obtain 2.90 g (yield 85%) of the title compound as a brown liquid.

$^1$H-NMR (CDCl$_3$, TMS) δ (ppm) 8.01 (s, 1H), 7.55 (s, 1H), 7.54–6.88 m, 8H), 6.53 (b, 1H), 6.34 (b, 1H), 5.142 s, 2H), 3.81 (s, 3H), 2.79 (d, 3H); MS (m/e): 340 (M$^+$, 38), 188 (100), 144 (72).

TABLE 3

| Prep. No. | X | R$^1$ | $^1$H-NMR(CDCl$_3$, TMS)δ (ppm) | Mass(m/e)(M, int.) | Yield (%) |
|---|---|---|---|---|---|
| 12 | CH | H | 8.02(s, 1H), 7.54(s, 1H), 7.53–6.84(m, 8H), 6.48(b, 1H), 5.14(s, 2H), 3.78(s, 3H), 3.67(s, 3H) | 341(41), 250(37), 189(57), 145(100), 103(20) | 89 |
| 13 | CH | CH$_3$ | 7.59(s, 1H), 7.53–6.98(m, 8H), 5.71(b, 1H), 5.13(s, 2H), 3.79(s, 3H), 3.67(s, 3H), 2.19(s, 3H) | 355(33), 205(35), 189(37), 145(100), 134(69) | 83 |
| 14 | CH | CF$_3$ | 7.58(s, 1H), 7.54–6.81(m, 8H), 6.55(b, 1H), 5.16(s, 2H), 3.78(s, 3H), 3.66(s, 3H) | 409(31), 221(38), 205(62), 189(99), 145(100), 131(38) | 85 |
| 15 | N | H | 7.98(s, 1H), 7.56–6.77(m, 8H), 6.54(b, 1H), 5.11(s, 2H), 3.91(s, 3H), 3.72(s, 3H) | 342(32), 206(76), 138(100), 59(46) | 87 |
| 16 | N | CH$_3$ | 7.50–6.78(m, 8H), 6.55(b, 1H), 5.10(s, 2H), 3.99(s, 3H), 3.76(s, 3H), 2.14(s, 3H) | 356(43), 222(30), 131(75), 116(100), 59(42) | 87 |
| 17 | N | CF$_3$ | 7.61–6.81(m, 8H), 6.38(b, 1H), 5.12(s, 2H), 3.98(s, 3H), 3.77(s, 3H) | 410(37), 222(38), 206(33), 131(65), 116(100), 59(62) | 80 |

PREPARATION 18

Preparation of N-Methyl (2E)-3-Methoxy-2-[2-(((3-hydroxyphenyl)imino)oxy)methylphenyl]-propenamide (Compound of Formula (V-b-1))

3.41 g (0.01 mol) of methyl (2E)-3-methoxy-2-[2-(((3-hydroxyphenyl)imino)oxy)methylphenyl]-propenoate was

PREPARATIONS 19 TO 23

Preparation of the Compounds of Formulas (V-b-2) to (V-b6)

The procedure of Preparation 18 was repeated using the intermediates obtained in Preparations 13 to 17 to obtain the phenolic amide compounds of formulas (V-b-2 to (V-b-6) as intermediates.

The analysis data of the compounds prepared in Preparations 18 to 23 are listed in Table 4.

TABLE 4

| Prep. No. | X | R$^1$ | $^1$H-NMR(CDCl$_3$, TMS)δ (ppm) | Mass(m/e)(M, int.) | 수율 (%) |
|---|---|---|---|---|---|
| 18 | CH | H | 8.01(s, 1H), 7.55(s, 1H), 7.54–6.88(m, 8H), 6.53(b, 1H), 6.34(b, 1H), 5.12(s, 2H), 3.81(s, 3H), 2.79(d, 3H) | 340(38), 188(100), 144(72) | 85 |
| 19 | CH | CH$_3$ | 7.57(s, 1H), 7.56–6.38(m, 8H), 6.23(b, 1H), 5.12(s, 2H), 5.87(b, 1H), 5.17(s, 2H), 3.79(s, 3H), 2.83(d, 3H), 1.18(s, 3H) | 354(26), 188(100), 144(58), 65(49) | 87 |
| 20 | CH | CF$_3$ | 7.55(s, 1H), 7.54–6.88(m, 8H), 6.27(b, 1H), 5.12(s, 2H), 5.37 (b, 1H), 5.13(s, 2H), 3.80(s, 3H), 2.86(d, 3H) | 408(37), 188(100), 144(64) | 83 |
| 21 | N | H | 8.00(s, 1H), 7.57–7.08(m, 8H), 6.74(b, 1H), 6.48(b, 1H), 5.12(s, 2H), 5.09(s, 2H), 3.93(s, 3H), 2.86(d, 3H) | 341(44), 241(37), 222(870), 132(63), 58(100) | 84 |
| 22 | N | CH$_3$ | 7.58–7.01(m, 8H), 6.82(b, 1H), 6.54(b, 1H), 5.12(s, 2H), 5.08 (s, 2H), 3.95(s, 3H), 2.81(d, 3H), 2.13(s, 3H) | 355(51), 221(50), 132(82), 116(99), 58(100) | 87 |
| 23 | N | CF$_3$ | 7.64–6.92(m, 8H), 6.80(b, 1H), 6.42(b, 1H), 5.12(s, 2H), 5.10 (s, 2H), 3.83(s, 3H), 2.84(d, 3H) | 409(42), 379(64), 321(100), 132(78), 88(62) | 86 |

PREPARATION 24

Preparation of 2,2-Difluorostyrene (Compound of Formula (VI-a))

Step 1: Preparation of 2,2,2-Trifluoromethyl Phenyl Ketone 5.1 g of magnesium(0.21 mol) was placed in 300 ml of dry diethyl ether and 31.4 g of bromobenzene (0.2 mol) was added dropwise thereto under a nitrogen atmosphere to prepare a Grignard reagent. The Grignard reagent solution was cooled to −78° C. and 28.4 g of ethyl trifluoroacetate (0.2 mol) was added dropwise thereto. The resulting solution was stirred for 1 hour, mixed with an crushed ice, acidified with a concentrated hydrochloric acid and then extracted three times with diethyl ether. The organic layer was dried over magnesium sulfate and the solvent was removed under a reduced pressure to obtain a residue. The residue was distilled at 64 to 65° C./33 mmHg to obtain 24.74 g (yield 71%) of the title compound as a colorless oil.

$^1$H-NMR (CDCl$_3$, TMS) δ (ppm) 7.52–7.12 (m, 5H); MS (m/e): 174 (M$^+$, 21), 105 (100), 77 (82), 69 (54).

Step 2: Preparation of 1-Hydroxy-2,2,2-trifluoroethylbenzene 12.2 g (0.07 mol) of compound obtained in Step 1 was dissolved in 150 ml of methanol and 1.32 g (0.035 mol) of sodium borohydride was added dropwise thereto for 30 minutes. The resulting solution was stirred at room temperature for 2 hours and the solvent was removed. Ethyl acetate was added thereto and the resultant solution was washed three times with water. The organic layer was dried over magnesium sulfate and the solvent was removed under a reduced pressure to obtain a residue. The residue was was distilled at 50 to 51° C./1 mmHg to obtain 12.07 g (yield 98%) of the title compound as a colorless liquid.

$^1$H-NMR (CDCl$_3$, TMS) δ (ppm) 7.54–7.13 (m, 5H), 4.87 (q, 1H), 4.29 (brs, 1H); MS (m/e): 176 (M$^+$, 39), 107 (26), 79 (91).

Step 3: Preparation of 1-Chloro-2,2,2-trifluoroethylbenzene 11.97 g (0.068 mol) of the compound obtained in Step 2 and 83 g (0.7 mol) of thionyl chloride were added to 100 ml of toluene and the mixture was stirred with heating for 12 hours. The resulting solution was cooled and washed with water. The organic layer was dried over magnesium sulfate and the solvent was removed under a reduced pressure to obtain a residue. The residue was subjected to silica gel column chromatography using n-hexane as an eluent to obtain 9.9 g (yield 72%) of the title compound as a colorless liquid.

$^1$H-NMR (CDCl$_3$, TMS) δ (ppm) 7.62–7.15 (m, 5H), 5.10 (q, 1H); MS (m/e): 194 (M$^+$, 94), 125 (100), 83 (30), 44 (81).

Step 4: Preparation of 2,2-Difluorostyrene 9.7 g (0.05 mol) of the compound obtained in Step 3 was dissolved in 50 ml of dry tetrahydrofuran, and then, 3.27 g (0.05 mol) of activated zinc was added thereto. The resulting solution was refluxed for 12 hours while stirring and heating. The resulting solution was cooled and filtered to remove precipitated salts. The solvent was removed under a reduced pressure and the residue was distilled at 58 to 59° C./49 mmHg to obtain 6.09 g (yield 87%) of the title compound as a colorless oil.

$^1$H-NMR (CDCl$_3$, TMS) δ (ppm) 7.45–7.10 (m, 5H), 5.20 (dd, 1H, J=26 Hz, J=4 Hz); MS (m/e): 140 (M$^+$, 100), 120 (26), 84 (16), 44 (32).

PREPARATIONS 25 to 40

The procedure of Preparation 24 was repeated to obtain various fluorinated vinyl compounds of formula (VI-a). The $^1$H-NMR and MS analysis data of the compounds obtained in Preparations 24 to 40 are shown in the following Table 5.

TABLE 5

Substituted 2,2-difluorostyrene

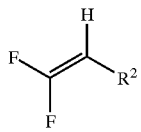

(VI-a)

| Prep. No. | R$^2$ | $^1$H-NMR(CDCl$_3$, TMS) δ (ppm) | MS (m/e) (m/e) (M, int) | Yield (%) | Boiling Point (mmHg) |
|---|---|---|---|---|---|
| 24 | C$_6$H$_5$— | 7.45–7.10(m, 5H), 5.20(dd, 1H, J=26Hz, 4Hz) | 140 (100), 120 (26), 84 (16), 44 (32) | 87 | 58–59 (49) |
| 25 | 3-CH$_3$—C$_6$H$_4$— | 7.48–6.92(m, 4H), 5.21(dd, 1H, J=26Hz, 4Hz), 2.28(s, 3H) | 154(39), 135 (29), 64 (41), 45 (100) | 87 | Column |
| 26 | 4-CH$_3$—C$_6$H$_4$— | 7.45–6.89(m, 4H), 5.26(dd, 1H, J=26Hz, 4Hz), 2.27(s, 3H) | 154 (100), 135 (62), 45 (54) | 86 | Column |
| 27 | 4-C$_2$H$_5$—C$_6$H$_4$— | 7.39–7.06(m, 4H), 5.25(dd, 1H, J=26Hz, 4Hz), 2.62(q, 2H), 1.21(t, 3H) | 168 (33), 153 (100), 133 (25), 84 (34) | 75 | Column |
| 28 | 4-n-C$_4$H$_9$—C$_6$H$_4$— | 7.24–7.10(m, 4H), 5,20(dd, 1H, J=26Hz, 4Hz), 2.54(t, 2H), 1.62–1.21(m, 4H), 0.92(t, 3H) | 196 (100), 177 (64), 158 (32) | 77 | Column |
| 29 | 3,4-(CH$_3$)$_2$—C$_6$H$_3$— | 7.32–7.02(m, 3H), 5.27(dd, 1H, J=26Hz, 4Hz), 2.22(s, 6H) | 168 (32), 133 (49), 44 (100) | 91 | Column |
| 30 | 3,5-(CH$_3$)$_2$—C$_6$H$_3$— | 7.01–6.89(m, 3H), 5.20(dd, 1H, J=26Hz, 4Hz), 2.24(s, 6H) | 168 (82), 153 (46), 84 (100), 62 (59) | 98 | Column |
| 31 | 3-CH$_3$O—C$_6$H$_4$— | 7.50–6.69(m, 4H), 5.19(dd, 1H, J=26Hz, 4Hz), 3.79(s, 3H) | 170 (100), 140 (36), 127 (42), 77 (24) | 98 | 33–34(1) |
| 32 | 4-CH$_3$O—C$_6$H$_4$— | 7.51–6.69(m, 4H), 5.29(dd, 1H, J=26Hz, 4Hz), 3.86(s, 3H) | 170 (100), 155 (68), 127 (92), 84 (21) | 80 | Column |
| 33 | 4-C$_2$H$_5$O—C$_6$H$_4$— | 7.49–6.81(m, 4H), 5.26(dd, 1H, J=26Hz, 4Hz), 4.10(q, 2H), | 184 (82), 127 (100), 53 (40) | 79 | Column |
| 34 | 3,4-OCH$_2$O—C$_6$H$_3$— | 7.81–7.28(m, 3H), 6.08(s, 2H), 5.27(dd, 1H, J=26Hz, 4Hz) | 184 (48), 165 (100), 146 (39) | 83 | column |
| 35 | 3-Cl—C$_6$H$_4$— | 7.36–7.12(m, 4H), 5.26(dd, 1H, J=26Hz, 4Hz) | 174 (94), 119 (38), 84 (100), 48 (93) | 95 | column |

TABLE 5-continued

Substituted 2,2-difluorostyrene (VI-a)

| Prep. No. | $R^2$ | $^1$H-NMR(CDCl$_3$, TMS) δ (ppm) | MS (m/e) (m/e) (M, int) | Yield (%) | Boiling Point (mmHg) |
|---|---|---|---|---|---|
| 36 | 4-Cl—C$_6$H$_4$— | 7.48–7.29(m, 4H), 5.23(dd, 1H, J=26Hz, 4Hz) | 174 (58), 139 (36), 119 (29), 84 (100), 49 (56) | 81 | column |
| 37 | 3-F—C$_6$H$_4$— | 7.59–6.78(m, 4H), 5.21(dd, 1H, J=26Hz, 4Hz) | 158 (21), 84 (100), 47 (42) | 75 | column |
| 38 | 4-F—C$_6$H$_4$— | 7.76–6.91(m, 4H), 5.25(dd, 1H, J =26Hz, 4Hz) | 158 (100), 39 (27) | 88 | column |
| 39 | 3-CH$_3$-4-Cl—C$_6$H$_3$— | 7.34–7.02(m, 3H), 5.24(dd, 1H, J=26Hz, 4Hz), 2.34(s, 3H) | 188 (100), 153 (71), 133 (30) | 87 | column |
| 40 | (naphthalen-2-yl) C$_{10}$H$_7$-2-yl- | 8.13–7.45(m, 7H), 5.81(dd, 1H, J=26Hz, 4Hz) | 190 (89), 170 (100), 138 (28), 85 (44) | 90 | column |

PREPARATION 41

Preparation of 2,2-Difluoro-1-trifluoromethylstyrene (Compound of Formula (VI-b))

26.2 g (0.1 mol) of triphenylphosphine was dissolved in 100 ml of dry tetrahydrofuran and 25.2 g (0.12 mol) of dibromodifluoro-methane was added dropwise thereto under a nitrogen atmosphere at a temperature below 10° C. The resulting solution was stirred for 30 minutes and thereto was added 8.71 g (0.05 mol) of the compound obtained in Step 1 of Preparation 24. The resultant solution was refluxed with heating for 48 hours, cooled and distilled under a reduced pressure. The obtained oil was redistilled at a temperature of 51 to 52° C./44 mmHg to obtain 7.07 g (yield 68%) of the title compound as a colorless liquid.

$^1$H-NMR (CDCl$_3$, TMS) δ (ppm) 7.59–7.31 (m, 5H) 3.79 (s, 3H); MS (m/e): 208 (M$^+$, 48), 84 (83), 43 (100).

PREPARATIONS 42 to 59

The procedure of Preparation 41 was repeated using corresponding halides in place of 4-bromobenzene to obtain various compounds of formula (VI-b). The $^1$H-NMR and MS data of these compounds are listed in Table 6.

TABLE 6

Substituted 2,2-difluoro-1-trifluoromethylstyrene (VI-b)

| Prep. No. | $R^2$ | $^1$H-NMR(CDCl$_3$, TMS) δ (ppm) | MS (m/e) (m/e) (M, int) | Yield (%) | Boiling Point (mmHg) |
|---|---|---|---|---|---|
| 41 | C$_6$H$_5$— | 7.59–7.31(m, 5H) | 208 (48), 84 (83), 43 (100) | 68 | 51–52 (44) |
| 42 | 3-CH$_3$—C$_6$H$_4$— | 7.46–6.98(m, 4H), 2.43(s, 3H) | 222 (20), 203 (70), 134 (100) | 45 | column |
| 43 | 4-CH$_3$—C$_6$H$_4$— | 7.32–7.18(m, 4H), 2.45(s, 3H) | 222 (64), 203 (23), 134 (100) | 62 | column |
| 44 | 4-C$_2$H$_5$—C$_6$H4— | 7.38–7.25(m, 4H), 2.68(q, 2H), 1.19(t, 3H) | 236 (20), 145 (100), 90 (54) | 62 | column |
| 45 | 4-n-C$_4$H$_9$—C$_6$H$_4$— | 7.32–7.25(m, 4H), 2.69(t, 2H), 2.01–1.23(m, 4H), 1.09(t, 3H) | 264 (30), 221 (37), 151 (36), 84 (100), 57 (50) | 58 | column |
| 46 | 3,4-(CH$_3$)$_2$—C$_6$H$_3$— | 7.28–7.02(m, 3H), 2.38(s, 3H), 2.32(s, 3H) | 236 (18), 84 (33), 45 (100) | 78 | column |
| 47 | 3,5-(CH$_3$)$_2$—C$_6$H$_3$— | 7.32–7.12(m, 3H), 2.41(s, 6H) | 236 (29), 217 (68), 148 (100), 45 (92) | 98 | column |
| 48 | 3-CF$_3$—C$_6$H$_4$— | 7.82–7.18(m, 4H) | 276 (52), 257 (92), 188 (100) | 52 | column |
| 49 | 4-CF$_3$—C$_6$H$_4$— | 7.81–7.42(m, 4H) | 276 (42), 257 (78), 188 (95), 107 (100) | 64 | column |

TABLE 6-continued

Substituted 2,2-difluoro-1-trifluoromethylstyrene

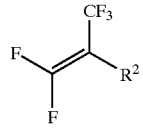

(VI-b)

| Prep. No. | R² | ¹H-NMR(CDCl₃, TMS) δ (ppm) | MS (m/e) (m/e) (M, int) | Yield (%) | Boiling Point (mmHg) |
|---|---|---|---|---|---|
| 50 | 3-CH₃O—C₆H₄— | 7.48–6.87(m, 4H), 3.81(s, 3H) | 238 (42), 207 (45), 139 (100), 69 (94) | 54 | 75 (10) |
| 51 | 4-CH₃O—C₆4— | 7.48–6.79(m, 4H), 3.79(s, 3H) | 238 (69), 195 (14), 145 (35), 74 (33) 59 (100) | 79 | 72–74 (10) |
| 52 | 4-C₂H₅O—C₆H₄— | 7.51–6.85(m, 4H), 4.12(q, 2H), 1.29(t, 3H) | 252 (47), 233 (100), 84 (64) | 73 | column |
| 53 | 3,4-OCH₂O—C₆H₃— | 7.01–6.79(m, 3H), 6.01(s, 2H) | 252 (46), 233 (63), 164 (82), 69 (100) | 72 | column |
| 54 | 3-Cl—C₆H₄— | 7.54–7.23(m, 4H) | 242 (26), 223 (72), 188 (49), 69 (100) | 63 | column |
| 55 | 4-Cl—C₆H₄— | 7.56–7.21(m, 4H) | 242 (35), 174 (70), 139 (100), 69 (79) | 45 | 58 (10) |
| 56 | 3-F—C₆H₄— | 7.53–6.96(m, 4H) | 226 (52), 207 (25), 84 (100) | 54 | column |
| 57 | 4-F—C₆4— | 7.52–6.83(m, 4H) | 226 (20), 84 (100) | 63 | column |
| 58 | 4-Br—C₆H₄— | 7.81–7.19(m, 4H) | 286 (100), 207 (86), 138 (66), 69 (57) | 43 | column |
| 59 | 3,5-Cl₂—C₆H₃— | 7.57–7.19(m, 3H) | 276 (100), 241 (45) | 84 | 85 (10) |

PREPARATION 60

Preparation of 1-[3-(1-Fluoro-2-phenyl)ethenyloxy] phenylmethyl Oxime (Compound of Formula (VII-a))

Step 1: Preparation of 1-[3-(1-Fluoro-2-phenyl)ethenyloxy]phenyl-2-ethanone

In a dried vessel, 68 g (0.5 mol) of 3-hydroxyacetophenone was added to 400 ml of methylethylketone and thereto was added 83 g of potassium carbonate (0.6 mol). The resulting solution was stirred for 30 minutes and 70 g (0.5 mol) of 2,2-difluorostyrene obtained in Preparation 24 was added slowly thereto. The resultant solution was stirred for 24 hours with heating and filtered to remove solids. The filtrate was concentrated, and the residue was washed with water and extracted with ethyl acetate. The organic layer was dried over magnesium sulfate and the solvent was removed under a reduced pressure. The residue was distilled at 188 to 190° C./1 mmHg to obtain 118.5 g (yield 92%) of the title compound as a colorless liquid.

¹H-NMR (CDCl₃, TMS) δ (ppm) 7.77–7.15 (m, 9H), 5.75 (d, 0.8H(E)), 5.38 (d, 0.2H(Z)), 2.59 (s, 3H); MS (m/e): 256 (M⁺, 100), 165 (27), 109 (62), 91 (32), 43 (72).

Step 2: Preparation of 1-[3-(1-Fluoro-2-phenyl)-ethenyloxy]phenylmethyloxime 76.8 g (0.3 mol) of the compound obtained in Step 1 above and 22.2 g (0.32 mol) of hydroxylamine hydrochloride were added to 500 ml of methanol, and thereto was added 25.9 ml (0.32 mol) of pyridine. The resulting solution was stirred at room temperature for 30 minutes and concentrated to remove the solvent. The residue was mixed with water and extracted with ethyl acetate. The organic layer was dried over magnesium sulfate and the solvent was removed under a reduced pressure. The residue was was subjected to silica gel column chromatography using a mixture of n-hexane and ethyl acetate (4:1) as an eluent to obtain 76.4 g (yield 94%) of the title compound as a colorless liquid.

¹H-NMR (CDCl₃, TMS) δ (ppm) 8.26 (br.s, 1H), 7.46–7.16 (m, 9H), 5.74 (d, 0.8H(E)), 5.37 (d, 0.2H(Z)), 2.29 (s, 3H); MS (m/e): 271 (M⁺, 100), 118 (42), 109 (41), 90 (22).

PREPARATION 61

Preparation of 1-[3-(1,3,3,3-Tetrafluoro-2-phenyl)-1-propenyloxy]phenylmethyloxime (Compound of Formula (VII-b))

The procedure of Preparation 60 was repeated using 2,2-difluoro-1-trifluoromethylstyrene obtained in Preparation 41, in place of 2,2-difluorostyrene, to obtain the title compound as a colorless liquid.

¹H-NMR (CDCl₃, TMS) δ (ppm) 8.44 (br.s, 1H), 7.51–6.99 (m, 9H), 2.25 (s, 3H); MS (m/e): 339 (M⁺, 100), 186 (37), 134 (40), 117 (26), 89 (36).

EXAMPLE 1

Preparation of Methyl (2E)-3-Methoxy-2-{2'-[[[3"-(1'''-fluoro-2'''-phenyl-1'''-ethenyloxy)phenyl]imino]oxy]methylphenyl}propenoate (Compound 1)

341 mg (1 mmol) of the compound obtained in Preparation 12 was added to 10 ml of acetonitrile and 40 mg of sodium hydride (1 mmol) dispersed in mineral oil(60%) was added thereto under a nitrogen atmosphere. The resulting solution was stirred for 30 minutes and 140 mg (1 mmol) of the compound obtained in Preparation 24 was added slowly thereto, The resultant solution was stirred for 4 hours with heating, mixed with water and extracted with ethyl acetate. The organic layer was dried over magnesium sulfate and the solvent was removed under a reduced pressure. The residue was subjected to silica gel column chromatography using a mixture of n-hexane and ethyl acetate (4:1) as an eluent to obtain 420 mg (yield 91%) of the title compound as a colorless liquid.

¹H-NMR (CDCl₃, TMS) δ (ppm) 8.04 (s, 1H), 7.58 (s, 1H), 7.50–7.08 (m, 13H), 5.68 (d, 1H), 5.09 (s, 2H), 3.79 (s, 3H), 3.65 (s, 3H); ¹⁹F-NMR (CDCl₃, CFCl₃) δ (ppm): −83.066 (d, 1F, J=28.614 Hz, Z isomer), −83.344 (d, 1F, J=5.55 Hz, E-isomer); MS(m/e): 461 (M⁺, 48), 205 (33), 189 (63), 145 (100), 103 (15).

EXAMPLE 16

Preparation of N-Methyl (2E)-3-Methoxy-2-{2'-[[[3"-(1'''-fluoro-2'''-phenyl-1'''-ethenyloxy)phenyl]imino]oxy]methylphenyl}propenamide (Compound 16)

170 mg (0.5 mmol) of the compound obtained in Preparation 18 was added to 10 ml of acetonitrile and 40 mg of sodium hydride (1 mmol) dispersed in mineral oil (60%) was added thereto under a nitrogen atmosphere. The resulting solution was stirred for 30 minutes and 70 mg (0.5 mmol) of the compound obtained in Preparation 24 was added slowly thereto. The resultant solution was stirred for 4 hours with heating, mixed with water and extracted with ethyl acetate. The organic layer was dried over magnesium sulfate and the solvent was removed under a reduced pressure. The residue was subjected to silica gel column chromatography using a mixture of n-hexane and ethyl acetate (4:1) as an eluent to obtain 221 mg (yield 96%) of the title compound as a colorless liquid.

¹H-NMR (CDCl₃, TMS) δ (ppm) 8.07 (s, 1H), 7.61 (s, 1H), 7.59–6.89 (m, 13H), 5.71 (d, 1H), 5.17 (s, 2H), 4.14 (br, 1H), 3.64 (s, 3H), 2.96 (d, 3H); MS(m/e): 460 (M⁺, 28), 188 (100). 149 (53).

EXAMPLE 40

Preparation of Methyl (2E)-3-Methoxy-2-{2'-[[[3"-(1'''-fluoro-2'''-phenyl-1'''-ethenyloxy)phenyl]methylimino]oxy]methylphenyl}propenoate (Compound 40)

28.4 g (0.1 mol) of methyl (2E)-3-methoxy-2-(2'-bromomethyl)phenyl-2-propenoate obtained in Preparation 1 (the compound of formula (II-a)) and 27.1 g (0.1 mol) of the compound obtained in Preparation 60 (the compound of formula (VII-a)) were added to 200 ml of acetone, and thereto was added 13.8 g (0.1 mol) of potassium carbonate. The resulting solution was stirred for 24 hours with heating, and cooled to room temperature. The solvent was removed under a reduced pressure, and the residue was mixed with water and extracted three times with 50 ml of ethyl acetate. The organic layer was dried over magnesium sulfate and filtered. The filtrate was concentrated and the residue was subjected to silica gel column chromatography using a mixture of n-hexane and ethyl acetate (9:1) as an eluent to obtain 33.8 g (yield 71%) of the title compound as a colorless liquid.

¹H-NMR (CDCl₃, TMS) δ (ppm) 7.48 (s, 1H), 7.42–6.87 (m, 13H), 5.67 (d, 1H), 5.20 (s, 2H), 3.78 (s, 3H), 3.65 (s, 3H), 2.24 (s, 3H); MS (m/e): 475 (M⁺, 11), 205 (35), 189 (17), 145 (100), 109 (31).

EXAMPLE 64

Preparation of Methyl (2E)-2-Methoxyimino-2-{2'-[[[3"-(1'''-fluoro-2'''-phenyl-1'''-ethenyloxy)phenyl]methylimino]oxy]methylphenylacetate (Compound 64)

The procedure of Example 40 was repeated using methyl (2E)-2-methoxyimino-2-(2'-bromomethyl)phenylacetate obtained in Preparation 2, in place of the compound obtained in Preparation 1, to obtain the title compound as a colorless liquid.

¹H-NMR (CDCl₃, TMS) δ (ppm) 7.49–7.16 (m, 13H), 5.73 (d, 1H), 5.15 (s, 2H), 4.04 (s, 3H), 3.82 (s, 3H), 2.21 (s, 3H); MS (m/e): 476 (M⁺, 11), 131 (68), 116 (100), 59 (44).

EXAMPLE 77

Preparation of N-Methyl (2E)-2-Methoxyimino-2-{2'-[[[3"-(1'''-fluoro-2'''-phenyl-1'''-ethenyloxy)phenyl]methylimino]oxy]methylphenylacetamide (Compound 77)

The procedure of Preparation 18 was repeated using Compound 64 obtained in Example 64, in place of the propenoate compound, to obtain the title compound as a colorless liquid.

¹H-NMR (CDCl₃, TMS) δ (ppm) 7.47–7.15 (m, 13H), 6.71 (b, 1H), 5.70 (d, 1H), 5.13 (s, 2H), 3.93 (s, 3H), 2.84 (s, 3H), 2.18 (s, 3H); MS (m/e): 475 (M⁺, 11), 132 (50). 116 (68), 58 (100).

The procedure of Example 1 or 16 was repeated using corresponding phenolic ester compounds or phenolic amide comounds of formula (V) and fluorinated vinyl comounds of formula (VI-a), or, alternatively, the procedure of Example 40, 64 or 77 was repeated using corresponding bromide compounds of formula (II) and olefin substituted oxime compounds of formula (VII-a), to obtain various compounds of formula (I), as listed in Table 7.

TABLE 7

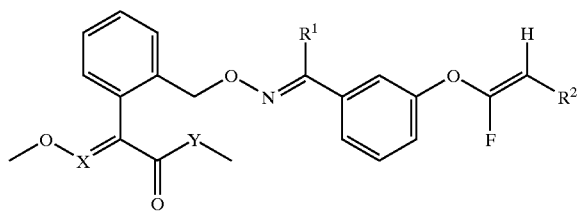

| Ex. No. | X | Y | R¹ | R² | ¹H-NMR(CDCl₃, TMS)δ (ppm) | MS (m/e) (M, int) |
|---|---|---|---|---|---|---|
| 1 | CH | O | H | C₆H₅ | 8.04(s, 1H), 7.58(s, 1H), 7.50~7.08(m, 13H), 5.68(d, 1H), 5.09(s, 2H), 3.79(s, 3H), 3.65(s, 3H) | 461 (48), 205 (33), 189 (63), 145 (100), 103 (15) |

TABLE 7-continued

| Ex. No. | X | Y | R¹ | R² | ¹H-NMR(CDCl₃, TMS)δ (ppm) | MS (m/e) (M, int) |
|---|---|---|---|---|---|---|
| 2 | CH | O | H | 3-CH₃—C₆H₄ | 8.04(s, 1H), 7.58(s, 1H), 7.52~6.97(m, 12H), 5.68(d, 1H), 5.10(s, 2H), 3.78(s, 3H), 3.64(s, 3H), 2.25(s, 3H) | 475 (30), 205 (27), 189 (51), 145 (100), 123 (22) |
| 3 | CH | O | H | 4-CH₃—C₆H₄ | 8.05(s, 1H), 7.59(s, 1H), 7.52~7.01(m, 12H), 5.70(d, 1H), 5.11(s, 2H), 3.80(s, 3H), 3.66(s, 3H), 2.28(s, 3H) | 475 (42), 205 (21), 189 (32), 145 (100) |
| 4 | CH | O | H | 3,4-(CH₃)₂—C₆H₃ | 8.01(s, 1H), 7.60(s, 1H), 7.59~6.92(m, 11H), 5.65(d, 1H), 5.15(s, 2H), 3.77(s, 3H), 3.62(s, 3H), 2.20(s, 6H) | 489 (12), 205 (20), 189 (22), 145 (100), 118 (59) |
| 5 | CH | O | H | 3,5-(CH₃)₂—C₆H₃ | 8.02(s, 1H), 7.55(s, 1H), 7.51~6.84(m, 11H), 5.64(d, 1H), 5.12(s, 2H), 3.77(s, 3H), 3.65(s, 3H), 2.26(s, 6H) | 489 (26), 205 (22), 145 (100), 137 (25) |
| 6 | CH | O | H | 4-C₂H₅—C₆H₄ | 8.06(s, 1H), 7.59(s, 1H), 7.55~7.03(m, 12H), 5.70(d, 1H), 5.16(s, 2H), 3.76(s, 3H), 3.67(s, 3H), 2.61(q, 2H), 1.24(t, 3H) | 489 (44), 205 (62), 168 (14), 145 (100), 86 (26) |
| 7 | CH | O | H | 4-n-C₄H₉—C₆H₄ | 8.02(s, 1H), 7.59(s, 1H), 7.57~7.01(m, 12H), 5.70(d, 1H), 5.17(s, 2H), 3.79(s, 3H), 3.66(s, 3H), 2.58(t, 2H), 1.64~1.21(m, 4H), 0.92(t, 3H) | 517 (21), 149 (54), 84 (78), 84 (78), 55 (45), 43 (100) |
| 8 | CH | O | H | 3-CH₃O—C₆H₄ | 8.01(s, 1H), 7.60(s, 1H), 7.57~6.70(m, 12H), 5.65(d, 1H), 5.15(s, 2H), 3.81(s, 3H), 3.79(s, 3H), 3.64(s, 3H) | 491 (42), 205 (26), 189 (29), 145 (100) |
| 9 | CH | O | H | 4-CH₃O—C₆H₄ | 8.06(s, 1H), 7.60(s, 1H), 7.53~6.78(m, 12H), 5.69(d, 1H), 5.10(s, 2H), 3.81(s, 3H), 3.79(s, 3H), 3.67(s, 3H) | 491 (56), 205 (19), 189 (25), 145 (100), 139 (24) |
| 10 | CH | O | H | 4-C₂H₅O—C₆H₄ | 8.02(s, 1H), 7.61(s, 1H), 7.59~6.78(m, 12H), 5.64(d, 1H), 5.16(s, 2H), 4.00(q, 2H), 3.79(s, 3H), 3.63(s, 3H), 1.40(t, 3H) | 505 (19), 145 (100), 125 (37) |
| 11 | CH | O | H | 3-F—C₆H₄ | 8.00(s, 1H), 7.60(s, 1H), 7.58~6.80(m, 12H), 5.63(d, 1H), 5.19(s, 2H), 3.78(s, 3H), 3.62(s, 3H) | 479 (35), 205 (32), 189 (42), 144 (100) |
| 12 | CH | O | H | 4-F—C₆H₄ | 8.05(s, 1H), 7.58(s, 1H), 7.56~6.89(m, 12H), 5.68(d, 1H), 5.16(s, 2H), 3.79(s, 3H), 3.66(s, 3H) | 479 (21), 205 (95), 190 (23), 145 (100) |
| 13 | CH | O | H | 3-Cl—C₆H₄ | 8.06(s, 1H), 7.57(s, 1H), 7.55~7.00(m, 12H), 5.67(d, 1H), 5.14(s, 2H), 3.76(s, 3H), 3.64(s, 3H) | 495 (41), 205 (97), 189 (49), 145 (100) |
| 14 | CH | O | H | 4-Cl—C₆H₄ | 8.05(s, 1H), 7.58(s, 1H), 7.54~7.02(m, 12H), 5.65(d, 1H), 5.13(s, 2H), 3.78(s, 3H), 3.65(s, 3H) | 495 (43), 205 (59), 189 (98), 145 (100), 131 (27), 103 (21) |
| 15 | CH | O | H | 3,4-OCH₂O—C₆H₃ | 8.01(s, 1H), 7.61(s, 1H), 7.59~6.64(m, 11H), 5.86(s, 2H), 5.56(d, 1H), 5.15(s, 2H), 3.77(s, 3H), 3.64(s, 3H) | 505 (36), 205 (20), 188 (23), 144 (100) |
| 16 | CH | NH | H | C₆H₅ | 8.07(s, 1H), 7.61(s, 1H), 7.59~6.89(m, 13H), 5.71(d, 1H), 5.17(s, 2H), 4.14(b, 1H), 3.64(s, 3H), 2.96(d, 3H) | 460 (28), 188 (100), 149 (53) |
| 17 | CH | NH | H | 3-CH₃—C₆H₄ | 8.09(s, 1H), 7.62(s, 1H), 7.61~6.97(m, 12H), 5.67(d, 1H), 5.17(s, 2H), 4.13(b, 1H), 3.63(s, 3H), 2.97(d, 3H), 2.29(s, 3H) | 474 (40), 188 (100), 144 (46), 42 (21) |
| 18 | CH | NH | H | 3,5-(CH₃)₂—C₆H₃ | 8.09(s, 1H), 7.61(s, 1H), 7.59~6.81(m, 11H), 5.71(d, 1H), 5.16(s, 2H), 4.16(b, 1H), 3.61(s, 3H), 2.95(d, 3H), 2.23(s, 6H) | 488 (52), 188 (100), 144 (58), 137 (17), 42 (26) |
| 19 | CH | NH | H | 4-C₂H₅—C₆H₄ | 8.07(s, 1H), 7.62(s, 1H), 7.61~7.09(m, 12H), 5.68(d, 1H), 5.17(s, 2H), 4.17(b, 1H), 3.63(s, 3H), 2.98(d, 3H), 2.59(q, 2H), 1.24(t, 3H) | 488 (52), 188 (100), 144 (42), 44 (37) |
| 20 | CH | NH | H | 4-CH₃O—C₆H₄ | 8.08(s, 1H), 7.63(s, 1H), 7.61~6.72(m, 12H), 5.70(d, 1H), 5.16(s, 2H), 4.17(b, 1H), 3.78(s, 3H), 3.63(s, 3H), 2.97(d, 3H) | 490 (45), 188 (100), 144 (58), 44 (25) |
| 21 | CH | NH | H | 4-F—C₆H₄ | 8.07(s, 1H), 7.62(s, 1H), 7.60~6.87(m, 12H), 5.67(d, 1H), 5.17(s, 2H), 4.14(b, 1H), 3.64(s, 3H), 2.96(d, 3H) | 478 (62), 188 (100), 144 (61), 103 (23) |
| 22 | CH | NH | H | 3-Cl—C₆H₄ | 8.10(s, 1H), 7.62(s, 1H), 7.60~6.97(m, 12H), 5.63(d, 1H), 5.16(s, 2H), 4.15(b, 1H), 3.61(s, 3H), 2.95(d, 3H) | 494 (42), 188 (100), 144 (46) |
| 23 | CH | NH | H | 3,4-OCH₂O—C₆H₃ | 8.08(s, 1H), 7.62(s, 1H), 7.61~6.68(m, 11H), 5.91(s, 2H), 5.62(d, 1H), 5.18(s, 2H), 4.12(b, 1H), 3.61(s, 3H), 2.97(d, 3H) | 504 (28), 445 (34), 188 (94), 144 (100), 103 (21) |
| 24 | N | O | H | C₆H₅ | 8.01(s, 1H), 7.53~7.01(m, 13H), 5.67(d, 1H), 5.11(s, 2H), 4.00(s, 3H), 3.83(s, 3H) | 462 (42), 131 (66), 116 (100), 59 (61) |

TABLE 7-continued

| Ex. No. | X | Y | R¹ | R² | ¹H-NMR(CDCl₃, TMS)δ (ppm) | MS (m/e) (M, int) |
|---|---|---|---|---|---|---|
| 25 | N | O | H | 4-CH₃—C₆H₄ | 8.01(s, 1H), 7.50~7.06(m, 12H), 5.68(d, 1H), 5.10(s, 2H), 4.01(s, 3H), 3.82(s, 3H), 2.30(s, 3H) | 476 (53), 131 (67), 116 (100), 59 (52) |
| 26 | N | O | H | 4-CH₃O—C₆H₄ | 8.00(s, 1H), 7.62~6.81(m, 12H), 5.65(d, 1H), 5.09(s, 2H), 4.02(s, 3H), 3.82(s, 3H), 3.78(s, 3H) | 492 (98), 139 (83), 131 (100), 116 (77), 59 (64) |
| 27 | N | O | H | 4-F—C₆H₄ | 8.01(s, 1H), 7.46~6.93(m, 12H), 5.67(d, 1H), 5.09(s, 2H), 4.02(s, 3H), 3.83(s, 3H) | 480 (42), 131 (64), 116 (100), 59 (61) |
| 28 | N | O | H | 4-Cl—C₆H₄ | 8.00(s, 1H), 7.46~7.13(m, 12H), 5.66(d, 1H), 5.10(s, 2H), 4.01(s, 3H), 3.82(s, 3H) | 496 (17), 131 (61), 116 (100), 59 (52) |
| 29 | N | O | H | 3,4-OCH₂O—C₆H₃ | 8.00(s, 1H), 7.50~6.71(m, 11H), 6.97(s, 2H), 5.65(d, 1H), 5.10(s, 2H), 4.02(s, 3H), 3.82(s, 3H) | 506 (23), 153 (55), 131 (52), 116 (80), 59 (100) |
| 30 | N | NH | H | C₆H₅ | 8.01(s, 1H), 7.69~6.90(m, 13H), 6.74(b, 1H), 5.65(d, 1H), 5.11(s, 2H), 3.94(s, 3H), 2.86(d, 3H) | 461 (38), 221 (81), 204 (64), 132 (73), 116 (100), 58 (61) |
| 31 | N | NH | H | 3-CH₃—C₆H₄ | 8.00(s, 1H), 7.67~6.94(m, 12H), 6.76(b, 1H), 5.68(d, 1H), 5.14(s, 2H), 3.92(s, 3H), 2.87(d, 3H), 2.30(s, 3H) | 475 (31), 221 (86), 204 (53), 132 (99), 116 (100), 58 (73) |
| 32 | N | NH | H | 3,4-(CH₃)₂—C₆H₃ | 8.01(s, 1H), 7.72~7.00(m, 11H), 6.76(b, 1H), 5.63(d, 1H), 5.14(s, 2H), 3.85(s, 3H), 2.87(d, 3H), 2.23(s, 6H) | 489 (42), 307 (47), 149 (100) |
| 33 | N | NH | H | 4-C₂H₅—C₆H₄ | 8.01(s, 1H), 7.55~7.09(m, 12H), 6.75(b, 1H), 5.70(d, 1H), 5.09(s, 2H), 3.93(s, 3H), 2.87(d, 3H), 2.60(q, 2H), 1.20(t, 3H) | 489 (55), 221 (21), 132 (100), 116 (88) |
| 34 | N | NH | H | 4-n-C₄H₉—C₆H₄ | 8.01(s, 1H), 7.53~7.02(m, 12H), 6.76(b, 1H), 5.68(d, 1H), 5.12(s, 2H), 3.94(s, 3H), 2.87(d, 3H), 2.56(t, 2H), 1.67–1.21(m, 4H), 0.91(t, 3H) | 517 (35), 205 (37), 132 (89), 116 (73), 58 (100) |
| 35 | N | NH | H | 3-CH₃O—C₆H₄ | 8.00(s, 1H), 7.55~6.96(m, 12H), 6.75(b, 1H), 5.64(d, 1H), 5.13(s, 2H), 3.86(s, 3H), 3.78(s, 3H), 2.87(d, 3H) | 491 (15), 221 (57), 205 (35), 132 (85), 116 (86), 58 (100) |
| 36 | N | NH | H | 4-C₂H₅O—C₆H₄ | 8.00(s, 1H), 7.57~6.84(m, 12H), 6.75(b, 1H), 5.65(d, 1H), 5.15(s, 2H), 4.00(q, 2H), 3.87(s, 3H), 2.86(d, 3H) | 505 (82), 205 (39), 181 (23), 132 (100), 116 (84), 58 (88) |
| 37 | N | NH | H | 4-F—C₆H₄ | 8.01(s, 1H), 7.58~6.87(m, 12H), 6.77(b, 1H), 5.64(d, 1H), 5.11(s, 2H), 3.90(s, 3H), 2.88(d, 3H) | 479 (43), 221 (44), 132 (100), 116 (76), 58 (46) |
| 38 | N | NH | H | 3-Cl—C₆H₄ | 8.01(s, 1H), 7.58~7.02(m, 12H), 6.74(b, 1H), 5.63(d, 1H), 5.12(s, 2H), 3.88(s, 3H), 2.88(d, 3H) | 495 (27), 221 (99), 205 (39), 132 (90), 116 (100), 58 (79) |
| 39 | N | NH | H | 3,4-OCH₂O—C₆H₃ | 8.02(s, 1H), 7.58~6.81(m, 11H), 6.76(b, 1H), 5.93(s, 2H), 5.66(d, 1H), 5.10(s, 2H), 3.94(s, 3H), 2.87(d, 3H) | 505 (63), 284 (25), 153 (39), 132 (99), 116 (100), 58 (43) |
| 40 | CH | O | CH₃ | C₆H₅ | 7.48(s, 1H), 7.42~6.87(m, 13H), 5.67(d, 1H), 5.20(s, 2H), 3.78(s,3H), 3.65(s, 3H), 2.24(s, 3H) | 475 (11), 205 (35), 189 (17), 145 (100), 109 (31) |
| 41 | CH | O | CH₃ | 3-CH₃—C₆H₄ | 7.50(s, 1H), 7.48~6.92(m, 12H), 5.66(d, 1H), 5.19(s, 2H), 3.77(s, 3H), 3.67(s, 3H), 2.31(s, 3H), 2.23(s, 3H) | 489 (20), 206 (40), 189 (17), 145 (100), 123 (29) |
| 42 | CH | O | CH₃ | 4-CH₃—C₆H₄ | 7.50(s, 1H), 7.48~6.97(m, 12H), 5.64(d, 1H), 5.19(s, 2H), 3.75(s, 3H), 3.64(s, 3H), 2.31(s, 3H), 2.25(s, 3H) | 489 (31), 399 (31), 206 (25), 145 (100), 103 (18) |
| 43 | CH | O | CH₃ | 3,4-(CH₃)₂—C₆H₃ | 7.58(s, 1H), 7.57~6.98(m, 11H), 5.63(d, 1H), 5.18(s, 2H), 3.78(s, 3H), 3.63(s, 3H), 2.20(s, 3H), 2.18(s, 6H) | 503 (20), 205 (44), 189 (18), 145 (100) |
| 44 | CH | O | CH₃ | 3,5-(CH₃)₂—C₆H₃ | 7.48(s, 1H), 7.45~6.67(m, 11H), 5.50(d, 1H), 5.10(s, 2H), 3.58(s, 3H), 3.52(s, 3H), 2.18(s, 3H), 2.15(s, 3H), 2.09(s, 3H) | 503 (26), 205 (35), 145 (100) |
| 45 | CH | O | CH₃ | 4-C₂H₅—C₆H₄ | 7.48(s, 1H), 7.44~6.93(m, 12H), 5.60(d, 1H), 5.11(s, 2H), 3.67(s, 3H), 3.57(s, 3H), 3.36(q, 2H), 2.11(s, 3H), 1.12(t, 3H) | 503 (11), 282 (19), 205 (40), 145 (100) |
| 46 | CH | O | CH₃ | 4-n-C₄H₉—C₆H₄ | 7.59(s, 1H), 7.58~7.00(m, 12H), 5.64(d, 1H), 5.19(s, 2H), 3.79(s, 3H), 3.64(s, 3H), 2.57(t, 2H), 2.20(s, 3H), 1.44–1.19(m, 4H), 0.91(t, 3H) | 531 (17), 301 (24), 205 (55), 189 (21), 145 (100) |

TABLE 7-continued

| Ex. No. | X | Y | R¹ | R² | ¹H-NMR(CDCl₃, TMS)δ (ppm) | MS (m/e) (M, int) |
|---|---|---|---|---|---|---|
| 47 | CH | O | CH₃ | 3-CH₃O—C₆H₄ | 7.59(s, 1H), 7.58~6.78(m, 12H), 5.65(d, 1H), 5.17(s, 2H), 3.80(s, 3H), 3.78(s, 3H), 3.62(s, 3H), 2.18(s, 3H) | 505 (51), 284 (27), 205 (44), 145 (100), 131 (38) |
| 48 | CH | O | CH₃ | 4-CH₃O—C₆H₄ | 7.49(s, 1H), 7.46~6.68(m, 12H), 5.58(d, 1H), 5.08(s, 2H), 3.67(s, 3H), 3.65(s, 3H), 3.54(s, 3H), 2.11(s, 3H) | 505 (13), 205 (24), 145 (100), 139 (32), 84 (32) |
| 49 | CH | O | CH₃ | 4-C₂H₅O—C₆H₄ | 7.60(s, 1H), 7.58~6.81(m, 12H), 5.66(d, 1H), 5.19(s, 2H), 4.00(q, 2H), 3.76(s, 3H), 3.65(s, 3H), 2.20(s, 3H), 1.38(t, 3H) | 519 (49), 298 (37), 159 (46), 145 (100), 131 (59) |
| 50 | CH | O | CH₃ | 3-F—C₆H₄ | 7.58(s, 1H), 7.55~6.80(m, 12H), 5.64(d, 1H), 5.18(s, 2H), 3.77(s, 3H), 3.68(s, 3H), 2.18(s, 3H) | 493 (28), 205 (33), 189 (26), 145 (100), 131 (42) |
| 51 | CH | O | CH₃ | 4-F—C₆H₄ | 7.61(s, 1H), 7.58~6.94(m, 12H), 5.72(d, 1H), 5.20(s, 2H), 3.80(s, 3H), 3.68(s, 3H), 2.20(s, 3H) | 493 (71), 272 (33), 205 (69), 189 (60), 145 (100), 127 (64) |
| 52 | CH | O | CH₃ | 3-CH₃-4-Cl—C₆H₃ | 7.61(s, 1H), 7.52~6.97(m, 11H), 5.57(d, 1H), 5.12(s, 2H), 3.78(s, 3H), 3.64(s, 3H), 2.21(s, 3H), 2.16(s, 3H) | 523 (44), 302 (34), 205 (23), 145 (100) |
| 53 | CH | O | CH₃ | 3-Cl—C₆H₄ | 7.53(s, 1H), 7.52~7.00(m, 12H), 5.66(d, 1H), 5.15(s, 2H), 3.77(s, 3H), 3.67(s, 3H), 2.25(s, 3H) | 509 (42), 205 (31), 189 (26), 145 (100) |
| 54 | CH | O | CH₃ | 4-Cl—C₆H₄ | 7.52(s, 1H), 7.50~7.01(m, 12H), 5.67(d, 1H), 5.18(s, 2H), 3.78(s, 3H), 3.66(s 3H), 2.24(s, 3H) | 509 (37), 206 (30), 189 (24), 145 (100), 103 (25) |
| 55 | CH | O | CH₃ | 3,4-OCH₂O—C₆H₃ | 7.60(s, 1H), 7.58~6.75(m, 11H), 5.88(s, 2H), 5.63(d, 1H), 5.20(s, 2H), 3.79(s, 3H), 3.62(s, 3H), 2.19(s, 3H) | 519 (39), 205 (31), 189 (16), 145 (100), 131 (33) |
| 56 | CH | O | CH₃ | C₁₀H₇-2-yl- (naphthalen-2-yl) | 7.56(s, 1H), 8.08~7.05(m, 15H), 6.34(d, 1H), 5.16(s, 2H), 3.65(s, 3H), 3.61(s, 3H), 2.16(s, 3H) | 525 (27), 205 (33), 159 (28), 145 (100) |
| 57 | CH | NH | CH₃ | 4-CH₃—C₆H₄ | 7.60(s, 1H), 7.58~7.02(m, 12H), 5.71(d, 1H), 5.18(s, 2H), 4.23(b, 1H), 3.61(s, 3H), 2.85(d, 3H), 2.37(s, 3H), 2.23(s, 3H) | 488 (23), 188 (100), 144 (56) |
| 58 | CH | NH | CH₃ | 3,5-(CH₃)₂—C₆H₃ | 7.61(s, 1H), 7.59~6.81(m, 11H), 5.66(d, 1H), 5.18(s, 2H), 4.23(b, 1H), 3.62(s, 3H), 2.91(d, 3H), 2.22(s, 6H) | 502 (48), 188 (100), 144 (76) |
| 59 | CH | NH | CH₃ | 4-C₂H₅—C₆H₄ | 7.61(s, 1H), 7.60~7.01(m, 12H), 5.70(d, 1H), 5.19(s, 2H), 4.22(b, 1H), 3.62(s, 3H), 2.88(d, 3H), 2.61(q, 2H), 2.22(s, 3H), 1.22(t, 3H) | 502 (13), 188 (100), 144 (94) |
| 60 | CH | NH | CH₃ | 4-CH₃O—C₆H₄ | 7.60(s, 1H), 7.59~6.75(m, 12H), 5.68(d, 1H), 5.18(s, 2H), 4.21(b, 1H), 3.78(s, 3H), 3.61(s, 3H), 2.92(d, 3H), 2.21(s, 3H) | 504 (31), 188 (100), 144 (85) |
| 61 | CH | NH | CH₃ | 3-CH₃-4-Cl—C₆H₃ | 7.62(s, 1H), 7.60~7.01(m, 11H), 5.64(d, 1H), 5.17(s, 2H), 4.21(b, 1H), 3.60(s, 3H), 2.90(d, 3H), 2.32(s, 6H), 2.21(s, 3H) | 522 (13), 188 (100), 144 (49) |
| 62 | CH | NH | CH₃ | 3-Cl—C₆H₄ | 7.61(s, 1H), 7.60~7.03(m, 12H), 5.67(d, 1H), 5.19(s, 2H), 4.21(b, 1H), 3.63(s, 3H), 2.92(d, 3H), 2.23(s, 3H) | 508 (32), 188 (100), 144 (60) |
| 63 | CH | NH | CH₃ | 3,4-OCH₂O—C₆H₃ | 7.60(s, 1H), 7.59~6.78(m, 11H), 5.91(s, 2H), 5.65(d, 1H), 5.18(s, 2H), 4.23(b, 1H), 3.61(s, 3H), 2.91(d, 3H), 2.21(s, 3H) | 518 (41), 188 (100), 144 (46) |
| 64 | N | O | CH₃ | C₆H₅ | 7.49~7.16(m, 13H), 5.73(d, 1H), 5.15(s, 2H), 4.04(s, 3H), 3.82(s, 3H), 2.21(s, 3H) | 476 (14), 131 (68), 116 (100), 59 (44) |
| 65 | N | O | CH₃ | 3-CH₃—C₆H₄ | 7.50~6.98(m, 12H), 5.68(d, 1H), 5.15(s, 2H), 4.03(s, 3H), 3.82(s, 3H), 2.31(s, 3H), 2.21(s, 3H) | 490 (27), 131 (67), 116 (100), 59 (45) |
| 66 | N | O | CH₃ | 4-CH₃—C₆H₄ | 7.49~7.06(m, 12H), 5.67(d, 1H), 5.13(s, 2H), 4.02(s, 3H), 3.80(s, 3H), 2.29(s, 3H), 2.18(s, 3H) | 490 (28), 131 (65), 123 (66), 116 (100), 59 (64) |
| 67 | N | O | CH₃ | 3,4-(CH₃)₂—C₆H₃ | 7.45~7.00(m, 11H), 5.64(d, 1H), 5.12(s, 2H), 4.00(s, 3H), 3.79(s, 3H), 2.20(s, 6H), 2.17(s, 3H) | 504 (51), 137 (62), 131 (60), 116 (100), 59 (77) |
| 68 | N | O | CH₃ | 3,5-(CH₃)₂—C₆H₃ | 7.46~6.82(m, 11H), 5.62(d, 1H), 5.13(s, 2H), 4.01(s, 3H), 3.79(s, 3H), 2.24(s, 6H), 2.18(s, 3H) | 504 (56), 131 (62), 115 (100), 59 (48) |

TABLE 7-continued

| Ex. No. | X | Y | R¹ | R² | ¹H-NMR(CDCl₃, TMS)δ (ppm) | MS (m/e) (M, int) |
|---|---|---|---|---|---|---|
| 69 | N | O | CH₃ | 4-C₂H₅—C₆H₄ | 7.50~7.08(m, 12H), 5.69(d, 1H), 5.12(s, 2H), 4.01(s, 3H), 3.81(s, 3H), 2.60(q, 2H), 2.18(s, 3H), 1.19(t, 3H) | 504 (31), 131 (70), 116 (100), 59 (61) |
| 70 | N | O | CH₃ | 4-n-C₄H₉—C₆H₄ | 7.52~7.07(m, 12H), 5.70(d, 1H), 5.15(s, 2H), 4.04(s, 3H), 3.82(s, 3H), 2.58(t, 2H), 2.20(s, 3H), 1.67~1.24(m, 4H), 0.93(t, 3H) | 532 (35), 131 (66), 116 (100), 59 (48) |
| 71 | N | O | CH₃ | 3-CH₃O—C₆H₄ | 7.58~6.77(m, 12H), 5.69(d, 1H), 5.13(s, 2H), 4.03(s, 3H), 3.83(s, 3H), 3.76(s, 3H), 2.19(s, 3H) | 506 (30), 131 (69), 116 (100), 59 (69) |
| 72 | N | O | CH₃ | 4-CH₃O—C₆H₄ | 7.56~6.79(m, 12H), 5.66(d, 1H), 5.12(s, 2H), 4.01(s, 3H), 3.80(s, 3H), 3.76(s, 3H), 2.18(s, 3H) | 506 (46), 139 (80), 131 (79), 116 (100), 59 (79) |
| 73 | N | O | CH₃ | 4-C₂H₅O—C₆H₄ | 7.57~6.78(m, 12H), 5.65(d, 1H), 5.13(s, 2H), 4.02(s, 3H), 4.01(q, 2H), 3.80(s, 3H), 2.18(s, 3H), 1.38(t, 3H) | 520 (83), 131 (70), 125 (72), 116 (100), 59 (68) |
| 74 | N | O | CH₃ | 4-F—C₆H₄ | 7.50~6.91(m, 12H), 5.65(d, 1H), 5.13(s, 2H), 4.00(s, 3H), 3.79(s, 3H), 2.17(s, 3H) | 494 (25), 131 (63), 116 (100), 59 (49) |
| 75 | N | O | CH₃ | 3-Cl—C₆H₄ | 7.49~7.08(m, 12H), 5.62(d, 1H), 5.13(s, 2H), 4.01(s, 3H), 3.80(s, 3H), 2.18(s, 3H) | 510 (43), 206 (44), 131 (71), 116 (100), 59 (65) |
| 76 | N | O | CH₃ | 4-Cl—C₆H₄ | 7.50~7.14(m, 12H), 5.67(d, 1H), 5.16(s, 2H), 4.04(s, 3H), 3.83(s, 3H), 2.21(s, 3H) | 510 (21), 206 (61), 131 (54), 116 (100), 59 (74) |
| 77 | N | NH | CH₃ | C₆5 | 7.47~7.15(m, 13H), 6.71(b, 1H), 5.70(d, 1H), 5.13(s, 2H), 3.93(s, 3H), 2.84(d, 3H), 2.18(s, 3H) | 475 (24), 132 (50), 116 (68), 58 (100) |
| 78 | N | NH | CH₃ | 3-CH₃—C₆H₄ | 7.46~7.16(m, 12H), 6.70(b, 1H), 5.66(d, 1H), 5.12(s, 2H), 3.93(s, 3H), 2.85(d, 3H), 2.30(s, 3H), 2.17(s, 3H) | 489 (22), 131 (56), 116 (73), 58 (100) |
| 79 | N | NH | CH₃ | 4-C₂H₅—C₆H₄ | 7.46~7.08(m, 12H), 6.68(b, 1H), 5.68(d, 1H), 5.11(s, 2H), 3.92(s, 3H), 2.84(d, 3H), 2.58(q, 2H), 2.16(s, 3H), 1.19(t, 3H) | 503 (54), 31 (57), 115 (78), 58 (100) |
| 80 | N | NH | CH₃ | 3-CH₃O—C₆H₄ | 7.49~6.97(m, 12H), 6.72(b, 1H), 5.65(d, 1H), 5.13(s, 2H), 3.94(s, 3H), 3.78(s, 3H), 2.84(d, 3H), 2.18(s, 3H) | 505 (27), 32 (47), 116 (59), 58 (100) |
| 81 | N | NH | CH₃ | 4-C₂H₅O—C₆H₄ | 7.50~6.81(m, 12H), 6.70(b, 1H), 5.67(d, 1H), 5.12(s, 2H), 4.00(q, 2H), 3.93(s, 3H), 2.83(d, 3H), 2.17(s, 3H), 1.38(t, 3H) | 519 (61), 32 (52), 116 (75), 58 (100) |
| 82 | N | NH | CH₃ | 4-F—C₆H₄ | 7.47~6.93(m, 12H), 6.71(b, 1H), 5.68(d, 1H), 5.13(s, 2H), 3.94(s, 3H), 2.86(d, 3H), 2.16(s, 3H) | 493 (21), 32 (43), 116 (61), 58 (100) |
| 83 | CH | O | CF₃ | C₆H₅ | 7.52(s, 1H), 7.48~7.06(m, 13H), 5.68(d, 1H), 5.14(s, 2H), 3.67(s, 3H), 3.58(s, 3H) | 529 (12), 89 (41), 145(100), |
| 84 | CH | O | CF₃ | 3-CH₃—C₆H₄ | 7.53(s, 1H), 7.44~6.97(m, 12H), 5.68(d, 1H), 5.16(s, 2H), 3.65(s, 3H), 3.57(s, 3H), 2.32(s, 3H) | 543 (48), 53 (48), 189 (48), 45 (100), 123 (30), |
| 85 | CH | O | CF₃ | 4-CH₃—C₆H₄ | 7.54(s, 1H), 7.49~7.05(m, 12H), 5.69(d, 1H), 5.17(s, 2H), 3.72(s, 3H), 3.61(s, 3H), 2.31(s, 3H) | 543 (65), 89 (30), 145 (100), 23 (25) |
| 86 | CH | O | CF₃ | 3,5-(CH₃)₂—C₆H₃ | 7.54(s, 1H), 7.46~6.87(m, 11H), 5.67(d, 1H), 5.14(s, 2H), 3.64(s, 3H), 3.56(s, 3H), 2.33(s, 6H) | 557 (23), 05 (27), 189 (39), 45 (100) |
| 87 | CH | O | CF₃ | 4-n-C₄H₉C₆H₄ | 7.53(s, 1H), 7.43~7.05(m, 12H), 5.64(d, 1H), 5.18(s, 2H), 3.68(s, 3H), 3.61(s, 3H), 2.58(t, 2H), 1.64~1.24(m, 4H), 0.92(t, 3H) | 585 (41), 88 (28), 144 (100) |
| 88 | CH | O | CF₃ | 3-CH₃O—C₆H₄ | 7.54(s, 1H), 7.45~6.78(m, 12H), 5.68(d, 1H), 5.18(s, 2H), 3.77(s, 3H), 3.66(s, 3H), 3.54(s, 3H) | 559 (87), 89 (48), 145 (100), 39 (72) |
| 89 | CH | O | CF₃ | 4-CH₃O—C₆H₄ | 7.55(s, 1H), 7.43~6.79(m, 12H), 5.69(d, 1H), 5.19(s, 2H), 3.76(s, 3H), 3.65(s, 3H) | 559 (92), 89 (24), 145 (100), 39 (26) |
| 90 | CH | O | CF₃ | 3-F—C₆H₄ | 7.54(s, 1H), 7.53~6.81(m, 12H), 5.64(d, 1H), 5.17(s, 2H), 3.74(s, 3H), 3.62(s, 3H) | 547 (42), 188 (50), 144 (100) |
| 91 | CH | O | CF₃ | 3-CH₃-4-Cl—C₆H₃ | 7.56(s, 1H), 7.47~7.03(m, 11H), 5.61(d, 1H), 5.20(s, 2H), 3.70(s, 3H), 3.61(s, 3H), 2.28(s, 3H) | 577 (41), 189 (94), 145(100), 84 (28) |
| 92 | CH | O | CF₃ | 4-Cl—C₆H₄ | 7.52(s, 1H), 7.48~7.04(m, 12H), 5.65(d, 1H), 5.16(s, 2H), 3.68(s, 3H), 3.59(s, 3H) | 563 (35), 189 (48), 145 (100), |
| 93 | CH | O | CF₃ | C₁₀H₇-2-yl- (naphthalen-2-yl) | 7.56(s, 1H), 8.06~7.10(m, 15H), 6.02(d, 1H), 5.19(s, 2H), 3.66(s, 3H), 3.57(s, 3H) | 579 (67), 189 (28), 159 (37), 145 (100) |
| 94 | CH | O | CF₃ | 3,4-OCH₂O—C₆H₃ | 7.54(s, 1H), 8.01~7.11(m, 11H), 6.78(s, 2H), 5.68(d, 1H), 5.17(s, 2H), 3.63(s, 3H), 3.54(s, 3H) | 573 (61), 189 (52), 159 (100), 145 (58) |

TABLE 7-continued

| Ex. No. | X | Y | R¹ | R² | $^1$H-NMR(CDCl$_3$, TMS)δ (ppm) | MS (m/e) (M, int) |
|---|---|---|---|---|---|---|
| 95 | CH | NH | CF$_3$ | C$_6$H$_5$ | 7.58(s, 1H), 7.57~7.08(m, 13H), 5.71(d, 1H), 5.21(s, 2H), 4.09(b, 1H), 3.58(s, 3H), 2.82(d, 3H) | 528 (21), 188 (100), 144 (67), 109 (34) |
| 96 | CH | NH | CF$_3$ | 3-CH$_3$—C$_6$H$_4$ | 7.57(s, 1H), 7.49~6.94(m, 12H), 5.68(d, 1H), 5.17(s, 2H), 4.08(b, 1H), 3.60(s, 3H), 2.71(d, 3H), 2.28(s, 3H) | 542 (61), 188 (100), 144 (54) |
| 97 | CH | NH | CF$_3$ | 3,5-(CH$_3$)$_2$—C$_6$H$_3$ | 7.60(s, 1H), 7.58~6.80(m, 11H), 5.67(d, 1H), 5.20(s, 2H), 4.17(b, 1H), 3.60(s, 3H), 2.83(d, 3H), 2.23(s, 6H) | 556 (22), 188 (100), 144 (50) |
| 98 | CH | NH | CF$_3$ | 3-CH$_3$O—C$_6$H$_4$ | 8.01(b, 1H), 7.57(s, 1H), 7.56~6.78(m, 12H), 5.69(d, 1H), 5.20(s, 2H), 3.78(s, 3H), 3.58(s, 3H), 2.86(d, 3H) | 558 (23), 188 (100), 144 (65) |
| 99 | CH | NH | CF$_3$ | 4-CH$_3$O—C$_6$H$_4$ | 7.63(s, 1H), 7.61~6.81(m, 12H), 5.70(d, 1H), 5.21(s, 2H), 4.18(b, 1H), 3.78(s, 3H), 3.61(s, 3H), 2.91(d, 3H) | 558 (19), 188 (100), 144 (64) |
| 100 | CH | NH | CF$_3$ | 4-Cl—C$_6$H$_4$ | 7.59(s, 1H), 7.51~7.09(m, 12H), 5.69(d, 1H), 5.18(s, 2H), 4.10(b, 1H), 3.58(s, | 562 (30), 188 (100), 144 (62), 42 (30) |
| 101 | CH | NH | CF$_3$ | C$_{10}$H$_7$-2-yl-(naphthalen-2-yl) | 7.55(s, 1H), 8.01~7.08(m, 15H), 6.33(d, 1H), 5.17(s, 2H), 4.11(b, 1H), 3.56(s, 3H), 2.74(d, 3H) | 578 (42), 188 (44), 144 (54), 145 (100) |
| 102 | N | O | CF$_3$ | C$_6$H$_5$ | 7.51~7.08(m, 13H), 5.70(d, 1H), 5.17(s, 2H), 3.98(s, 3H), 3.73(s, 3H) | 530 (25), 206 (18), 131 (60), 116 (100), 59 (68) |

EXAMPLE 103

Preparation of Methyl (2E)-3-Methoxy-2-{2'-[[[3"-(1'''-fluoro-3''',3''',3'''-trifluoro-2'''-phenyl-1'''-propenyloxy)phenyl]imino]oxy]methylphenyl}propenoate (Compound 103)

341 mg (1 mmol) of the compound obtained in Preparation 12 was added to 10 ml of acetonitrile and 40 mg of sodium hydride (1 mmol) dispersed in mineral oil (60%) was added thereto under a nitrogen atmosphere. The resulting solution was stirred for 30 minutes and 208 mg (1 mmol) of the compound obtained in Preparation 41 was added slowly thereto. The resultant solution was stirred for 4 hours with heating, mixed with water and extracted with ethyl acetate. The organic layer was dried over magnesium sulfate and the solvent was removed under a reduced pressure. The residue was subjected to silica gel column chromatography using a mixture of n-hexane and ethyl acetate (4:1) as an eluent to obtain 470 mg (yield 91%) of the title compound as a colorless liquid.

$^1$H-NMR (CDCl$_3$, TMS) δ (ppm): 8.01 (s, 1H), 7.59 (s, 1H), 7.58–6.92 (m, 13H), 5.18 (s, 2H), 3.78 (s, 3H), 3.61 (s, 3H); $^{19}$F-NMR (CDCl$_3$, CFCl$_3$) δ (ppm): −75.916 (q, 3F, J=12.22 Hz), −58.714 (d, 1F, J=12.267 Hz) E,E-isomer, −76.313 (q, 3F, J=23.93 Hz), −58.518 (d, 1F, J=24.676 Hz) E,Z-isomer; MS(m/e): 529 (M$^+$, 18), 205 (59), 189 (75), 145 (100), 131 (25).

EXAMPLE 120

Preparation of N-Methyl (2E)-3-Methoxy-2-{2'-[[[3"-(1'''-fluoro-3''',3''',3'''-trifluoro-2'''-phenyl-1'''-propenyloxy)phenyl]imino]oxy]methylphenyl}propenamide (Compound 120)

170 mg (0.5 mmol) of the compound obtained in Preparation 18 was added to 10 ml of acetonitrile and 40 mg of sodium hydride (1 mmol) dispersed in mineral oil (60%) was added thereto under a nitrogen atmosphere. The resulting solution was stirred for 30 minutes and 104 mg (0.5 mmol) of the compound obtained in Preparation 41 was added slowly thereto. The resultant solution was stirred for 2 hours at room temperature, mixed with water and extracted with ethyl acetate. The organic layer was dried over magnesium sulfate and the solvent was removed under a reduced pressure. The residue was subjected to silica gel column chromatography using a mixture of n-hexane and ethyl acetate (4:1) as an eluent to obtain 243 mg (yield 92%) of the title compound as a colorless liquid.

$^1$H-NMR (CDCl$_3$, TMS) δ (ppm): 8.01 (s, 1H), 7.62 (s, 1H), 7.61–7.00 (m, 13H), 5.18 (s, 2H), 4.17 (b, 1H), 3.63 (s, 3H), 2.98 (d, 3H); MS (m/e): 528 (M$^+$, 54), 188 (53), 144 (100), 103 (36), 76 (46).

The procedure of Example 103 or 120 was repeated using corresponding phenolic ester compounds or phenolic amide comounds of formula (V) and fluorinated vinyl compounds of formula (VI-b); or, alternatively, the procedure of Example 40, 64 or 77 was repeated using corresponding bromide compounds of formula (II) and the olefin substituted oxime compounds of formula (VII-b), to obtain various compounds of formula (I), as listed in Table 8.

TABLE 8

| Ex. No. | X | Y | R¹ | R² | ¹H-NMR(CDCl₃, TMS)δ (ppm) | MS (m/e) (M, int) |
|---|---|---|---|---|---|---|
| 103 | CH | O | H | C₆H₅ | 8.01(s, 1H), 7.59(s, 1H), 7.58~6.92(m, 13H), 5.18(s, 2H), 3.78(s, 3H), 3.61(s, 3H) | 529 (18), 205 (59), 189 (75), 145 (100), 131 (25) |
| 104 | CH | O | H | 3-CH₃—C₆H₄ | 8.01(s, 1H), 7.60(s, 1H), 7.59~6.92(m, 12H), 5.16(s, 2H), 3.78(s, 3H), 3.67(s, 3H), 2.32(s, 3H) | 543 (21), 221 (55), 205 (91), 189 (84), 145 (100) |
| 105 | CH | O | H | 4-CH₃—C₆H₄ | 8.00(s, 1H), 7.54(s, 1H), 7.52~6.97(m, 12H), 5.10(s, 2H), 3.71(s, 3H), 3.63(s, 3H), 2.28(s, 3H) | 543 (31), 205 (24), 189 (52), 145 (100), 103 (17) |
| 106 | CH | O | H | 3,4-(CH₃)₂—C₆H₃ | 8.01(s, 1H), 7.60(s, 1H), 7.59~6.90(m, 11H), 5.19(s, 2H), 3.77(s, 3H), 3.63(s, 3H), 2.25(s, 6H) | 557 (42), 205 (58), 189 (70), 145 (100), 76 (20) |
| 107 | CH | O | H | 3,5-(CH₃)₂—C₆H₃ | 8.02(s, 1H), 7.60(s, 1H), 7.58~7.01(m, 11H), 5.20(s, 2H), 3.77(s, 3H), 3.74(s, 3H), 2.38(s, 3H), 2.36(s, 3H) | 557 (11), 221 (21), 205 (87), 190 (33), 145 (100) |
| 108 | CH | O | H | 4-C₂H₅—C₆H₄ | 8.00(s, 1H), 7.60(s, 1H), 7.59~6.98(m, 12H), 5.19(s, 2H), 3.79(s, 3H), 3.63(s, 3H), 2.65(q, 2H), 1.22(t, 3H) | 557 (23), 539 (26), 205(100), 189 (93), 146 (62) |
| 109 | CH | O | H | 4-n-C₄H₉—C₆H₄ | 8.01(s, 1H), 7.61(s, 1H), 7.58~6.97(m, 12H), 5.18(s, 2H), 3.80(s, 3H), 3.64(s, 3H), 2.61(t, 2H), 1.74~1.28(m, 4H), 0.94(t, 3H) | 585 (28), 205 (52), 145 (100), 131 (20) |
| 110 | CH | O | H | 3-CH₃O—C₆H₄ | 8.00(s, 1H), 7.59(s, 1H), 7.58~6.86(m, 12H), 5.16(s, 2H), 3.81(s, 3H), 3.78(s, 3H), 3.62(s, 3H) | 559 (45), 205 (42), 189 (62), 145 (100), 86 (39) |
| 111 | CH | O | H | 4-CH₃O—C₆H₄ | 8.01(s, 1H), 7.56(s, 1H), 7.54~6.81(m, 12H), 5.18(s, 2H), 3.78(s, 3H), 3.75(s, 3H), 3.68(s, 3H) | 559 (47), 205 (31), 189 (47), 145 (100), 137 (17), 103 (14) |
| 112 | CH | O | H | 3-F—C₆H₄ | 8.00(s, 1H), 7.59(s, 1H), 7.58~6.91(m, 12H), 5.20(s, 2H), 3.78(s, 3H), 3.62(s, 3H) | 547 (32), 279 (13), 167 (34), 145 (100), 71 (55), 57 (94) |
| 113 | CH | O | H | 4-F—C₆H₄ | 8.03(s, 1H), 7.61(s, 1H), 7.58~6.94(m, 12H), 5.17(s, 2H), 3.81(s, 3H), 3.71(s, 3H) | 547 (31), 205 (85), 190 (26), 145 (100) |
| 114 | CH | O | H | 3-CF₃—C₆H₄ | 8.00(s, 1H), 7.58(s, 1H), 7.56~6.89(m, 12H), 5.18(s, 2H), 3.77(s, 3H), 3.62(s, 3H) | 597 (31), 205 (33), 189 (69), 145 (100), 76 (29) |
| 115 | CH | O | H | 4-CF₃—C₆H₄ | 8.02(s, 1H), 7.59(s, 1H), 7.57~6.94(m, 12H), 5.20(s, 2H), 3.79(s, 3H), 3.63(s, 3H) | 597 (43), 279 (21), 189 (39), 167 (66), 149 (100), 71 (46) |
| 116 | CH | O | H | 3-Cl—C₆H₄ | 8.03(s, 1H), 7.60(s, 1H), 7.57~7.02(m, 12H), 5.20(s, 2H), 3.81(s, 3H), 3.72(s, 3H) | 563 (42), 221 (69), 205 (94), 190 (87), 145 (100) |
| 117 | CH | O | H | 4-Cl—C₆H₄ | 8.01(s, 1H), 7.60(s, 1H), 7.59~6.92(m, 12H), 5.19(s, 2H), 3.79(s, 3H), 3.64(s, 3H) | 563 (26), 285 (25), 149 (60), 111 (49), 57 (100) |
| 118 | CH | O | H | 4-Br—C₆H₄ | 8.06(s, 1H), 7.61(s, 1H), 7.60~7.00(m, 12H), 5.18(s, 2H), 3.80(s, 3H), 3.70(s, 3H) | 607 (11), 221 (21), 205 (89), 190 (38), 145 (100) |
| 119 | CH | O | H | 3,4-OCH₂O—C₆H₃ | 8.00(s, 1H), 7.61(s, 1H), 7.60~6.81(m, 11H), 5.86(s, 2H), 5.19(s, 2H), 3.80(s, 3H), 3.64(s, 3H) | 573 (20), 189 (73), 145 (100) |
| 120 | CH | NH | H | C₆H₅ | 8.01(s, 1H), 7.62(s, 1H), 7.61~7.00(m, 13H), 5.18(s, 2H), 4.17(b, 1H), 3.63(s, 3H), 2.98(d, 3H) | 528 (54), 188 (53), 144 (100), 103 (36), 76 (46) |
| 121 | CH | NH | H | 4-CH₃—C₆H₄ | 8.00(s, 1H), 7.61(s, 1H), 7.59~7.02(m, 12H), 5.18(s, 2H), 4.16(b, 1H), 3.64(s, 3H), 2.97(d, 3H), 2.37(s, 3H) | 542 (49), 188 (51), 84 (100), 47 (66) |
| 122 | CH | NH | H | 3,5-(CH₃)₂—C₆H₃ | 8.06(s, 1H), 7.62(s, 1H), 7.60~6.81(m, 11H), 5.18(s,2H),4.18(b, 1H),3.61(s, 3H), 2.37(s, 3H) | 556 (81), 405 (25), 188 (49), 111 (52), 83 (46), 57 (100) |
| 123 | CH | NH | H | 4-C₂H₅—C₆H₄ | 8.02(s, 1H), 7.62(s, 1H), 7.60~7.08(m, 12H), 5.20(s, 2H), 4.15(b, 1H), 3.61(s, 3H), 3.00(d, 3H), 2.61(q, 2H), 1.21(t, 3H) | 556 (38), 188 (100), 144 (70) |
| 124 | CH | NH | H | 4-n-C₄H₉—C₆H₄ | 8.00(s, 1H), 7.62(s, 1H), 7.61~7.01(m, 12H), 5.19(s, 2H), 4.14(b, 1H), 3.60(s, 3H), 2.97(d, 3H), 2.60(t, 2H), 1.64~1.25(m, 4H), 0.93(t, 3H) | 584 (48), 188 (100), 144 (49) |

TABLE 8-continued

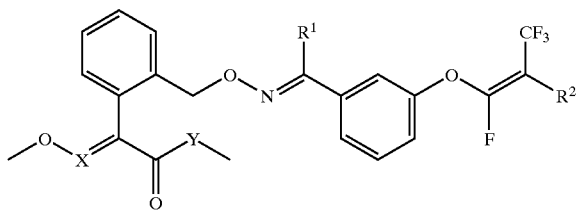

| Ex. No. | X | Y | R¹ | R² | ¹H-NMR(CDCl₃, TMS)δ (ppm) | MS (m/e) (M, int) |
|---|---|---|---|---|---|---|
| 125 | CH | NH | H | 3-CH₃O—C₆H₄ | 8.05(s, 1H), 7.62(s, 1H), 7.61~7.01(m, 12H), 5.17(s, 2H), 4.16(b, 1H), 3.76(s, 3H), 3.62(s, 3H), 2.94(d, 3H) | 558 (48), 188 (100), 144 (45), 115 (30) |
| 126 | CH | NH | H | 4-CH₃O—C₆H₄ | 8.01(s, 1H), 7.61(s, 1H), 7.60~7.05(m, 12H), 5.18(s, 2H), 4.17(b, 1H), 3.78(s, 3H), 3.61(s, 3H), 2.98(d, 3H) | 558 (47), 188 (100), 144 (71) |
| 127 | CH | NH | H | 3-F—C₆H₄ | 8.00(s, 1H), 7.62(s, 1H), 7.60~7.06(m, 12H), 5.19(s, 2H), 4.17(b, 1H), 3.61(s, 3H), 2.91(d, 3H) | 546 (38), 188 (100), 144 (42), 76 (22) |
| 128 | CH | NH | H | 3-CF₃—C₆H₄ | 8.00(s, 1H), 7.62(s, 1H), 7.61~7.08(m, 12H), 5.20(s, 2H), 4.19(b, 1H), 3.62(s, 3H), 2.90(d, 3H) | 596 (51), 188 (100), 144 (66), 76 (25) |
| 129 | CH | NH | H | 4-CF₃—C₆H₄ | 8.03(s, 1H), 7.61(s, 1H), 7.60~7.10(m, 12H), 5.17(s, 2H), 4.17(b, 1H), 3.61(s, 3H), 2.91(d, 3H) | 596 (42), 188 (100), 144 (49), 76 (23) |
| 130 | CH | NH | H | 3-Cl—C₆H₄ | 8.01(s, 1H), 7.60(s, 1H), 7.54~7.12(m, 12H), 5.18(s, 2H), 4.16(b, 1H), 3.62(s, 3H), 2.93(d, 3H) | 562 (48), 188 (100), 144 (55), 76 (18) |
| 131 | N | O | H | C₆H₅ | 7.97(s, 1H), 7.58~6.97(m, 13H), 5.10(s, 2H), 4.01(s, 3H), 3.80(s, 3H) | 530 (27), 221 (45), 131 (46), 116 (100), 59 (85) |
| 132 | N | O | H | 4-CH₃—C₆H₄ | 7.99(s, 1H), 7.57~6.96(m, 12H), 5.12(s, 2H), 4.02(s, 3H), 3.82(s, 3H), 2.34(s, 3H) | 544 (46), 116 (77), 59 (100) |
| 133 | N | O | H | 3,5-(CH₃)₂—C₆H₃ | 7.97(s, 1H), 7.56~6.87(m, 11H), 5.10(s, 2H), 4.01(s, 3H), 3.81(s, 3H), 2.27(s, 6H) | 558 (32), 116 (78), 59 (100) |
| 134 | N | O | H | 3-CH₃O—C₆H₄ | 7.98(s, 1H), 7.58~6.81(m, 12H), 5.09(s, 2H), 4.00(s, 3H), 3.81(s, 3H), 3.74(s, 3H) | 560 (38), 131 (54), 116 (100), 59 (49) |
| 135 | N | O | H | 4-F—C₆H₄ | 7.97(s, 1H), 7.57~6.93(m, 12H), 5.10(s, 2H), 4.00(s, 3H), 3.80(s, 3H) | 548 (22), 116 (44), 59 (100) |
| 136 | N | O | H | 4-CF₃—C₆H₄ | 7.98(s, 1H), 7.71~6.95(m, 12H), 5.10(s, 2H), 4.01(s, 3H), 3.81(s, 3H) | 598 (41), 131 (52), 116 (97), 59 (100) |
| 137 | N | O | H | 3-Cl—C₆H₄ | 7.98(s, 1H), 7.56~6.92(m, 12H), 5.11(s, 2H), 4.01(s, 3H), 3.81(s, 3H) | 564 (34), 131 (45), 116 (100), 59 (67) |
| 138 | N | O | H | 3,4-OCH₂O—C₆H₃ | 7.97(s, 1H), 7.57~6.78(m, 11H), 5.94(s, 2H), 5.09(s, 2H), 4.01(s, 3H), 3.80(s, 3H) | 574 (42), 116 (41), 59 (100) |
| 139 | N | NH | H | C₆H₅ | 7.97(s, 1H), 7.51~6.96(m, 13H), 6.76(b, 1H), 5.09(s, 2H), 3.92(s, 3H), 2.86(d, 3H) | 529 (29), 221 (43), 132 (79), 116 (89), 58 (100) |
| 140 | N | NH | H | 3-CH₃—C₆H₄ | 7.98(s, 1H), 7.58~6.93(m, 12H), 6.78(b, 1H), 5.12(s, 2H), 3.94(s, 3H), 2.84(d, 3H), 2.32(s, 3H) | 543 (51), 221 (96), 205 (42), 132 (94), 116 (100), 58 (71) |
| 141 | N | NH | H | 3,5-(CH₃)₂—C₆H₃ | 7.99(s, 1H), 7.58~6.89(m, 11H), 6.73(b, 1H), 5.10(s, 2H), 3.95(s, 3H), 2.83(d, 3H), 2.32(s, 6H) | 557 (76), 221 (88), 205 (47), 132 (97), 116 (98), 58 (100) |
| 142 | N | NH | H | 4-n-C₄H₉—C₆H₄ | 7.98(s, 1H), 7.54~6.89(m, 12H), 6.76(b, 1H), 5.10(s, 2H), 3.95(s, 3H), 2.83(d, 3H), 2.61(t, 2H), 1.64~1.21(m, 4H), 0.91(t, 3H) | 585 (73), 221 (98), 205 (61), 132 (100), 116 (63), 58 (88) |
| 143 | N | NH | H | 3-CH₃O—C₆H₄ | 7.97(s, 1H), 7.50~6.80(m, 12H), 6.76(b, 1H), 5.10(s, 2H), 3.93(s, 3H), 3.74(s, 3H), 2.84(d, 3H) | 559 (89), 338 (41), 221 (98), 205 (45), 132 (90), 58(100) |
| 144 | N | NH | H | 4-C₂H₅O—C₆H₄ | 7.97(s, 1H), 7.51~6.80(m, 12H), 6.75(b, 1H), 5.10(s, 2H), 4.01(q, 2H), 3.93(s, 3H), 2.88(d, 3H), 1.41(t, 3H) | 573 (67), 221 (79), 205 (45), 132 (93), 116 (93), 58 (100) |
| 145 | N | NH | H | 4-F—C₆H₄ | 7.98(s, 1H), 7.57~6.94(m, 12H), 6.74(b, 1H), 5.11(s, 2H), 3.94(s, 3H), 2.84(d, 3H) | 547 (43), 221 (85), 132 (81), 116 (86), 58 (100) |
| 146 | N | NH | H | 3-CF₃—C₆H₄ | 7.97(s, 1H), 7.72~6.92(m, 12H), 6.78(b, 1H), 5.11(s, 2H), 3.94(s, 3H), 2.84(d, 3H) | 597 (62), 221 (59), 132 (71), 116 (85), 58 (100) |
| 147 | N | NH | H | 4-CF₃—C₆H₄ | 7.95(s, 1H), 7.74~6.90(m, 12H), 6.75(b, 1H), 5.11(s, 2H), 3.95(s, 3H), 2.83(d, 3H) | 597 (83), 221 (81), 132 (84), 116 (83), 58 (100) |
| 148 | N | NH | H | 3-Cl—C₆H₄ | 7.96(s, 1H), 7.56~6.92(m, 12H), 6.74(b, 1H), 5.09(s, 2H), 3.96(s, 3H), 2.82(d, 3H) | 563 (71), 221 (100), 132 (71), 58 (67) |
| 149 | N | NH | H | 3,4-OCH₂O—C₆H₃ | 7.97(s, 1H), 7.58~6.80(m, 11H), 6.73(b, 1H), 5.94(s, 2H), 5.10(s, 2H), 3.96(s, 3H), 2.84(d, 3H) | 573 (36), 221 (42), 205 (45), 176 (77), 132 (86), 116 (100) |
| 150 | CH | O | CH₃ | C₆H₅ | 7.57(s, 1H), 7.54~6.92(m, 13H), 5.14(s, 2H), 3.74(s, 3H), 3.67(s, 3H), 2.18(s, 3H) | 543 (19), 205 (43), 189 (44), 145 (100) |

TABLE 8-continued

| Ex. No. | X | Y | R¹ | R² | ¹H-NMR(CDCl₃, TMS)δ (ppm) | MS (m/e) (M, int) |
|---|---|---|---|---|---|---|
| 151 | CH | O | CH₃ | 3-CH₃—C₆H₄ | 7.56(s, 1H), 7.54~7.00(m, 12H), 5.16(s, 2H), 3.77(s, 3H), 3.71(s, 3H), 2.28(s, 3H), 2.17(s, 3H) | 557 (31), 336 (57), 205 (39), 189 (29), 145 (100) |
| 152 | CH | O | CH₃ | 4-CH₃—C₆H₄ | 7.57(s, 1H), 7.54~6.98(m, 12H), 5.17(s, 2H), 3.77(s, 3H), 3.68(s, 3H), 2.26(s, 3H), 2.17(s, 3H) | 557 (47), 336 (71), 205 (37), 189 (39), 145 (100) |
| 153 | CH | O | CH₃ | 3,4-(CH₃)₂—C₆H₃ | 7.59(s, 1H), 7.58~6.97(m, 11H), 5.18(s, 2H), 3.74(s, 3H), 3.67(s, 3H), 2.26(s, 3H), 2.24(s, 6H) | 571 (26), 553 (55), 480 (61), 350 (34), 205 (87), 145(100) |
| 154 | CH | O | CH₃ | 3,5-(CH₃)₂—C₆H₃ | 7.45(s, 1H), 7.42~6.79(m, 11H), 5.04(s, 2H), 3.61(s, 3H), 3.52(s, 3H), 2.20(s, 3H), 2.17(s, 3H), 2.08(s, 3H) | 571 (12), 205 (28), 145 (100), 117 (14), 103 (18) |
| 155 | CH | O | CH₃ | 4-C₂H₅—C₆H₄ | 7.61(s, 1H), 7.60~7.01(m, 12H), 5.21(s, 2H), 3.76(s, 3H), 3.71(s, 3H), 2.67(q, 2H), 2.21(s, 3H), 1.28(t, 3H) | 571 (11), 350 (21), 205 (99), 145(100) |
| 156 | CH | O | CH₃ | 4-n-C₄H₉C₆H₄ | 7.61(s, 1H), 7.60~7.00(m, 12H), 5.21(s,2H), 3.75(s, 3H), 3.70(s, 3H), 2.65(t, 2H), 2.21(s, 3H), 1.75~1.26(m, 4H), 0.98(t, 3H) | 599 (34), 582 (36), 508 (31), 205 (100), 145 (30) |
| 157 | CH | O | CH₃ | 3-CH₃O—C₆H₄ | 7.62(s, 1H), 7.61~6.86(m, 12H), 5.20(s, 2H), 3.79(s, 3H), 3.79(s, 3H), 3.71(s, 3H), 2.21(s, 3H) | 573 (16), 352 (28), 205 (96), 190 (27), 145 (100) |
| 158 | CH | O | CH₃ | 4-CH₃O—C₆H₄ | 7.60(s, 1H), 7.58~6.84(m, 12H), 5.21(s, 2H), 3.81(s, 3H), 3.75(s, 3H), 3.70(s, 3H), 2.21(s, 3H) | 573 (12), 352 (12), 205 (38), 145(100), 103 (23) |
| 159 | CH | O | CH₃ | 3-F—C₆H₄ | 7.65(s, 1H), 7.63~6.94(m, 12H), 5.20(s, 2H), 3.79(s, 3H), 3.69(s, 3H), 2.21(s, 3H) | 561 (31), 543 (54), 470 (67), 340 (24), 205 (97), 145 (100) |
| 160 | CH | O | CH₃ | 4-F—C₆H₄ | 7.63(s, 1H), 7.62~6.98(m, 12H), 5.23(s, 2H), 3.78(s, 3H), 3.70(s, 3H), 2.25(s, 3H) | 561 (13), 340 (24), 205 (87), 145(100) |
| 161 | CH | O | CH₃ | 4-CF₃—C₆H₄ | 7.60(s, 1H), 7.63~6.98(m, 12H), 5.18(s, 2H), 3.78(s, 3H), 3.68(s, 3H), 2.20(s, 3H) | 611 (51), 593 (32), 391 (27), 205 (48), 189 (43), 145(100) |
| 162 | CH | O | CH₃ | 3-Cl—C₆H₄ | 7.58(s, 1H), 7.56~6.97(m, 12H), 5.17(s, 2H), 3.77(s, 3H), 3.67(s, 3H), 2.16(s, 3H) | 577 (30), 356 (10), 205 (49), 189 (42), 145 (100) |
| 163 | CH | O | CH₃ | 4-Cl—C₆H₄ | 7.59(s, 1H), 7.56~6.95(m, 12H), 5.16(s, 2H), 3.76(s, 3H), 3.66(s, 3H), 2.17(s, 3H) | 577 (38), 356 (36), 205 (24), 189 (39), 145 (100), 77 (21) |
| 164 | CH | O | CH₃ | 3,5-Cl₂—C₆H₃ | 7.61(s, 1H), 7.60~7.00(m, 11H), 5.19(s, 2H), 3.80 (s, 3H), 3.70(s, 3H), 2.23(s, 3H) | 611 (28), 520 (30), 205 (94), 190 (32), 173 (22), 145 (100) |
| 165 | CH | O | CH₃ | 4-Br—C₆H₄ | 7.60(s, 1H), 7.59~6.97(m, 12H), 5.20(s, 2H), 3.79(s, 3H), 3.71(s, 3H), 2.24(s, 3H) | 621 (15), 400 (13), 205 (86), 189 (46), 145 (100) |
| 166 | CH | O | CH₃ | 3,4-OCH₂O—C₆H₃ | 7.59(s, 1H), 7.57~6.78(m, 11H), 5.87(s, 2H), 5.19(s, 2H), 3.79(s, 3H), 3.65(s, 3H), 2.20(s, 3H) | 587 (31), 205 (75), 189 (29), 145 (100) |
| 167 | CH | NH | CH₃ | C₆H₅ | 7.56(s, 1H), 7.53~6.78(m, 13H), 5.15(s, 2H), 4.31(b, 1H), 3.63(s, 3H), 2.81(d, 3H), 2.22(s, 3H) | 542 (34), 354 (26), 188 (100), 144 (94) |
| 168 | CH | NH | CH₃ | 4-CH₃—C₆H₄ | 7.60(s, 1H), 7.57~6.94(m, 12H), 5.17(s, 2H), 4.28(b, 1H), 3.62(s, 3H), 2.83(d, 3H), 2.38(s, 3H), 2.22(s, 3H) | 556 (42), 336 (43), 188 (100), 144 (56) |
| 169 | CH | NH | CH₃ | 4-C₂H₅—C₆H₄ | 7.61(s, 1H), 7.59~6.78(m, 12H), 5.18(s, 2H), 4.25(b, 1H), 3.61(s, 3H), 2.93(d, 3H), 2.67(q, 2H), 2.23(s, 3H), 1.24(t, 3H) | 570 (16), 188 (100), 144 (48) |
| 170 | CH | NH | CH₃ | 4-n-C₄H₉—C₆H₄ | 7.61(s, 1H), 7.60~6.92(m, 12H), 5.18(s, 2H), 4.27(b, 1H), 3.61(s, 3H), 2.87(d, 3H), 2.61(t, 2H), 2.34(s, 3H), | 598 (20), 188 (100), 144 (53) |
| 171 | CH | NH | CH₃ | 3-CH₃O—C₆H₄ | 7.62(s, 1H), 7.60~6.80(m, 12H), 5.20(s, 2H), 4.23(b, 1H), 3.80(s, 3H), 3.61(s, 3H), 2.93(d, 3H), 2.21(s, 3H) | 572 (39), 188 (100), 144 (70) |
| 172 | CH | NH | CH₃ | 4-CH₃O—C₆H₄ | 7.60(s, 1H), 7.58~6.81(m, 12H), 5.19(s, 2H), 4.24(b, 1H), 3.81(s, 3H), 3.62(s, 3H), 2.91(d, 3H), 2.22(s, 3H) | 572 (23), 188 (45), 144 (29), 84 (100) |

TABLE 8-continued

| Ex. No. | X | Y | R¹ | R² | ¹H-NMR(CDCl₃, TMS)δ (ppm) | MS (m/e) (M, int) |
|---|---|---|---|---|---|---|
| 173 | N | O | CH₃ | C₆H₅ | 7.47~7.21(m, 13H), 5.12(s, 2H), 4.01(s, 3H), 3.78(s, 3H), 2.15(s, 3H) | 544 (24), 222 (43), 131 (60), 116 (100), 59 (49) |
| 174 | N | O | CH₃ | 3-CH₃—C₆H₄ | 7.49~6.97(m, 12H), 5.12(s, 2H), 4.00(s, 3H), 3.79(s, 3H), 2.31(s, 3H), 2.14(s, 3H) | 558 (36), 222 (40), 131 (64), 116 (100), 59 (41) |
| 175 | N | O | CH₃ | 4-CH₃—C₆H₄ | 7.47~6.99(m, 12H), 5.13(s, 2H), 4.01(s, 3H), 3.78(s, 3H), 2.32(s, 3H), 2.15(s, 3H) | 558 (31), 222 (41), 131 (62), 116(100), 59 (42) |
| 176 | N | O | CH₃ | 3,4-(CH₃)₂—C₆H₃ | 7.45~6.92(m, 11H), 5.12(s, 2H), 3.99(s, 3H), 3.76(s, 3H), 2.32(s, 3H), 2.26(s, 3H), 2.14(s, 3H) | 572 (21), 206 (46), 131 (66), 115 (100) |
| 177 | N | O | CH₃ | 3,5-(CH₃)₂—C₆H₃ | 7.47~6.93(m, 11H), 5.11(s, 2H), 4.00(s, 3H), 3.79(s, 3H), 2.33(s, 3H), 2.27(s, 3H), 2.15(s, 3H) | 572 (28), 206 (52), 131 (72), 115 (100) |
| 178 | N | O | CH₃ | 4-C₂H₅—C₆H₄ | 7.50~6.97(m, 12H), 5.12(s, 2H), 4.00(s, 3H), 3.78(s, 3H), 2.62(q, 2H), 2.14(s, 3H), 1.22(t, 3H) | 572 (18), 222 (49), 206 (57), 131 (69), 116 (100), 83 (94) |
| 179 | N | O | CH₃ | 4-n-C₄H₉C₆H₄ | 7.48~6.95(m, 12H), 5.11(s, 2H), 3.99(s, 3H), 3.77(s, 3H), 2.61(t, 2H), 2.13(s, 3H), 1.61~1.24(m, 4H), 0.92(t, 3H) | 600 (15), 206 (67), 131 (61), 116 (100), 83 (76), 58 (81) |
| 180 | N | O | CH₃ | 3-CH₃O—C₆H₄ | 7.52~6.86(m, 12H), 5.14(s, 2H), 4.02(s, 3H), 3.82(s, 3H), 3.80(s, 3H), 2.17(s, 3H) | 574 (34), 222 (43), 131 (63), 116 (100) |
| 181 | N | O | CH₃ | 4-CH₃O—C₆H₄ | 7.48~6.80(m, 12H), 5.10(s, 2H), 3.97(s, 3H), 3.77(s, 3H), 3.72(s, 3H), 2.12(s, 3H) | 574 (16), 206 (47), 131 (69), 115 (100), 59 (53) |
| 182 | N | O | CH₃ | 3-F—C₆H₄ | 7.49~6.97(m, 12H), 5.14(s, 2H), 4.02(s, 3H), 3.80(s, 3H), 2.17(s, 3H) | 562 (24), 222 (48), 131 (67), 116 (100), 59 (51) |
| 183 | N | O | CH₃ | 4-F—C₆H₄ | 7.50~6.98(m, 12H), 5.12(s, 2H), 4.00(s, 3H), 3.79(s, 3H), 2.16(s, 3H) | 562 (41), 222 (51), 131 (67), 116 (100) |
| 184 | N | O | CH₃ | 3-Cl—C₆H₄ | 7.53~7.00(m, 12H), 5.13(s, 2H), 4.01(s, 3H), 3.78(s, 3H), 2.15(s, 3H) | 578 (53), 222 (47), 131 (64), 116 (100) |
| 185 | N | O | CH₃ | 4-Cl—C₆H₄ | 7.50~6.96(m, 12H), 5.15(s, 2H), 4.00(s, 3H), 3.80(s, 3H), 2.17(s, 3H) | 578 (37), 131 (60), 116 (100), 59 (60) |
| 186 | N | O | CH₃ | 3,5-Cl₂—C₆H₃ | 7.51~6.97(m, 11H), 5.14(s, 2H), 4.02(s, 3H), 3.81(s, 3H), 2.18(s, 3H) | 612 (31), 222 (67), 131 (76), 116 (100), 59 (60) |
| 187 | N | O | CH₃ | 4-Br—C₆H₄ | 7.59~6.96(m, 12H), 5.13(s, 2H), 4.01(s, 3H), 3.80(s, 3H), 2.16(s, 3H) | 622 (26), 222 (79), 206 (56), 130 (100), 115 (89) |
| 188 | N | O | CH₃ | 3-CF₃—C₆H₄ | 7.72~6.95(m, 12H), 5.14(s, 2H), 4.02(s, 3H), 3.80(s, 3H), 2.15(s, 3H) | 612 (24), 131 (55), 116 (100), 105 (93), 83 (97) |
| 189 | N | O | CH₃ | 4-CF₃—C₆H₄ | 7.66~7.00(m, 12H), 5.13(s, 2H), 4.01(s, 3H), 3.79(s, 3H), 2.16(s, 3H) | 612 (31), 131 (58), 116 (100), 59 (64) |
| 190 | N | O | CH₃ | 3,4-OCH₂O—C₆H₃ | 7.49~6.78(m, 11H), 6.77(s, 2H), 5.14(s, 2H), 4.03(s, 3H), 3.80(s, 3H), 2.17(s, 3H) | 588 (43), 131 (63), 116 (100), 59 (97) |
| 191 | N | NH | CH₃ | C₆H₅ | 7.52~6.97(m, 13H), 6.73(b, 1H), 5.14(s, 2H), 3.94(s, 3H), 2.84(d, 3H), 2.16(s, 3H) | 543 (35), 221 (83), 132 (88), 116 (100), 58 (82) |
| 192 | N | NH | CH₃ | 4-CH₃—C₆H₄ | 7.53~6.96(m, 12H), 6.72(b, 1H), 5.13(s, 2H), 3.95(s, 3H), 2.85(d, 3H), 2.39(s, 3H), 2.17(s, 3H) | 557 (27), 221 (88), 205 (54), 116 (100), 58 (80) |
| 193 | N | NH | CH₃ | 3,4-(CH₃)₂—C₆H₃ | 7.51~6.98(m, 11H), 6.74(b, 1H), 5.14(s, 2H), 3.94(s, 3H), 2.84(d, 3H), 2.37(s, 6H), 2.15(s, 3H) | 571 (34), 221 (60), 205 (52), 132 (86), 116 (100), 58 (76) |
| 194 | N | NH | CH₃ | 3,5-(CH₃)₂—C₆H₃ | 7.59~6.94(m, 11H), 6.81(b, 1H), 5.18(s, 2H), 3.64(s, 3H), 3.80(d, 3H), 2.38(s, 3H), 2.33(s, 3H), 2.20(s, 3H) | 571 (43), 221 (50), 205 (38), 132 (100), 116 (95), 58 (46) |
| 195 | N | NH | CH₃ | 4-C₂H₅—C₆H₄ | 7.50~6.97(m, 12H), 6.73(b, 1H), 5.12(s, 2H), 3.92(s, 3H), 2.83(d, 3H), 2.64(q, 2H), 2.14(s, 3H), 1.21(t, 3H) | 571 (27), 221 (77), 205 (55), 132 (91), 116 (100), 58 (91) |
| 196 | N | NH | CH₃ | 4-n-C₄H₉—C₆H₄ | 7.53~7.02(m, 12H), 6.77(b, 1H), 5.18(s, 2H), 3.91(s, 3H), 2.80(d, 3H), 2.60(t, 2H), 2.18(s, 3H), 1.64~1.20(m, 4H), 0.89(t, 3H) | 599 (21), 221 (55), 132 (100), 116 (81), 58 (41) |

TABLE 8-continued

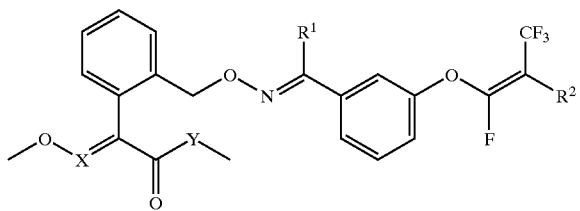

| Ex. No. | X | Y | R¹ | R² | ¹H-NMR(CDCl₃, TMS)δ (ppm) | MS (m/e) (M, int) |
|---|---|---|---|---|---|---|
| 197 | N | NH | CH₃ | 3-CH₃O—C₆H₄ | 7.48~6.82(m, 12H), 6.74(b, 1H), 5.11(s, 2H), 3.91(s, 3H), 3.74(s, 3H), 2.82(d, 3H), 2.13(s, 3H) | 573 (31), 221 (87), 205 (50), 132 (87), 116 (100), 58 (84) |
| 198 | N | NH | CH₃ | 4-CH₃O—C₆H₄ | 7.51~6.80(m, 12H), 6.68(b, 1H), 5.09(s, 2H), 3.89(s, 3H), 3.74(s, 3H), 2.81(d, 3H), 2.11(s,3H) | 573 (14), 221 (83), 205 (63), 132 (80), 116 (100) |
| 199 | N | NH | CH₃ | 4-F—C₆H₄ | 7.47~6.93(m, 12H), 6.72(b, 1H), 5.12(s, 2H), 3.93(s, 3H), 2.87(d, 3H), 2.15(s, 3H) | 561 (42), 221 (49), 132 (77), 116 (100), 58 (97) |
| 200 | N | NH | CH₃ | 3-CF₃—C₆H₄ | 7.65~6.95(m, 12H), 6.73(b, 1H), 5.11(s, 2H), 3.93(s, 3H), 2.85(d, 3H), 2.14(s, 3H) | 611 (33), 221 (94), 205 (60), 132 (97), 116 (100), 58 (65) |
| 201 | N | NH | CH₃ | 3-Cl—C₆H₄ | 7.48~6.93(m, 12H), 6.74(b, 1H), 5.12(s, 2H), 3.94(s, 3H), 2.84(d, 3H), 2.16(s, 3H) | 577 (37), 221 (72), 205 (49), 132 (77), 116 (100), 58 (76) |
| 202 | CH | O | CF₃ | C₆H₅ | 7.51(s, 1H), 7.45~7.00(m, 13H), 5.18(s, 2H), 3.68(s, 3H), 3.56(s, 3H) | 597 (51), 205 (50), 189 (87), 145 (100), 131 (34), 103 (37) |
| 203 | CH | O | CF₃ | 3-CH₃—C₆H₄ | 7.52(s, 1H), 7.51~7.03(m, 12H), 5.18(s, 2H), 3.68(s, 3H), 3.59(s, 3H), 2.38(s, 3H) | 611 (39), 205 (31), 189 (57), 145 (100) |
| 204 | CH | O | CF₃ | 4-CH₃—C₆H₄ | 7.51(s, 1H), 7.37~6.86(m, 12H), 5.17(s, 2H), 3.67(s, 3H), 3.56(s, 3H), 2.36(s, 3H), | 611 (46), 205 (41), 189 (100), 145 (93) |
| 205 | CH | O | CF₃ | 3,4-(CH₃)₂—C₆H₃ | 7.53(s, 1H), 7.52~6.98(m, 11H), 5.17(s, 2H), 3.69(s, 3H), 3.60(s, 3H), 2.28(s, 3H), 2.22(s, 3H) | 625 (21), 205 (39), 188 (75), 144 (100) |
| 206 | CH | O | CF₃ | 3,5-(CH₃)₂—C₆H₃ | 7.54(s, 1H), 7.52~6.85(m, 11H), 5.19(s, 2H), 3.68(s, 3H), 3.58(s, 3H), 2.28(s, 6H) | 625 (13), 221 (50), 205 (97), 190 (60), 173 (20), 145 (100) |
| 207 | CH | O | CF₃ | 4-C₂H₅—C₆H₄ | 7.50(s, 1H), 7.49~7.00(m, 12H), 5.20(s, 2H), 3.66(s, 3H), 3.52(s, 3H), 2.61(q, 2H), 1.13(t, 3H) | 625 (54), 222 (21), 205 (73), 190 (32), 145 (100) |
| 208 | CH | O | CF₃ | 4-n-C₄H₉—C₆H₄ | 7.55(s, 1H), 7.53~7.01(m, 12H), 5.21(s, 2H), 3.68(s, 3H), 3.57(s, 3H), 2.64(t, 2H), 1.76~1.19(m, 4H), 0.97(t, 3H) | 653 (30), 207 (15), 189 (98), 145 (100) |
| 209 | CH | O | CF₃ | 3-CH₃O—C₆H₄ | 7.52(s, 1H), 7.51~6.79(m, 12H), 5.18(s, 2H), 3.79(s, 3H), 3.74(s, 3H), 3.58(s, 3H) | 627 (22), 188 (79), 145 (100) |
| 210 | CH | O | CF₃ | 4-CH₃O—C₆H₄ | 7.46(s, 1H), 7.44~6.78(m, 12H), 5.08(s, 2H), 3.57(s, 3H), 3.56(s, 3H), 3.48(s, 3H) | 627 (31), 337 (61), 205 (33), 189 (56), 145 (100) |
| 211 | CH | O | CF₃ | 3-F—C₆H₄ | 7.50(s, 1H), 7.49~7.91(m, 12H), 5.20(s, 2H), 3.66(s, 3H), 3.54(s, 3H) | 615 (53), 221 (94), 206 (40), 189 (95), 173 (47), 145 (100) |
| 212 | CH | O | CF₃ | 4-F—C₆H₄ | 7.51(s, 1H), 7.48~6.86(m, 12H), 5.17(s, 2H), 3.68(s, 3H), 3.54(s, 3H) | 615 (24), 221 (37), 205 (98), 190 (60), 145 (100) |
| 213 | CH | O | CF₃ | 3-CF₃—C₆H₄ | 7.55(s, 1H), 7.54~7.04(m, 12H), 5.18(s, 2H), 3.69(s, 3H), 3.58(s, 3H) | 665 (19), 189 (86), 145 (100) |
| 214 | CH | O | CF₃ | 4-CF₃—C₆H₄ | 7.53(s, 1H), 7.52~7.07(m, 12H), 5.17(s, 2H), 3.70(s, 3H), 3.58(s, 3H) | 665 (12), 189 (84), 145 (100) |
| 215 | CH | O | CF₃ | 3-Cl—C₆H₄ | 7.54(s, 1H), 7.53~7.08(m, 12H), 5.19(s, 2H), 3.70(s, 3H), 3.59(s, 3H) | 631 (32), 205 (46), 189 (100), 145 (72) |
| 216 | CH | O | CF₃ | 4-Cl—C₆H₄ | 7.43(s, 1H), 7.40~6.91(m, 12H), 5.07(s, 2H), 3.59(s, 3H), 3.47(s, 3H) | 631 (27), 273 (26), 253 (23), 84 (100), 43 (66) |
| 217 | CH | O | CF₃ | 3,5-Cl₂—C₆H₃ | 7.50(s, 1H), 7.49~6.94(m, 11H), 5.19(s, 2H), 3.69(s, 3H), 3.57(s, 3H) | 665 (29), 221 (32), 189 (89), 161 (22), 145 (100) |
| 218 | CH | O | CF₃ | 4-Br—C₆H₄ | 7.53(s, 1H), 7.52~6.97(m, 12H), 5.18(s, 2H), 3.67(s, 3H), 3.56(s, 3H) | 675 (21), 387 (22), 221 (32), 198 (95), 173 (26), 145 (100) |
| 219 | CH | O | CF₃ | 3,4-OCH₂O—C₆H₃ | 7.53(s, 1H), 7.52~6.71(m, 11H), 5.91(s, 2H), 5.20(s, 2H), 3.69(s, 3H), 3.59(s, 3H) | 641 (18), 188 (50), 144 (100) |
| 220 | CH | NH | CF₃ | 4-Cl—C₆H₄ | 7.97(s, 1H), 7.67~6.78(m, 12H), 5.19(s, 2H), 4.10(b, 1H), 3.74(s, 3H), 2.81(d, 3H) | 630 (51), 408 (45), 188 (100), 144 (57) |
| 221 | N | O | CF₃ | C₆H₅ | 7.52~7.00(m, 13H), 5.15(s, 2H), 3.91(s, 3H), 3.71(s, 3H) | 598 (43), 376 (45), 222 (81), 206 (45), 131 (63), 116 (100) |

TABLE 8-continued

[Structure: benzene ring with -O-N= group, attached to another benzene ring with R¹, -O- linkage to =C(CF₃)-C(F)=R², and a methoxyimino acrylate group with X and Y substituents]

| Ex. No. | X | Y | R¹ | R² | ¹H-NMR(CDCl₃, TMS)δ (ppm) | MS (m/e) (M, int) |
|---------|---|---|-----|-----|---------------------------|-------------------|
| 222 | N | O | CF₃ | 3-CH₃—C₆H₄ | 7.54~6.97(m, 12H), 5.17(s, 2H), 3.98(s, 3H), 3.76(s, 3H), 2.32(s, 3H) | 612 (42), 222 (20), 206 (74), 131 (67), 116 (100), 59 (49) |
| 223 | N | O | CF₃ | 4-Cl—C₆H₄ | 7.41~6.87(m, 12H), 5.05(s, 2H), 3.84(s, 3H), 3.61(s, 3H) | 632 (32), 222 (56), 206 (50), 131 (76), 116 (100), 59 (53) |
| 224 | N | NH | CF₃ | 4-Cl—C₆H₄ | 7.84(b, 1H), 7.56~6.80(m, 12H), 5.12(s, 2H), 3.96(s, 3H), 2.87(s, 3H) | 631 (48), 205 (28), 137 (26), 116 (75), 58 (100) |

Fungicidal Activity Test

To examine fungicidal activity of the compounds of the present invention, each of the compounds listed in Table 3 and 4 was dissolved in 10% acetone to a concentration of 250 ppm, and Tween-20 was added thereto to a concentration of 250 or 500 ppm. 50 ml of the resulting solution was sprayed on leaves of a host plant. The plant was kept at room temperature for 24 hours to let the solvent evaporate, and then, a pathogenic fungus was inoculated thereonto. The plant was held in a humidity chamber for 24 hours, transferred to an plant growth room kept at 20 to 27° C. and a relative humidity of 60 to 80% and kept to induce disease. Subsequently, the lesion area (L.A.) attacked by the pathogenic fungus was measured according to a method of Cho(Cho, K. Y., Search Report by Korea Research Institute of Chemical Technology(1989))". This procedure was repeated twice for each test. 10% Acetone solution containing 250 ppm of Tween-20 was used as a control.

The fungicidal activity of the compound of the present invention is repressed by a control value (C.V.) calculated as;

$$C.V. \ (\%) = \frac{L.A. \ of \ control - L.A. \ of \ test}{L.A. \ of \ control} \times 100$$

TEST EXAMPLE 1

Fungicidal Activity Against Rice Blast(RCB) Disease

*Pyricularia oryzae* Carvara KA301 was inoculated on a rice bran agar medium (rice bran 20 g, dextrose 10 g, agar 15 g and distilled water 1 l and cultured at 26° C. for 1 week. The surface of the medium was scratched using a rubber polishman to remove aerial mycelia, and cultured under a fluorescent light for 48 hours to form a spore. Spores were suspended in sterilized water at a concentration of 1×106 spore/ml. The spore suspension was sprayed enough to soak the leaves of a RBC disease-sensitive Nakdong rice plant having 3 or 4 leaves. The rice plant was held in a humidified dark room for 24 hours, transferred to an incubator kept at 24 to 28° C. and a relative humidity of more than 80% and kept for 5 days to induce RCB. L.A. on a fully grown leaf appearing underneath an uppermost leaf was measured to calculate an C.V.

TEST EXAMPLE 2

Fungicidal Activity Against Rice Sheath Blight (RSB) Disease

*Rhizoctonia solani* AG-1 was cultured on a PDA medium (potato 200 g, dextrose 20 g, agar 20 g and distilled water 1 ? for 3 days and the agar disc(diameter 0.6 cm) was inoculated and cultured on sterilized wheat bran medium in a 1 L bottle at 26 to 28° C. for 7 days. A mycelial mass was ground using a homogenizer, inoculated uniformly on soil of a pot wherein a Nakdong rice plant having 2 or 3 leaves and an height of 5 cm grew, and kept in humidity polyvinyl chamber for 5 days to induce RSB. L.A. on a leaf sheath was measured to calculate an C.V.

TEST EXAMPLE 3

Fungicidal Activity Against Cucumber Gray Mold Rot (CGM) Disease

*Botrytis cinerae*, which was isolated from cucumber infected thereby, was inoculated on a PDA agar medium and cultured under a 12L/12D cycle at 25° C. for 15 days to form spore. The spores were scraped, filtered through a gauze and then suspended in potato dextrose liquid medium at a concentration of 1×106 spore/ml. The spore suspension was sprayed on a cucumber plant having one leaf. The cucumber plant was held in a humidified room at 20° C. for 3 days. L.A. on a leaf was measured to calculate an C.V.

TEST EXAMPLE 4

Fungicidal Activity on Tomato Late Blight(TLB) Disease

*Phytophthora infestans* was cultured on a juice agar medium(V-8 juice 200 ml, CaCO₃ 4.5 g, agar 15 g and distilled water 800 ml) under a 16L/8D cycle at 20° C. for 14 days. Sterilized water was added thereto, the vessel was shaken to free zoospore sacs from the fungus mass and the zoospore sacs were collected using a four-layered gauze. A zoospore sac suspension having a concentration of 1×105 spore/ml was sprayed on a young tomato plant. The tomato plant was held in a humidified room at 20° C. for 24 hours, transferred to an incubator maintained at a temperature of 20° C. and a relative humidity of more than 80% for 4 days and cultured in to induce RBC. L.A. on primary and secondary leaves was measured to calculate an C.V.

TEST EXAMPLE 5

Fungicidal Activity Against Wheat Leaf Rust (WLR) Disease

*Puccinia recondita* was subcultured on a wheat plant in a laboratory. 15 g of wheat seeds was sowed in a pot diameter 6.5 cm) and cultured in a greenhouse for 7 days to obtain a wheat plant having only a primary leaf. The wheat plant was inoculated with spores by shaking thereover another plant infected thereby. The inoculated wheat plant was held in a humidified room at 20° C. for 24 hours, transferred to an incubator maintained at a temperature of 20° C. and a relative humidity of 70% and cultured for 10 days to induce WLR. L.A. on the primary leaf was measured to calculate an C.V.

TEST EXAMPLE 6

Fungicidal Activity Against Barley Powdery Mildew(BPM) Disease

*Erysiphae graminis* was subcultured on a wheat plant in a laboratory. 15 g of barley seeds was sowed in a pot (diameter 6.5 cm) and cultured in a greenhouse for 7 days to obtain a barley plant having only a primary leaf. The barley plant was inoculated with spores by shaking thereover another plant infected by BPM. The inoculated barley plant was cultured in an incubator maintained at a temperature of 22 to 24° C. and a relative humidity of 50% for 7 days to induce BPM. L.A. on the leaf was measured to calculate an C.V.

The results of subjecting the compounds of the present invention in Test example 1 to 6 at a concentration level of 250 ppm was more than 90% in most cases. Accordingly, these compounds having a C.V. of more than 90% were subjected to another series of tests at reduced concentration levels of 50, 10 and 2 ppm. The test results are shown in Table 9.

TABLE 9

Fungicidal Activities

| Compound No. | Concentration (ppm) | RCV | RSB | CGM | TLB | WLR | BPM |
|---|---|---|---|---|---|---|---|
| 1 | 50 | 100 | 65 | 69 | 12 | 100 | 100 |
|   | 10 | 86 | — | — | — | 100 | 100 |
|   | 2 | 71 | — | — | — | 96 | 99 |
| 2 | 50 | 93 | 60 | 17 | 85 | 100 | 100 |
|   | 10 | 86 | — | — | — | 100 | 99 |
|   | 2 | 33 | — | — | — | 97 | 98 |
| 3 | 50 | 100 | 60 | 46 | 84 | 100 | 100 |
|   | 10 | 80 | — | — | — | 98 | 99 |
|   | 2 | 0 | — | — | — | 96 | 86 |
| 5 | 50 | 41 | 55 | 17 | 28 | 100 | 100 |
|   | 10 | — | — | — | — | 100 | 100 |
|   | 2 | — | — | — | — | 96 | 98 |
| 6 | 50 | 99 | 75 | 44 | 33 | 100 | 100 |
|   | 10 | 58 | — | — | — | 100 | 99 |
|   | 2 | 8 | — | — | — | 98 | 97 |
| 9 | 50 | 100 | 50 | 53 | 12 | 100 | 100 |
|   | 10 | 83 | — | — | — | 98 | 99 |
|   | 2 | 8 | — | — | — | 95 | 55 |

TABLE 9-continued

Fungicidal Activities

| Compound No. | Concentration (ppm) | RCV | RSB | CGM | TLB | WLR | BPM |
|---|---|---|---|---|---|---|---|
| 11 | 50 | 100 | 40 | 17 | 85 | 100 | 100 |
|   | 10 | 86 | — | — | — | 100 | 99 |
|   | 2 | 33 | — | — | — | 97 | 98 |
| 12 | 50 | 98 | 70 | 52 | 83 | 100 | 100 |
|   | 10 | 93 | — | — | — | 100 | 100 |
|   | 2 | 33 | — | — | — | 100 | 98 |
| 13 | 50 | 93 | 70 | 36 | 46 | 100 | 100 |
|   | 10 | 86 | — | — | — | 100 | 100 |
|   | 2 | 41 | — | — | — | 99 | 99 |
| 14 | 50 | 100 | 75 | 7 | 12 | 100 | 100 |
|   | 10 | 86 | — | — | — | 99 | 100 |
|   | 2 | 58 | — | — | — | 96 | 99 |
| 24 | 50 | 97 | 95 | 50 | 33 | 99 | 100 |
|   | 10 | 88 | 72 | — | — | 97 | 100 |
|   | 2 | 28 | 44 | — | — | 95 | 95 |
| 25 | 50 | 98 | 40 | 9 | 99 | 100 | 100 |
|   | 2 | 66 | 15 | — | 75 | 95 | 93 |
| 26 | 50 | 95 | 77 | 77 | 90 | 93 | 100 |
| 27 | 50 | 100 | 25 | 0 | 69 | 86 | 91 |
| 28 | 50 | 99 | 50 | 9 | 38 | 100 | 95 |
|   | 2 | 66 | 0 | — | 50 | 97 | 86 |
| 29 | 50 | 100 | 35 | 0 | 84 | 88 | 80 |
|   | 2 | 93 | 20 | — | 78 | 96 | 41 |
| 31 | 50 | 100 | 52 | 25 | 8 | 100 | 100 |
|   | 2 | 97 | — | — | — | 83 | 8 |
| 32 | 50 | 100 | 41 | 8 | 0 | 99 | 100 |
|   | 2 | 99 | — | — | — | 3 | 0 |
| 33 | 50 | 96 | 17 | 0 | 0 | 96 | 100 |
|   | 2 | 97 | — | — | — | 10 | 0 |
| 35 | 50 | 100 | 52 | 0 | 0 | 97 | 100 |
|   | 2 | 97 | — | — | — | 83 | 0 |
| 36 | 50 | 100 | 0 | 0 | 0 | 93 | 100 |
|   | 2 | 88 | — | — | — | 0 | 0 |
| 37 | 50 | 100 | 29 | 0 | 0 | 98 | 100 |
|   | 2 | 98 | — | — | — | 37 | 42 |
| 38 | 50 | 100 | 64 | 0 | 0 | 100 | 100 |
|   | 2 | 97 | — | — | — | 99 | 87 |
| 39 | 50 | 100 | 58 | 0 | 83 | 100 | 100 |
|   | 2 | 93 | — | — | — | 0 | 0 |
| 40 | 50 | 100 | 95 | 75 | 97 | 100 | 100 |
|   | 10 | 100 | 75 | — | 68 | 100 | 100 |
|   | 2 | 99 | 70 | — | 12 | 99 | 100 |
| 41 | 50 | 100 | 95 | 51 | 96 | 100 | 100 |
|   | 10 | 100 | 70 | — | 25 | 100 | 100 |
|   | 2 | 98 | 55 | — | 6 | 99 | 100 |
| 42 | 50 | 100 | 70 | 64 | 97 | 100 | 100 |
|   | 10 | 96 | — | — | — | 100 | 100 |
|   | 2 | 58 | — | — | — | 98 | 100 |
| 44 | 50 | 100 | 75 | 5 | 71 | 100 | 100 |
|   | 10 | 95 | — | — | — | 100 | 100 |
|   | 2 | 85 | — | — | — | 96 | 100 |
| 45 | 50 | 97 | 65 | 17 | 85 | 100 | 100 |
|   | 10 | 93 | — | — | — | 100 | 100 |
|   | 2 | 41 | — | — | — | 95 | 99 |
| 48 | 50 | 100 | 75 | 64 | 95 | 100 | 100 |
|   | 10 | 96 | — | — | — | 100 | 100 |
|   | 2 | 41 | — | — | — | 99 | 100 |
| 51 | 50 | 100 | 90 | 52 | 97 | 100 | 100 |
|   | 10 | 99 | 88 | — | — | 100 | 100 |
| 52 | 50 | 97 | 65 | 52 | 42 | 100 | 100 |
|   | 10 | 80 | — | — | — | 96 | 100 |
| 54 | 50 | 100 | 90 | 51 | 84 | 100 | 100 |
|   | 10 | 99 | 80 | — | — | 100 | 100 |
|   | 2 | 97 | 50 | — | — | 97 | 99 |
| 56 | 50 | 95 | 70 | 5 | 57 | 100 | 100 |
|   | 10 | 80 | — | — | — | 100 | 100 |
|   | 2 | 25 | — | — | — | 95 | 100 |
| 57 | 50 | 99 | 47 | 8 | 0 | 98 | 98 |
|   | 2 | 95 | — | — | — | 27 | 0 |
| 58 | 50 | 100 | 23 | 8 | 0 | 98 | 98 |
| 59 | 50 | 100 | 47 | 0 | 0 | 73 | 91 |
| 60 | 50 | 100 | 29 | 8 | 0 | 66 | 100 |
| 61 | 50 | 91 | 23 | 33 | 0 | 43 | 86 |

TABLE 9-continued

Fungicidal Activities

| Compound No. | Concentration (ppm) | RCV | RSB | CGM | TLB | WLR | BPM |
|---|---|---|---|---|---|---|---|
| 62 | 50 | 96 | 0 | 25 | 0 | 99 | 100 |
|  | 2 | 92 | — | — | — | 83 | 0 |
| 63 | 50 | 96 | 11 | 33 | 0 | 90 | 97 |
| 64 | 50 | 100 | 85 | 75 | 95 | 100 | 100 |
|  | 10 | 100 | 65 | — | 90 | 100 | 100 |
|  | 2 | 100 | 45 | — | 87 | 99 | 100 |
| 65 | 50 | 100 | 100 | 71 | 0 | 100 | 100 |
|  | 10 | 100 | 60 | — | — | 100 | 100 |
|  | 2 | 100 | 30 | — | — | 99 | 99 |
| 66 | 50 | 100 | 100 | 75 | 0 | 100 | 100 |
|  | 10 | 100 | 65 | — | — | 100 | 100 |
|  | 2 | 100 | 20 | — | — | 99 | 100 |
| 67 | 50 | 100 | 100 | 37 | 0 | 100 | 100 |
|  | 10 | 100 | 43 | — | — | 100 | 100 |
|  | 2 | 100 | 10 | — | — | 99 | 99 |
| 68 | 50 | 100 | 100 | 56 | 20 | 100 | 100 |
|  | 10 | 100 | 70 | — | — | 100 | 100 |
|  | 2 | 100 | 30 | — | — | 99 | 100 |
| 69 | 50 | 100 | 100 | 25 | 60 | 100 | 100 |
|  | 2 | 100 | 30 | — | 25 | 97 | 99 |
| 70 | 50 | 100 | 85 | 50 | 0 | 97 | 100 |
|  | 2 | 99 | 20 | — | 12 | 93 | 83 |
| 71 | 50 | 100 | 100 | 25 | 50 | 100 | 100 |
|  | 2 | 100 | 35 | — | 25 | 98 | 100 |
| 72 | 50 | 98 | 65 | 0 | 66 | 100 | 100 |
|  | 2 | 100 | 25 | — | 0 | 98 | 100 |
| 73 | 50 | 95 | 100 | 0 | 60 | 100 | 100 |
|  | 2 | 100 | 25 | — | 0 | 98 | 100 |
| 74 | 50 | 100 | 100 | 72 | 56 | 100 | 100 |
|  | 2 | 100 | 25 | — | 12 | 99 | 100 |
| 75 | 50 | 100 | 100 | 0 | 66 | 100 | 100 |
|  | 2 | 100 | 25 | — | 0 | 98 | 100 |
| 76 | 50 | 100 | 100 | 62 | 0 | 100 | 100 |
|  | 2 | 100 | 35 | — | 0 | 100 | 100 |
| 77 | 50 | 100 | 100 | 85 | 80 | 100 | 100 |
|  | 10 | 100 | 57 | 36 | 88 | 100 | 100 |
|  | 2 | 100 | 40 | 21 | 50 | 100 | 100 |
| 78 | 50 | 100 | 90 | 82 | 94 | 100 | 100 |
|  | 2 | 100 | 45 | — | 50 | 100 | 100 |
| 79 | 50 | 100 | 65 | 80 | 82 | 100 | 100 |
|  | 2 | 99 | 35 | — | 43 | 98 | 100 |
| 80 | 50 | 100 | 100 | 77 | 72 | 100 | 100 |
|  | 2 | 100 | 45 | — | 12 | 96 | 100 |
| 81 | 50 | 100 | 100 | 83 | 64 | 100 | 100 |
|  | 2 | 100 | 30 | — | 12 | 99 | 100 |
| 82 | 50 | 96 | 85 | 82 | 84 | 100 | 100 |
|  | 2 | 100 | 55 | — | 85 | 100 | 100 |
| 85 | 50 | 93 | 40 | 7 | 0 | 96 | 99 |
|  | 10 | 16 | — | — | — | 93 | 92 |
| 89 | 50 | 80 | 50 | 0 | 12 | 96 | 100 |
|  | 10 | — | — | — | — | 70 | 99 |
| 90 | 50 | 76 | 35 | 9 | 27 | 86 | 99 |
|  | 10 | — | — | — | — | — | 97 |
| 94 | 50 | 100 | 60 | 54 | 68 | 100 | 100 |
|  | 10 | 100 | — | — | — | 96 | 100 |
|  | 2 | 99 | — | — | — | 93 | 100 |
| 102 | 50 | 99 | 50 | 23 | 0 | 99 | 100 |
|  | 10 | 86 | — | — | — | 96 | 100 |
|  | 2 | 71 | — | — | — | 94 | 97 |
| 104 | 50 | 96 | 45 | 0 | 0 | 97 | 100 |
|  | 10 | 75 | — | — | — | 93 | 99 |
|  | 2 | 25 | — | — | — | 66 | 80 |
| 105 | 50 | 0 | 20 | 0 | 0 | 100 | 100 |
|  | 10 | — | — | — | — | 98 | 99 |
|  | 2 | — | — | — | — | 86 | 98 |
| 111 | 50 | 0 | 0 | 17 | 0 | 98 | 100 |
|  | 10 | — | — | — | — | 95 | 100 |
|  | 2 | — | — | — | — | 80 | 95 |
| 113 | 50 | 0 | 20 | 0 | 21 | 100 | 100 |
|  | 10 | — | — | — | — | 98 | 96 |
|  | 2 | — | — | — | — | 86 | 86 |
| 116 | 50 | 0 | 15 | 0 | 14 | 96 | 100 |
|  | 10 | — | — | — | — | 96 | 96 |
|  | 2 | — | — | — | — | 53 | 33 |
| 118 | 50 | 33 | 30 | 36 | 0 | 100 | 100 |
|  | 10 | — | — | — | — | 98 | 96 |
|  | 2 | — | — | — | — | 91 | 88 |
| 131 | 50 | 80 | 55 | 42 | 4 | 100 | 100 |
|  | 2 | 43 | — | — | — | 98 | 76 |
| 135 | 50 | 86 | 61 | 71 | 0 | 100 | 100 |
|  | 2 | 43 | 20 | — | — | 94 | 93 |
| 139 | 50 | 100 | 20 | 0 | 46 | 98 | 98 |
|  | 2 | 53 | 10 | — | — | 93 | 97 |
| 140 | 50 | 97 | 64 | 0 | 0 | 100 | 86 |
|  | 2 | 86 | — | — | — | 0 | — |
| 143 | 50 | 100 | 58 | 0 | 0 | 90 | 93 |
|  | 2 | 83 | — | — | — | 36 | 0 |
| 144 | 50 | 96 | 47 | 0 | 0 | 86 | 95 |
|  | 2 | 88 | — | — | — | — | 0 |
| 145 | 50 | 100 | 64 | 0 | 0 | 100 | 100 |
|  | 2 | 83 | — | — | — | 83 | 33 |
| 150 | 50 | 100 | 92 | 44 | 50 | 100 | 100 |
|  | 10 | 100 | 65 | — | — | 100 | 100 |
|  | 2 | 83 | 55 | — | — | 95 | 100 |
| 151 | 50 | 100 | 95 | 24 | 12 | 100 | 100 |
|  | 10 | 99 | 55 | — | — | 95 | 100 |
|  | 2 | 93 | 35 | — | — | 86 | 98 |
| 152 | 50 | 100 | 90 | 44 | 0 | 100 | 100 |
|  | 10 | 97 | 60 | — | — | 98 | 100 |
|  | 2 | 86 | 45 | — | — | 86 | 95 |
| 153 | 50 | 86 | 55 | 20 | 13 | 100 | 100 |
|  | 10 | 25 | — | — | — | 100 | 99 |
|  | 2 | 0 | — | — | — | 91 | 83 |
| 154 | 50 | 16 | 90 | 58 | 12 | 98 | 100 |
|  | 10 | — | 35 | — | — | 96 | 98 |
|  | 2 | — | 25 | — | — | 73 | 68 |
| 155 | 50 | 80 | 60 | 52 | 6 | 100 | 100 |
|  | 10 | — | — | — | — | 99 | 99 |
|  | 2 | — | — | — | — | 83 | 95 |
| 156 | 50 | 33 | 20 | 36 | 0 | 93 | 92 |
|  | 10 | — | — | — | — | 95 | 91 |
| 157 | 50 | 93 | 60 | 68 | 6 | 100 | 100 |
|  | 10 | 76 | — | — | — | 100 | 99 |
|  | 2 | 33 | — | — | — | 98 | 97 |
| 158 | 50 | 41 | 70 | 44 | 0 | 100 | 100 |
|  | 10 | — | — | — | — | 98 | 100 |
|  | 2 | — | — | — | — | 91 | 98 |
| 159 | 50 | 96 | 65 | 52 | 20 | 100 | 100 |
|  | 10 | 91 | — | — | — | 100 | 100 |
|  | 2 | 25 | — | — | — | 94 | 99 |
| 160 | 50 | 100 | 70 | 36 | 92 | 100 | 100 |
|  | 10 | 100 | — | — | — | 100 | 100 |
|  | 2 | 86 | — | — | — | 99 | 99 |
| 163 | 50 | 90 | 92 | 51 | 12 | 100 | 100 |
|  | 10 | 86 | 40 | — | — | 98 | 100 |
|  | 2 | 58 | 40 | — | — | 86 | 94 |
| 164 | 50 | 41 | 20 | 36 | 0 | 96 | 100 |
|  | 10 | — | — | — | — | 95 | 99 |
|  | 2 | — | — | — | — | 60 | 71 |
| 165 | 50 | 80 | 45 | 68 | 6 | 100 | 100 |
|  | 10 | — | — | — | — | 96 | 99 |
|  | 2 | — | — | — | — | 86 | 71 |
| 173 | 50 | 97 | 100 | 25 | 20 | 100 | 100 |
|  | 2 | 93 | 30 | — | — | 99 | 99 |
| 174 | 50 | 96 | 60 | 0 | 0 | 100 | 100 |
|  | 2 | 86 | 25 | — | — | 90 | 99 |
| 175 | 50 | 96 | 65 | 12 | 0 | 100 | 100 |
|  | 2 | 76 | 10 | — | — | 86 | 83 |
| 176 | 50 | 86 | 60 | 12 | 70 | 100 | 100 |
|  | 2 | 83 | 20 | — | — | 60 | 80 |
| 180 | 50 | 100 | 60 | 56 | 56 | 100 | 100 |
|  | 2 | 86 | 25 | — | — | 97 | 98 |
| 181 | 50 | 95 | 45 | 77 | 30 | 99 | 100 |
|  | 2 | 98 | 35 | — | 68 | 83 | 83 |

TABLE 9-continued

Fungicidal Activities

| Compound No. | Concentration (ppm) | RCV | RSB | CGM | TLB | WLR | BPM |
|---|---|---|---|---|---|---|---|
| 182 | 50 | 95 | 50 | 77 | 40 | 100 | 100 |
|  | 2 | 95 | 30 | — | 62 | 95 | 96 |
| 183 | 50 | 100 | 100 | 56 | 50 | 100 | 100 |
|  | 2 | 99 | 20 | — | 12 | 99 | 100 |
| 184 | 50 | 96 | 85 | 0 | 50 | 99 | 100 |
|  | 2 | 90 | 20 | — | 0 | 98 | 99 |
| 185 | 50 | 96 | 75 | 0 | 50 | 100 | 100 |
|  | 2 | 73 | 25 | — | 25 | 95 | 98 |
| 186 | 50 | 83 | 50 | 25 | 0 | 99 | 100 |
|  | 2 | 73 | 15 | — | 0 | 66 | 86 |
| 187 | 50 | 83 | 85 | 0 | 0 | 100 | 98 |
|  | 2 | 97 | 20 | — | 25 | 95 | 97 |
| 188 | 50 | 71 | 55 | 0 | 40 | 95 | 100 |
|  | 2 | 76 | 0 | — | 0 | 66 | 91 |
| 190 | 50 | 93 | 65 | 0 | 0 | 100 | 100 |
|  | 2 | 66 | 15 | — | 0 | 93 | 91 |
| 191 | 50 | 100 | 75 | 68 | 60 | 100 | 100 |
|  | 2 | 100 | 35 | — | 0 | 99 | 100 |
| 192 | 50 | 100 | 100 | 75 | 40 | 100 | 100 |
|  | 2 | 100 | 40 | — | 37 | 98 | 100 |
| 193 | 50 | 96 | 80 | 75 | 40 | 100 | 100 |
|  | 2 | 93 | 30 | — | 12 | 98 | 90 |
| 194 | 50 | 100 | 64 | 16 | 0 | 98 | 98 |
|  | 2 | 95 | — | — | — | 20 | 0 |
| 195 | 50 | 96 | 80 | 82 | 50 | 100 | 100 |
|  | 2 | 100 | 25 | — | 25 | 98 | 99 |
| 197 | 50 | 100 | 80 | 85 | 50 | 100 | 100 |
|  | 2 | 100 | 35 | — | 0 | 98 | 100 |
| 198 | 50 | 100 | 58 | 16 | 0 | 100 | 100 |
|  | 2 | 95 | — | — | — | 53 | 41 |
| 199 | 50 | 100 | 100 | 80 | 60 | 100 | 100 |
|  | 2 | 100 | 35 | — | 12 | 99 | 100 |
| 200 | 50 | 96 | 85 | 81 | 50 | 100 | 100 |
|  | 2 | 95 | 15 | — | 12 | 93 | 99 |
| 201 | 50 | 97 | 85 | 85 | 50 | 100 | 100 |
|  | 2 | 98 | 20 | — | 25 | 97 | 100 |
| 221 | 50 | 41 | 30 | 0 | 0 | 100 | 100 |
|  | 10 | — | — | — | — | 91 | 96 |
| ORIBRIGHT[1)] | 10 | 90 | 70 | 7 | 40 | 60 | 83 |
|  | 2 | 60 | 15 | 20 | 0 | 15 | 50 |
|  | 0.40 | 8 | 0 | 7 | 0 | 15 | 0 |
|  | 0.08 | 0 | 0 | 0 | 0 | 10 | 0 |
| FENARIMOL[2)] | 10 | 0 | 85 | 7 | 80 | 100 | 100 |
|  | 2 | 0 | 40 | 7 | 75 | 80 | 100 |
|  | 0.40 | 0 | 30 | 7 | 60 | 15 | 95 |
|  | 0.08 | 0 | 14 | 0 | 0 | 15 | 50 |

[1)]: a product of Japan, Shionogi
[2)]: a product of U.S.A., Dow Elanco

As can be seen from Table 9, the compounds of the present invention have a broad fungicidal activity spectrum against the target fungi when compared with the control compounds such as ORIBRIGHT™ and FENARIMOL™. In particular, the inventive compounds have excellent fungicidal activity against RCB, RSB, WLR and BPM.

While the invention has been described with respect to the specific embodiments, it should be recognized that various modifications and changes may be made by those skilled in the art to the invention which also fall within the scope of the invention as defined by the appended claims.

What is claimed is:

1. A compound of formula (I) or a stereoisomer thereof:

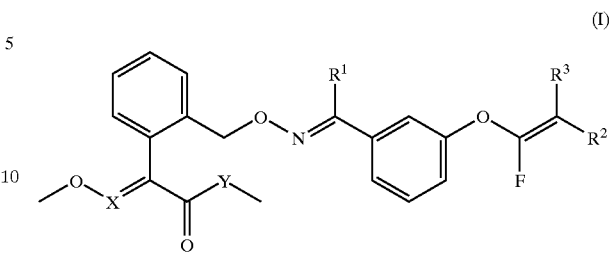

(I)

wherein,

X is CH or N;

Y is O or NH;

$R^1$ is hydrogen, $C_{1-4}$ alkyl, or halogen-substituted $C_{1-4}$ alkyl, $R^2$ is a phenyl group optionally carrying one or more substituents selected from the group consisting of $C_{1-4}$ alkyl, $C_{1-4}$ alkoxy, methylenedioxy and halogen; or a naphthyl group; and $R^3$ is hydrogen or $CF_3$.

2. The compound of claim 1, wherein $R^1$ is hydrogen or $C_{1-4}$ alkyl, and $R^2$ is a phenyl group optionally carrying one or more halogen radicals.

3. A process for the preparation of a compound of formula (I-a), which comprises: (a) reacting a compound of formula (II) with a compound of formula (m) in the presence of a base to obtain a compound of formula (IV); (b) debenzylating the compound of formula (IV) by hydrogenolysis in the presence of a Pd-based catalyst to obtain a compound of formula (V-a); and (c) reacting the compound of formula (V-a) with a compound of formula (VI) in the presence of a base:

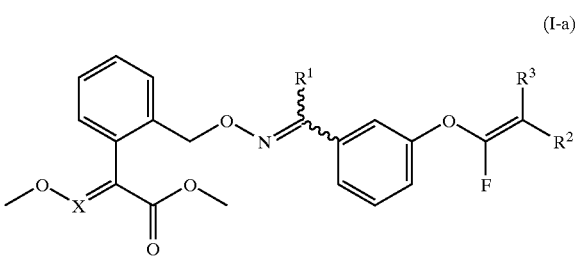

(I-a)

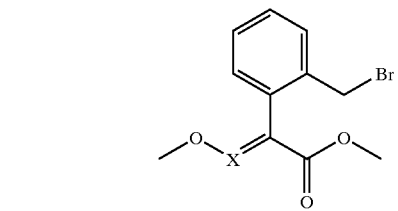

(II)

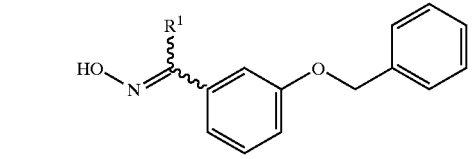

(III)

-continued (IV)
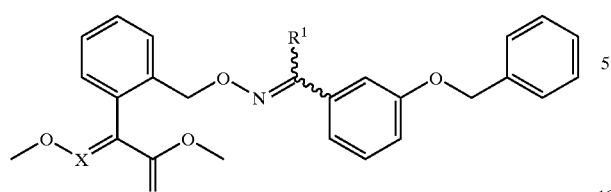

(V-a)
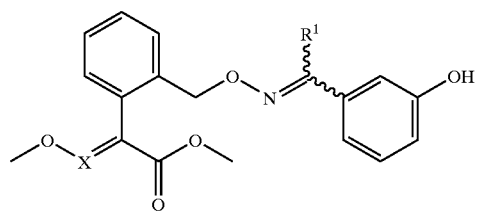

(VI)
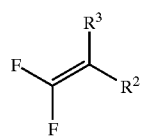

wherein, X, R¹, R² and R³ have the same meanings as defined in claim 1.

4. A process for the preparation of a compound of formula (I-b), which comprises (a) reacting the phenolic ester compound of formula (V-a) according to claim 3 with methylamine to obtain a compound of formula (V-b) and (b) reacting the compound of formula (V-b) with a compound of formula (VI) in the presence of a base:

(I-b)
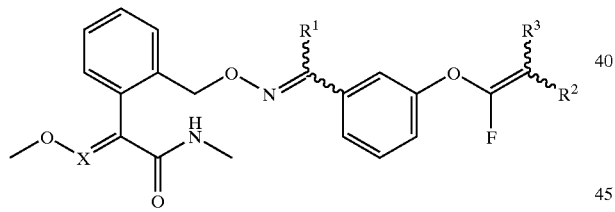

(V-b)
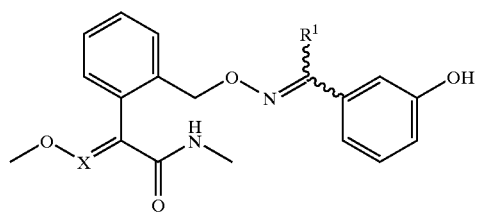

(VI)
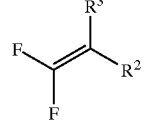

wherein, X, R¹, R² and R³ have the same meanings as defined in claim 1.

5. A process for the preparation of a compound of formula (I-a), which comprises reacting a compound of formula (II) with a compound of formula (VII) in the presence of a base:

(I-a)
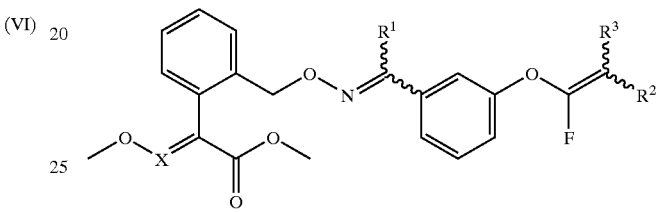

(II)
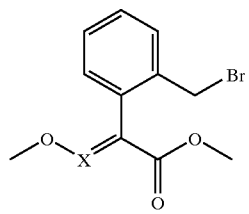

(VII)
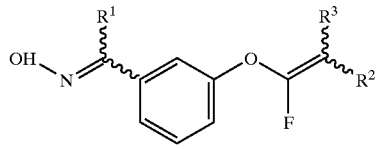

wherein, X, R¹, R² and R³ have the same meanings as defined in claim 1.

6. A fungicidal composition comprising a fungicidally effective amount of the compound according to claim 1 as an active ingredient and an inert carrier.

7. A fungicidal composition comprising a fungicidally effective amount of the compound according to claim 2 as an active ingredient and an inert carrier.

* * * * *